United States Patent
Gilbert et al.

(10) Patent No.: US 12,365,920 B2
(45) Date of Patent: *Jul. 22, 2025

(54) ADENOVIRAL VECTOR

(71) Applicant: Oxford University Innovation Limited, Oxfordshire (GB)

(72) Inventors: Sarah C. Gilbert, Oxfordshire (GB); Adrian V S Hill, Oxfordshire (GB); Matthew G. Cottingham, Oxfordshire (GB); Matthew Dicks, Oxfordshire (GB); Susan J. Morris, Oxfordshire (GB); Alexander Douglas, Oxfordshire (GB)

(73) Assignee: Oxford University Innovation Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/624,929

(22) Filed: Apr. 2, 2024

(65) Prior Publication Data
US 2024/0301443 A1 Sep. 12, 2024

Related U.S. Application Data

(63) Continuation of application No. 17/587,376, filed on Jan. 28, 2022, now Pat. No. 11,970,709, which is a continuation of application No. 16/310,281, filed as application No. PCT/GB2017/051851 on Jun. 23, 2017, now Pat. No. 11,306,325.

(30) Foreign Application Priority Data

Jun. 23, 2016 (GB) ...................... 1610967

(51) Int. Cl.
| | | |
|---|---|---|
| A61K 35/761 | (2015.01) | |
| A61K 39/00 | (2006.01) | |
| A61K 39/04 | (2006.01) | |
| A61K 39/12 | (2006.01) | |
| A61K 39/145 | (2006.01) | |
| A61K 39/235 | (2006.01) | |
| A61P 31/16 | (2006.01) | |
| C12N 15/86 | (2006.01) | |
| C12N 15/861 | (2006.01) | |
| A61K 39/21 | (2006.01) | |
| A61P 31/06 | (2006.01) | |

(52) U.S. Cl.
CPC .......... *C12N 15/861* (2013.01); *A61K 35/761* (2013.01); *A61K 39/12* (2013.01); *A61K 39/145* (2013.01); *A61K 39/235* (2013.01); *A61P 31/16* (2018.01); *C12N 15/86* (2013.01); *C12N 15/8613* (2013.01); *A61K 39/00* (2013.01); *A61K 39/04* (2013.01); *A61K 39/21* (2013.01); *A61P 31/06* (2018.01); *C12N 2710/10044* (2013.01); *C12N 2710/10343* (2013.01); *Y02A 50/30* (2018.01)

(58) Field of Classification Search
CPC ...... A61K 35/761; A61K 39/00; A61K 39/12; A61K 39/04; A61K 39/235
See application file for complete search history.

(56) References Cited

U.S. PATENT DOCUMENTS

| | | |
|---|---|---|
| 2012/0027788 A1 | 2/2012 | Colloca et al. |
| 2015/0044766 A1 | 2/2015 | Dicks et al. |

FOREIGN PATENT DOCUMENTS

| | | |
|---|---|---|
| EP | 3475433 B1 | 7/2021 |
| WO | 2005/071093 | 8/2005 |
| WO | 2012/172277 | 12/2012 |
| WO | 2013/052832 | 4/2013 |
| WO | 2015/052543 | 4/2015 |
| WO | 2015/063647 | 5/2015 |
| WO | 2016/016651 | 2/2016 |

OTHER PUBLICATIONS

Extended European Search Report dated Dec. 17, 2021 for European Patent Application No. 21182840.5, 15 pages.
Examination Report dated Feb. 21, 2020 for European Patent Application No. 17734440, 8 pages.
Buchbinder et al, Efficacy assessment of a cell-mediated immunity HIV-1 vaccine (the Step Study): a double-blind, randomised, placebo-controlled, test-of-concept trial; Lancet, vol. 372, Nov. 2008.
Farina et al Replication-Defective Vector Based on a Chimpanzee Adenovirus; J. Virol, Dec. 2001, p. 11603-11613.
Dudareva et al, Prevalence of serum neutralizing antibodies against chimpanzee adenovirus 63 and human adenovirus 5 in Kenyan children, in the context of vaccine vector efficacy; Vaccine 27, 2009, 3501-3504.
R. Wigand et al, Chimpanzee Adenoviruses Are Related to Four Subgenera of Human Adenoviruses; Intervirology, vol. 30; 1 1989.
Roy et al, Characterization of a family of chimpanzee adenoviruses and development of molecular clones for gene transfer vectors; Hum. Gen. Ther., 2004, 15:519-530.

(Continued)

*Primary Examiner* — Barry A Chestnut
(74) *Attorney, Agent, or Firm* — Morgan, Lewis & Bockius LLP

(57) ABSTRACT

The present invention provides recombinant adenoviral vectors, immunogenic compositions thereof and their uses in medicine. In particular, the present invention provides an adenoviral vector comprising the genome of an adenovirus other than AdHu5 and AdY25, wherein the genome of the adenovirus has been modified such that the vector lacks the native E4 locus of the adenovirus and comprises heterologous E4Orf1, E4Orf2 and E4Orf3 coding regions from AdY25.

21 Claims, 10 Drawing Sheets

Specification includes a Sequence Listing.

(56) References Cited

OTHER PUBLICATIONS

The trusted leader in cloning technology; http://www.invitrogen.com/gateway.

Havenga et al, Novel replication-incompetent adenoviral B-group vectors: high vector stability and yield in PER.C6 cells; J.G.V., 2006, 87, 2135-214.

Warming, S. et al. Simple and highly efficient BAC recombineering using galK selection; Nucleic Acids Res, Feb. 24, 2005; 33(4): e36.

Colloca, S., et al., Vaccine vectors derived from a large collection of simian adenoviruses induce potent cellular immunity across multiple species; Sci Transl Med, 2012. 4(115): p. 115ra2.

Quinn, K.M., et al. Comparative Analysis of the Magnitude, Quality, Phenotype, and Protective Capacity of Simian Immunodeficiency Virus Gag-Specific CD8 + T Cells following Human-, Simian-, and Chimpanzee-Derived Recombinant Adenoviral Vector Immunization; J Immunol, 2013. 190(6): p. 2720-35.

Office Action dated Nov. 10, 2021 for Mexican Patent Application No. MX/a/2018/016074, 9 pages.

Written Opinion dated Apr. 22, 2020 for Singapore Application No. 11201811178U, 6 pages.

Cottingham et al., "Preventing Spontaneous Genetic Rearrangements in the Transgene Cassettes of Adenovirus Vectors", Biotechnology and Bioengineering, Mar. 2012, 109(3), pp. 719-728.

Dicks, et al. "A Novel Chimpanzee Adenovirus Vector with Low Human Seroprevalence: Improved Systems for Vector Derivation and Comparative Immunogenicity", PLoS one, Jul. 2012, 7(7), 12 pages.

Dicks, et al., "The Relative Magnitude of Transgene-Specific Adaptive Immune Responses Induced by Human and Chimpanzee Adenovirus Vectors differs between Laboratory Animals and a Target Species", Vaccine, Jan. 2015, 33, pp. 1121-1128.

Great Britain Patent Application No. 1610967.0, Search Report, dated Mar. 23, 2017, 2 pages.

International Patent Application No. PCT/GB2017/051851, International Search Report, dated Sep. 12, 2017, 6 pages.

International Patent Application No. PCT/GB2017/051851, Written Opinion of the International Searching Authority, dated Sep. 12, 2017, 8 pages.

Kapulu et al., "Comparative Assessment of Transmission-Blocking Vaccine Candidates Against Plasmodium ralciparum", Scientific Reports, Jun. 2015, 5(1), 15 pages.

Morris, et al., "Simian Adenoviruses as Vaccine Vectors", Future Virology, Sep. 2016, 11 (9), pp. 649-659.

Roshorm et al., "T Cells Induced by Recombinant Chimpanzee Adenovirus Alone and in Prime-boost regimens decrease chimeric EcoHIV/NDK challenge virus load", Eur J Immunol., 2012 42(12), pp. 3243-3255.

Thomas et al., "Effects of the Deletion of Early Region 4 (E4) Open Reading Frame 1 (orf1 ), orf1-2, orf1-3 and orf1-4 on Virus-Host Cell Interaction, Transgene Expression, and Immunogenicity of Replicating Adenovirus HIV Vaccine Vectors", PLoS one, Oct. 2013, 8(10), 14 pages.

| Group | ChAdOx2 HAV dose |
|---|---|
| 1 (n=3) | $5 \times 10^9$ vp |
| 2 (n=3) | $2.5 \times 10^{10}$ vp |
| 3 (n=3-6) | $5 \times 10^{10}$ vp |

Table 1.

Table 2.

ChAdOx2 HAV

| | Participant | D0 | D2 | D7 | D14 | D28 | D56 | D364 |
|---|---|---|---|---|---|---|---|---|
| Group 1 | 00101002 | 15/03/2017 | 17/03/2017 | 22/03/2017 | 29/03/2017 | 12/04/2017 | 10/05/2017 | 14/03/2018 |
| | 00101003 | 21/03/2017 | 23/03/2017 | 28/03/2017 | 04/04/2017 | 18/04/2017 | 16/05/2017 | 20/03/2018 |
| | 00101005 | 21/03/2017 | 23/03/2017 | 28/03/2017 | 04/04/2017 | 18/04/2017 | 16/05/2017 | 20/03/2018 |
| Group 2 | 00101004 | 04/04/2017 | 06/04/2017 | 11/04/2017 | 18/04/2017 | 02/05/2017 | 30/05/2017 | 03/04/2018 |
| | 00101006 | 11/04/2017 | 13/04/2017 | 18/04/2017 | 25/04/2017 | 09/05/2017 | 06/06/2017 | 10/04/2018 |
| | 00101008 | 11/04/2017 | 13/04/2017 | 18/04/2017 | 25/04/2017 | 09/05/2017 | 06/06/2017 | 10/04/2018 |
| Group 3 | 00101011 | 17/05/2017 | 19/05/2017 | 24/05/2017 | 31/05/2017 | 14/06/2017 | 12/07/2017 | 16/05/2018 |
| | 00101018 | 23/05/2017 | 25/05/2017 | 30/05/2017 | 06/06/2017 | 20/06/2017 | 18/07/2017 | 22/05/2018 |
| | 00101010 | 24/05/2017 | 26/05/2017 | 31/05/2017 | 07/06/2017 | 21/06/2017 | 19/07/2017 | 23/05/2018 |

|         |       |            | SFC per million PBMC |        |       |
|---------|-------|------------|------|--------|-------|
| Patient | Group | Dose (v.p.)| D0   | D28    | D56   |
| 002     |       |            | 82.7 | 65.3   | 36.0  |
| 003     | 1     | $5 \times 10^9$ | 248.0 | 38.7 | 104.0 |
| 005     |       |            | 80.0 | 128.0  | 40.0  |
| 004     |       |            | 61.3 | 1701.3 | 624.0 |
| 006     | 2     | $2.5 \times 10^{10}$ | 104.0 | 1033.3 | |
| 008     |       |            | 24.7 | 534.7  |       |
| 010     |       |            | 233.3|        |       |
| 011     | 3     | $5 \times 10^{10}$ | 129.3 |    |       |
| 018     |       |            | 178.7|        |       |

SEQUENCE LISTING

```
Sequence total quantity: 21
SEQ ID NO: 1            moltype = DNA  length = 36519
FEATURE                 Location/Qualifiers
source                  1..36519
                        mol_type = other DNA
                        organism = synthetic construct
misc_feature            1..36519
                        note = Chimpanzee adenovirus C68
SEQUENCE: 1
ccatcttcaa taatatacct caaacttttt gtgcgcgtta atatgcaaat gaggcgtttg   60
aatttgggga ggaagggcgg tgattggtcg agggatgagc gaccgttagg ggcggggcga  120
gtgacgtttt gatgacgtgg ttgcgaggag gagccagttt gcaagttctc gtgggaaaag  180
tgacgtcaaa cgaggtgtgg tttgaacacg gaaatactca atttcccgc gctctctgac   240
aggaaatgag gtgtttctgg gcggatgcaa gtgaaacgg gccattttcg cgcgaaaact  300
gaatgaggaa gtgaaaatct gagtaatttc gcgtttatgg cagggaggag tatttgccga  360
gggccgagta gactttgacc gattacgtgg gggtttcgat taccgtgttt ttcacctaaa  420
tttccgcgta cggtgtcaaa gtccggtgtt tttacgtagg tgtcagctga tcgccagggt  480
atttaaacct gcgctctcca gtcaagaggc cactcttgag tgccagcgag aagagtttc   540
tcctccgcgc cgcgagtcag atctacactt tgaaagatga ggcacctgag agacctgccc  600
gatgagaaaa tcatcatcgc ttccgggaac gagattctga actggtggt aaatgccatg  660
atgggcgacg accctccgga gccccccacc ccatttgaca caccttccgc gcacgatttg  720
tatgatctgg aggtggatgt gcccgaggac gatcccaatg aggaggcggt aaatgatttt  780
tttagcgatg ccgcgctgct agctgccgag gaggcttcga gctctagctc agacagcgac  840
tcttcactgc ataccccag accccggcaga ggtgagaaaa agatccccga gcttaaaggg  900
gaagagatgg acttgcgctg ctatgaggaa tgcttgcccc cgagcgatga tgaggacgag  960
caggcgatcc agaacgcagc gagccaggga gtgcaagccg ccagcgagag ctttgcgctg 1020
gactgcccgc ctctgcccgg acacggctgt aagtcttgtg aatttcatcg catgaatact 1080
ggagataaag ctgtgttgtg tgcactttgc tatatgagag cttacaacca ttgtgtttac 1140
agtaagtgtg attaagttga actttagagg gaggcagaga gcagggtgac tgggcgatga 1200
ctggttatt tatgtatata tgttctttat ataggtcccg tctctgacgc agatgatgag 1260
accccactca caaagtccac ttcgtcaccc ccagaaattg gcacatctcc acctgagaat 1320
attgttagac cagttcctgt tagagccact gggaggagag cagctgtgga atgtttggat 1380
gacttgctac agggtgggt tgaaccttg gacttgtgta cccggaaacg ccccaggcac 1440
taagtgccac acatgtgtgt ttacttgagg tgatgtcagt atttataggg tgtggagtgc 1500
aataaaaaat gtgttgactt taagtgcgtg gtttatgact caggggtggg gactgtgagt 1560
atataagcag gtgcagacct gtgtggttag ctcagagcgg catggagatt tggacggtct 1620
tggaagactt tcacaagact agacagctgc tagagaacgc ctcgaacgga gtctcttacc 1680
tgtggagatt ctgcttcgt ggcgacctag ctaggctagt ctacagggcc aaacaggatt 1740
atagtgaaca atttgaggtt atttttgagag agtgttctgg tcttttgac gctcttaact 1800
tgggccatca gtctcacttt aaccagagga tttcgagagc ccttgatttt actactcctg 1860
gcagaaccac tgcagcagta gccttttttg cttttattct tgacaaatgg agtcaagaaa 1920
cccatttcag cagggattac cagctggatt tcttagcagt agctttgtgg agaacatgga 1980
agtgccagcg cctgaatgca atctccggct acttgccggt acagccgcta gacactctga 2040
ggatcctgaa tctccaggag agtcccaggg cacgccaacg tcgccagcag cagcagcagg 2100
aggaggatca agaagagaac ccgagagccg gcctggaccc tccggcggag gaggaggagt 2160
agctgacctg tttcctgaac tgcgccgggt gctgactagg tcttcgagtg gtcgggagag 2220
ggggattaag cgggagaggc atgatgagac taatcacaga actgaactga ctgtgggtct 2280
gatgagtcgc aagcgcccag aaacagtgtg gtggcatgag gtgcagtcga ctggcacaga 2340
tgaggtgtcg gtgatgcatg agaggttttc tctagaacaa gtcaagactt gttggttaga 2400
gcctgaggat gattgggagg tagccatcag gaattatgcc aagctggctc tgaggccaga 2460
caagaagtac aagattacta gctgataaa tatcagaaat gcctgctaca tctcagggaa 2520
tggggctgaa gtgagagatct gtctccagga aagggtggct tcagatgct gcatgatgaa 2580
tatgtacccg ggagtggtgg gcatggatgg ggttaccttt atgaacatga ggttcagggg 2640
agatgggtat aatggcacgg tctttatggc caataccaag ctgacagtcc atggctgctc 2700
cttcttggg tttaataaca cctgcatcga ggcctggggt caggtcggtg tgaggggctg 2760
cagttttcca gccaactgga tggggcgt ggccaggacc aagagtatgc tgtccgtgaa 2820
gaaatgcttg tttgagaggt gccacctggg ggtgatgagc gagggcgaag ccagaatccg 2880
ccactgcgcc tctaccgaga cggcctgctt tgtgctgtgc aagggcaatg ctaagatcaa 2940
gcataatatg atctgtggag cctcgacga gcgcggctac cagatgctga cctgcgccgg 3000
cgggaacagc catatgctgg ccaccgtaca tgtggcttcc catgctcgca gcccctggcc 3060
cgagttcgag cacaatgtca tgaccaggtg caatatgcat ctggggtccc gccgaggcat 3120
```

-continued

```
gttcatgccc taccagtgca acctgaatta tgtgaaggtg ctgctggagc ccgatgccat  3180
gtccagagtg agcctgacgg gggtgtttga catgaatgtg gaggtgtgga agattctgag  3240
atatgatgaa tccaagacca ggtgccgagc ctgcgagtgc ggagggaagc atgccaggtt  3300
ccagcccgtg tgtgtggatg tgacggagga cctgcgaccc gatcatttgg tgttgccctg  3360
caccgggacg gagttcggtt ccagcgggga agaatctgac tagagtgagt agtgttctgg  3420
ggcgggggag gacctgcatg agggccagaa taactgaaat ctgtgctttt ctgtgtgttg  3480
cagcagcatg agcggaagcg gctcctttga gggaggggta ttcagcccct atctgacggg  3540
gcgtctcccc tcctgggcgg gagtgcgtca gaatgtgatg ggatccacgg tggacggccg  3600
gcccgtgcag cccgcgaact cttcaaccct gacctatgca accctgagct cttcgtcgtg  3660
ggacgcagct gccgccgcag ctgctgcatc tgccgccagc gccgtgcgcg gaatggccat  3720
gggcgccggc tactacggca ctctggtggc caactcgagt tccaccaata atcccgccag  3780
cctgaacgag gagaagctgt tgctgctgat ggcccagctc gaggccttga cccagcgcct  3840
gggcgagctg acccagcagg tggctcagct gcaggagcag acgcgggccg cggttgccac  3900
ggtgaaatcc aaataaaaaa tgaatcaata aataaacgga cgggttgtt gattttaaca  3960
cagagtctga atctttattt gattttttcgc gcgcggtagg ccctggacca ccggtctcga  4020
tcattgagca cccggtggat cttttccagg acccggtaga ggtgggcttg gatgttgagg  4080
tacatgggca tgagcccgtc ccgggggtgg aggtagctcc attgcagggc ctcgtgctcg  4140
ggggtggtgt tgtaaatcac ccagtcatag caggggcgca gggcatgtg ttgcacaata  4200
tctttgagga ggagactgat ggccacgggc agcccttgg tgtaggtgtt tacaaatctg  4260
ttgagctggg agggatgcat gcgggggag atgaggtgca tcttggcctg gatcttgaga  4320
ttggcgatgt taccgcccag atcccgcctg gggttcatgt tgtgcaggac caccagcacg  4380
gtgtatccgg tgcacttggg gaatttatca tgcaacttgg aagggaaggc gtgaaagaat  4440
ttggcgacgc ctttgtgccc gcccaggttt tccatgcact catccatgat gatggcgatg  4500
ggcccgtggg cggcggcctg ggcaaagacg tttcggggt cggacacatc atagttgtgg  4560
tcctgggtga ggtcatcata ggccatttta atgaatttgg ggcggagggt gccggactgg  4620
gggacaaagg taccctcgat cccggggcg tagttcccct cacagatctg catctcccag  4680
gctttgagct cggaggggg gatcatgtcc acctgcggga cgataaagaa cacggttttcc  4740
ggggcggggg agatgagctg ggcgaaagc aagttccgga gcagctggga cttgccgcag  4800
ccggtggggc cgtagatgac cccgatgacc ggctgcaggt ggtagttgag ggagagacag  4860
ctgccgtcct cccggaggag ggggccacc tcgttcatca tctcgcgcac gtgcatgttc  4920
tcgcgcacca gttccgccag gaggcgctct cccccaggg ataggagctc ctggagcgag  4980
gcgaagttt tcagcggctt gagtccgtcg gccatgggca tttggagag ggtttgttgc  5040
aagagttcca ggcggtccca gagctcggtg atgtgctcta cggcatctcg atccagcaga  5100
cctcctcgtt tcgcgggttg ggacggctgc gggagtaggg caccagacga tgggcgtcca  5160
gcgcagccag ggtccggtcc ttccagggtc gcagcgtccg cgtcagggtg gtctccgtca  5220
cggtgaaggg gtgcgcgccg ggctgggcgc ttgcgagggt gcgcttcagg ctcatccggc  5280
tggtcgaaaa ccgctcccga tcggcgccct gcgcgtcggc caggtagcaa ttgaccatga  5340
gttcgtagtt gagcgcctcg gccgcgtggc cttggcgcg gagcttacct ttggaagtct  5400
gcccgcggc gggacagagg agggacttga gggcgtagag cttggggcg aggaagacgg  5460
actcgggggc gtaggcgtcc gcgccgcagt gggcgcagac ggtctcgcac tccacgagcc  5520
aggtgaggtc gggctggtcg gggtcaaaaa ccagtttccc gccgttcttt ttgatgcgtt  5580
tcttaccttt ggtctccatg agctcgtgtc cccgctgggg gacaaagagg ctgtccgtgt  5640
ccccgtagac cgactttatg ggccggttcct cgagcggtgt cgccggtcc tcctcgtaga  5700
ggaaccccgc ccactccgag acgaaagccc gggtccaggc cagcacgaag gaggccacgt  5760
gggacgggta gcgtcgttg tccaccagcg ggtccacctt ttccaggta tgcaaacaca  5820
tgtccccctc gtccacatcc aggaaggtga ttggcttgta agtgtaggcc acgtgaccgg  5880
gggtcccggc cggggggta taaaagggtg ccggtccctg ctcgtcctca ctgtcttccg  5940
gatcgctgtc caggagcgcc agctgttggg gtaggtattc cctctcgaag gcgggcatga  6000
cctcggcact caggttgtca gtttctagaa acgaggagga tttgatattg acggtgccgg  6060
cggagatgcc tttcaagagc ccctcgtcca tctggtcaga aaagacgatc tttttgttgt  6120
cgagcttggt ggcgaaggag ccgtagaggg cgttggaagg gagcttggcg atggagcgca  6180
tggtctggtt ttttttccttg tcggcgcgct ccttggcggc gatgttgagc tgcacgtact  6240
cgcgcgccac gcacttccat tcggggaaga cggtggtcag ctcgtcgggc acgattctga  6300
cctgccagcc ccgattatgc agggtgatga ggtccacact ggtggccacc tcgccgcgca  6360
ggggctcatt agtccagcag aggcgtccgc ccttgcgca gcaaagggg ggcagggggt  6420
ccagcatgac ctcgtcgggg ggtcggcat cgatgctgaa gatgccgagc aggaggtcgg  6480
ggtcaaagta gctgatggaa gtggccagat cgtccagggc agcttgccat tcgcgcacgg  6540
ccagcgcgcg ctcgtaggga ctgaggggcg tgccccaggg catgggatgg gtaagcgcgg  6600
aggcgtacat gccgcagatg tcgtagacgt agaggggctc ctcgaggatg ccgatgtagg  6660
tggggtagca gcgcccccg cggatgctgg cgcgcacgta gtcatacagc tcgtcgcagg  6720
gggcgaggag cccgggccc aggttggtgc gactgggctt ttcggcgcgg tagacgatct  6780
ggcggaaaat ggcatgcgag ttggaggaga tggtgggcct ttggaagatg ttgaagtggg  6840
cgtggggcag tccgaccgag tcgcggatga agtgggcgta ggagtcttgc agcttggcga  6900
cgagctcggc ggtgactagg acgtccagag cgcagtagtc gagggtctcc tggatgatgg  6960
catacttgag ctgtcccttt tgtttccaca gctcgcggtt gagaaggaac tcttcgcggt  7020
ccttccagta ctcttcgagg gggaacccgc cctgatctgc acgtaagag cctagcatgt  7080
agaactggtt gacggccttg taggcgcagc agcccttctc cacggggagg gcgtaggcct  7140
gggcggcctt gcgcagggag gtgtgcgtga gggcgaaagt gtccctgacc atgaccttga  7200
ggaactggtg cttgaagtcg atatcgtcgc agcccccctg ctcccagacc tggaagtccg  7260
tgcgcttctt gtaggcgggg ttgggcaaag cgaaagtaac atcgttgaag aggatctcgc  7320
ccgcgcgggg cataaagttg cgagtgatgc ggaaaggttg gggcacctcg gcccggttgt  7380
tgatgacctg ggcggcgagc acgatctcgt cgaagccgtt gatgttgtgg cccacgatgt  7440
agagttccac gaatcgcgga cggccttga cgtggggcag tttcttgagc tcctcgtagg  7500
tgagctgctg ggggtcgctg agccgtgct gctcgagcgc ccagtcggcg agatggggt  7560
tggcgcggag gaaggaagtc cagagatcca cggccaggc ggtttgcaga cggtcccggt  7620
actgacggaa ctgctgcccg acggccattt tttcggggt gacgcagtag aaggtgcggg  7680
ggtccccgtg ccagcgatcc catttgagct ggagggcgag atcgagggcg agctcgacga  7740
gccggtcgtc cccggagagt ttcatgacca gcatgaaggg gacgagctgc ttgccgaagg  7800
accccatcca ggtgtaggtt tccacatcgt aggtgaggaa gagcctttcg gtgcgaggat  7860
```

```
gcgagccgat ggggaagaac tggatctcct gccaccaatt ggaggaatgg ctgttgatgt    7920
gatgaagta gaaatgccga cggcgcgccg aacactcgtg cttgtgttta tacaagcggc    7980
cacagtgctc gcaacgctgc acgggatgca cgtgctgcac gagctgtacc tgagttcctt    8040
tgacgaggaa tttcagtggg aagtggagtc gtggcgcctg catctcgtgc tgtactacgt    8100
cgtggtggtc ggcctggccc tcttctgcct cgatggtggt catgctgacg agcccgcgcg    8160
ggaggcaggt ccagacctcg gcgcgagcgg gtcggagagc gaggacgagg gcgcgcaggc    8220
cggagctgtc cagggtcctg agacgctgcg gagtcaggtc agtgggcagc ggcggcgcgc    8280
ggttgacttg caggagtttt tccagggcgc gcgggaggtc cagatggtac ttgatctcca    8340
ccgcgccatt ggtggcgacg tcgatggctt gcagggtccc gtgccccggg ggtgtgacca    8400
ccgtccccg tttcttcttg ggcggctggg gcgacggggg cggtgcctct tccatggtta    8460
gaagcggcgg cgaggacgcg cgccgggcgg caggggcggc tcgggcccg gaggcagggg    8520
cggcaggggc acgtcggcgc cgcgcgcggg taggttctgg tactgcgccc ggagaagact    8580
ggcgtgagcg acgacgcgac ggttgacgtc ctggatctga cgcctctggg tgaaggccac    8640
gggacccgtg agtttgaacc tgaaagagag ttcgacagaa tcaatctgag tatcgttgac    8700
ggcggcctgc cgcaggatct cttgcacgtc gcccgagttg tcctggtagg cgatctcggg    8760
catgaactgc tcgatctcct cctcttgaag gtctccgcgg ccggcgcgct ccacggtggc    8820
cgcgaggtcg ttggagatgc ggcccatgag ctgcgagaag gcgttcatgc ccgcctcgtt    8880
ccagacgcgg ctgtagacca cgacgccctc gggatcgccg gcgcgcatga ccacctgggc    8940
gaggttgagc tccacgtggc gcgtgaagac cgcgtagttg cagaggcgct ggtagaggta    9000
gttgagcgtg tgggcgatgt gctcggtgac gaagaaatac atgatccagc ggcggagcgg    9060
catctcgctg acgtcgccca gcgcctccaa acgttccatg gcctcgtaaa agtccacggc    9120
gaagttgaaa aactgggagt tgcgcgccga gacggtcaaa tcctcctcca gaagacggat    9180
gagctcggcg atggtggcgc gcacctcgcg ctcgaaggcc ccgggagtt cctccacttc    9240
ctcttcttcc tcctccacta acatctcttc tacttcctcc tcaggcggca gtggtggcgg    9300
gggagggggc ctgcgtcgcc ggcggcgcac gggcagacgg tcgatgaagc gctcgatggt    9360
ctcgccgccg cggcgtcgca tggtctcggt gacggccgcc ccgtcctcgc ggggccgcag    9420
cgtgaagacg ccgccgcgca tctccaggtg gccggggggg tccccgttgg gcagggagag    9480
ggcgctgacg atgcatctta tcaattgccc cgtagggact ccgcgcaagg acctgagcgt    9540
ctcgagatcc acgggatctg aaaaccgctg aacgaaggct tcgagccagt cgcagtcgca    9600
aggtaggctg agcacggttt cttctgcgg gtcatgttgg ttgggagggg ggcgggcgat    9660
gctgctggtg atgaagttga aataggcggt tctgagacgg cggatggtgg cgaggagcac    9720
caggtctttg ggcccggctt gctggatgcg cagacggtcg gccatgcccc aggcgtggtc    9780
ctgacacctg gccaggtcct tgtagtagtc ctgcatgagc cgctccacgg gcacctcctc    9840
ctcgcccgcg cggccgtgca tgcgcgtgag cccgaagccg cgctggggct ggacgagcgc    9900
caggtcggcg acgacgcgct cggcgaggat ggcttgctgg atctgggtga gggtggtctg    9960
gaagtcatca aagtcgacga agcggtggta ggctccggtg ttgatggtgt aggagcagtt   10020
ggccatgacg gaccagttga cggtctggtg gcccggacgc acgagctcgt ggtacttgag   10080
gcgcgagtag gcgcgcgtgt cgaagatgta gtcgttgcag gtgcgcacca ggtactggta   10140
gccgatgagg aagtgcggcg gcggctggcg gtagagccgc catcgctcgg tggcggggcg   10200
gccgggcgcg aggtcctcga gcatggtgcg gtggtagccg tagatgtacc tggacatcca   10260
ggtgatgccg gcggcggtgg tggaggcgcg cgggaactcg cggacgcggt tccagatgtt   10320
gcgcagcggc aggaagtagt tcatggtggg cacggtctgg cccgtgaggc gcgcgcagtc   10380
gtggatgctc tatacgggca aaaacgaaag cggtcagcgg ctcgactccg tggcctggta   10440
gctaagcgaa cgggttgggc tgcgcgtgta ccccggttcg aatctcgaat caggctggag   10500
ccgcagctaa cgtggtattg gcactcccgt ctcgacccaa gcctgcacca accctccagg   10560
atacggaggc gggtcgtttt gcaactttt tttggaggcc ggatgagact agtaagcgcg   10620
gaaagccgcg gaccgcgatg gctcgctgcc gtagtctgga gaagaatcgc caggggttgcg   10680
ttgcggtgtg ccccggttcg aggccggccg gattccgcgg ctaacagggg cgtggctgcc   10740
ccgtcgtttc caagacccca tagccagccg acttctccag ttacggagcg agccctctt   10800
ttgttttgtt tgttttgcc agatgcatcc cgtactgcgg cagatgcgcc cccaccaccc   10860
tccaccgcaa caacagcccc ctccacagcc ggcgcttctg cccccgcccc agcagcaact   10920
tccagccacg accgccgcgg ccgccgtgag cggggctgga cagagttatg atcaccagct   10980
ggccttggaa gagggcgagg ggctggcgcg cctgggggcg tcgtcgcgg agcggcaccc   11040
gcgcgtgcag atgaaaaggg acgctcgcga ggcctacgtg cccaagcaga acctgttcag   11100
agacaggagc ggcgaggagc ccgaggagat gcgcgcgccc cggttccacg cggggcggga   11160
gctgcggcgc ggcctggacc gaaagagggt gctgagggac gaggatttcg aggcggacga   11220
gctgacgggg atcagccccg cgcgcgcgca cgtggccgcg gccaacctgg tcacggcgta   11280
cgagcagacc gtgaaggagg agagcaactt ccaaaaatcc ttcaacaacc acgtgcgcac   11340
cctgatcgcg cgcgaggagg tgaccctggg cctgatgcac ctgtgggagc tgctggaggc   11400
catctgcag aaccccacca gcaagccgct gacggcgcac ctgttcctgg tggtgcagca   11460
tagtcgggac aacgaagcgt tcaggaggc gctgctgaat atcaccgagc ccgagggccg   11520
ctggctcctg gacctggtga acattctgca gagcatcgtg gtgcaggagc gcgggctgcc   11580
gctgtccgag aagctggcgg ccatcaactt ctcggtgctg agtttgggca agtactacgc   11640
taggaagatc tacaagaccc cgtacgtgcc catagacaga tcgacggggtt   11700
ttacatcgcg atgaccctga aagtgctgac cctgagcgac gatctggggg tgtaccgcaa   11760
cgacaggatg caccgtgcgg tgagcgccag caggcggcgc gagctgagcg accaggagct   11820
gatgcatagt ctgcagcggg ccctgaccgg ggccgggacc gaggggggaga gctactttga   11880
catgggcgcg gacctgcact ggcagcccag ccgccgggcc ttggaggcgg cggcaggacc   11940
ctacgtagaa gaggtggacg atgaggtgga cgaggagggc gagtacctgg aagactgagg   12000
gcgcgaccgt attttgcta gatgcaacaa caacagccac ctcctgatcc cgcgatgcgg   12060
gcgcgcgctgc agagccagcc gtccggcatt aactcctcgg acgattggac ccaggccatg   12120
caacgcatca tggcgctgac gacccgcaac cccgaagcct ttagacagca gccccaggcc   12180
aaccggctct cggccatcct ggaggccgtg gtgccctcgc gctccaaccc cacgcacgag   12240
aaggtcctgg ccatcgtgaa cgcctcggtg gagaacaagg ccatccgcgg cgacgaggtc   12300
ggcctggtgt acaacgcgct gctggagcgc gtggcccgct acaacagcac caacgtgcag   12360
accaacctgg accgcatggt gaccgacgtg cgcgaggcc tgcccagcg cgagcggttc   12420
caccgcgagt ccaacctggg atccatggtg gcgctgaacg ccttcctcag cacccagccc   12480
gccaacgtgc ccggggcca ggaggactac accaacttca tcagcgccct cgcctgatgt   12540
gtgaccgagg tgcccagag cgaggtgtac cagtccgggc cggactactt cttccagacc   12600
```

```
agtcgccagg gcttgcagac cgtgaacctg agccaggctt tcaagaactt gcagggcctg    12660
tggggcgtgc aggccccggt cggggaccgc gcgacggtgt cgagcctgct gacgccgaac    12720
tcgcgcctgc tgctgctgct ggtggccccc ttcacggaca gcggcagcat caaccgcaac    12780
tcgtacctgg gctacctgat taacctgtac cgcgaggcca tcggccaggc gcacgtggac    12840
gagcagacct accaggagat caccccacgtg agccgcgccc tgggccagga cgacccgggc    12900
aacctggaag ccaccctgaa cttttttgctg accaaccggt cgcagaagat cccgccccag    12960
tacgcgctca gcaccgagga ggagcgcatc ctgcgttacg tgcagcagag cgtgggcctg    13020
ttcctgatgc aggaggggc caccccagc gccgcgctcg acatgaccgc gcgcaacatg    13080
gagccagca tgtacgccag caaccgcccg ttcatcaata aactgatgga ctacttgcat    13140
cgggcggccg ccatgaactc tgactatttc accaacgcca tcctgaatcc ccactggctc    13200
ccgccgccgg ggttctacac gggcgagtac gacatgcccg accccaatga cgggttcctg    13260
tgggacgatg tggacagcag cgtgttctcc ccccgaccgg gtgctaacga cgcccccttg    13320
tggaagaagg aaggcagcga ccgacgcccg tcctcggcgc tgtccggccg cgagggtgct    13380
gccgcggccg tgcccgaggc cgccagtcct ttcccgagct tgcccttctc gctgaacagt    13440
atccgcagca gcgagctggg caggatcacg cgcccgcctt tgctgggcga agaggagtac    13500
ttgaatgact cgctgttgag acccgagcgg gagaagaact tccccaataa cgggatagaa    13560
agcctggtgg acaagatgag ccgctggaag acgtatgcgc aggagcacag ggacgatccc    13620
cgggcgtcgc aggggccac gagccgggc agcgccgcc gtaaacgccg gtggcacgac    13680
aggcagcggg gacagatgtg ggacgatgag gactccgccg acgacagcca cgtgttggac    13740
ttgggtggga gtggtaaccc gttcgctcac ctgcgccccc gtatcgggcg catgatgtaa    13800
gagaaaccga aaataaatga tactcaccaa ggccatggcg accagcgtgc gttcgtttct    13860
tctctgttgt tgttgtatct agtatgatga ggcgtgcgta cccggaggt cctcctccct    13920
cgtacgagag cgtgatgcag caggcgatgg cggcggcggc gatgcagccc cgctggaggg    13980
ctccttacgt gccccgcgg tacctggcgc ctacggaggg gcgggaacagc attcgttact    14040
cggagctggc acccttgtac gataccaccc ggttgtacct ggtggacaac aagtcggcgg    14100
acatccgcct gctgaactac cagaacgacc acagcaactt cctgaccacc gtggtgcaga    14160
acaatgactt caccccacg gaggccagca cccagaccat caactttgac gagcgctcg    14220
ggtgggcgg ccagctgaa accatcatgc acaccaacat gccccaacgtg aacgagttca    14280
tgtacagcaa caagttcaag gcgcgggtga tggtctcccg caagaccccc aatgggtga    14340
cagtgacaga ggattatgat ggtagtcagg atgagctgaa gtatgaatgg gtggaatttg    14400
agctgcccga aggcaacttc tcggtgacca tgaccatcga cctgatgaac aacgccatca    14460
tcgacaatta cttggcggtg gggcggcaga acggggtgct ggagagcgac atcggcgtga    14520
agttcgacac taggaacttc aggctgggct gggacccgt gaccgagctg gtcatgcccg    14580
gggtgtacac caacgaggct ttccatcccg atattgtctt gctgcccggc tgcgggtgg    14640
acttcaccga gagccgcctc agcaacctgc tgggcattcg caagaggcag ccctttccagg    14700
aaggcttcca gatcatgtac gaggatctgg aggggggcaa catccccgcg ctcctggatg    14760
tcgacgccta tgagaaaagc aaggaggatg cagcagctga agcaactgca gccgtagcta    14820
ccgcctctac cgaggtcagg ggcgataatt ttgcaagcgc cgcagcagtg gcagcggccg    14880
aggcgctga aaccgaaagt aagatagtca ttcagccggt ggagaaggt agcaagaaca    14940
ggagctacaa cgtactaccg gacaagataa acaccgccta ccgcagctgg tacctagcct    15000
acaactatgg cgaccccgag aagggcgtgc gctcctggac gctgctcacc acctcggacg    15060
tcacctgcgg cgtggagcaa gtctactggt cgctgcccga catgatgcaa gacccggtca    15120
ccttccgctc cacgcgtcaa gttagcaact acccggtggt ggccgcgagg tcctgccncg    15180
tctactccaa gagcttcttc aacgagcagg ccgtctactc gcagcagctg cgcgccttca    15240
cctgcttac gcacgtcttc aaccgcttcc ccgagaacca gatcctcgtc cgcccgcccg    15300
cgcccaccat taccaccgtc agtgaaaacg ttcctgctct cacagatcac gggacccgtc    15360
cgctgcgcag cagtatccgg ggagtccagc gcgtgaccgt tactgacgcc acgaccgcg    15420
cctgccccta cgtctacaag gccctggga tagtcgcgcc gcgcgtcctc tcgagccgca    15480
ccttctaaat gtccattctc atctcgccca gtaataacac cggttggggc ctgcgcgcgc    15540
ccagcaagat gtacggaggc gctcgccaac gctccacgca caccccgtg cgcgtgcgcg    15600
ggcacttccg cgctccctgg ggcgccctca agggccgcgt tcggtcgcgc accaccgtcg    15660
acgacgtgat cgaccaggtg gtgaccgacg cgcgcaacta cacccccgcc gccgcgcccg    15720
tctccaccgt ggacgccgtc atcgacacgc tggtggcgga cgcgcgcggg tacgcccgcg    15780
ccaagagccg gcgcggcgc atcgcccggc ggcaccggag cacccccgcc atgcgcgcgg    15840
cgcgagcctt gctgcgcagg gccaggccca cgggacgcag ggcgcggcca agggcggcca    15900
gacgcgcggc ttcaggcgcc agcgccggca ggaccccggag acgcgcgcc acggcggcgg    15960
cagcggcat cgccagcatg tcccccccgc ggcgagggaa cgtgtactgg gtgcgcgacg    16020
ccgccaccgg tgtgcgcgtg cccgtgcgca cccgccccc tcgcacttga agatgttcac    16080
ttcgcgatgt tgatgtgtcc cagcgcgag gaggatgtcc aagcgcaaat tcaaggaaga    16140
gatgctccag gtcatcgcgc ctgagatcta cggccctgcg gtggtgaagg aggaaagaaa    16200
gccccgcaaa atcaagcggg tcaaaaagga caaaaaggaa gaagaaagtg atgtggacgg    16260
attggtggaa tttgtgcgcg agttcgcccc cggcggcgc gtgcagtggc gcgggcggaa    16320
ggtgcaaccg gtgctgagac ccggcaccac cgtggtcttc acgcccggcg agcgctccgg    16380
caccgcttcc aagcgctcct acgacgaggt gtacgggat gatgatattc tggagcgcag    16440
ggccgagcgc ctgggcgagt ttgcttacgg caagcgcagc cgttccgcac cgaaggagga    16500
ggcggtgtcc atcccgctgg accacggcaa ccccacgccg agcctcaagc ccgtgacctt    16560
gcagcaggtg ctgccgaccg cggcgccgcg ccggggttc aagcgcgagg gcgaggatct    16620
gtaccccacc atgcagctga tggtgcccaa gcgccagaag ctggaagacg tgctggagac    16680
catgaaggtg gaccggacg tgcagcccga ggtcaaggtg cggcccatca agcaggtgga    16740
cccgggcctg gcgtgcaga ccgtggacat caagattccc acggagccca tggaaacgca    16800
gaccgagccc atgatcaagc ccagcaccag caccatggag gtgcagacgg atccctggat    16860
gccatcggct cctagtcgaa gaccccgcg caagtacggc gcggccagcc tgctgatgcc    16920
caactacgcg ctgcatcctt ccatcatccc cacgccgggc taccgcggca cgcgcttcta    16980
ccgtgcat accagcagcc gccgccgaa gaccaccact cgcaccactc cgccgcccac    17040
cgccgctgca accaccccctg ccgcctggt gcggagagtg taccgccgcg gccgcgcacc    17100
tctgaccctg ccgcgcgcgc gctaccaccc gagcatcgcc atttaaactt tcgccagctt    17160
tgcagatcaa tggccctcac atgccgcctt gcgttcca ttacgggcta ccgaggaaga    17220
aaaccgcgcc gtagaaggct ggcggggaac gggatgcgtc gccaccacca ccggcggcgg    17280
cgcgccatca gcaagcggtt ggggggaggc ttcctgcccg cgctgatccc catcatcgcc    17340
```

```
gcggcgatcg gggcgatccc cggcattgct tccgtggcgg tgcaggcctc tcagcgccac  17400
tgagacacac ttggaaacat cttgtaataa acccatggac tctgacgctc ctggtcctgt  17460
gatgtgtttt cgtagacaga tggaagacat caatttttcg tccctggctc cgcgacacgg  17520
cacgcggccg ttcatgggca cctggagcga catcggcacc agccaactga acggggggcgc  17580
cttcaattgg agcagtctct ggagcgggct taagaatttc gggtccacgc ttaaaaccta  17640
tggcagcaag gcgtggaaca gcaccacagg gcaggcgctg agggataagc tgaaagagca  17700
gaacttccag cagaaggtgg tcgatgggct cgcctcgggc atcaacgggg tggtggacct  17760
ggccaaccag gccgtgcagc ggcagatcaa cagccgcctg acccggtgc cgcccgccgg  17820
ctccgtggag atgccgcagg tggaggagga gctgcctccc ctgacaagc ggggcgagaa  17880
gcgacccgc cccgatgcgg aggagacgct gctgacgcac acggacgagc cgccccgta  17940
cgaggaggcg gtgaaactgg gtctgcccac cacgcggccc atcgcgcccc tggccaccgg  18000
ggtgctgaaa cccgaaaagc ccgcgaccct ggacttgcct cctccccagc cttcccgccc  18060
ctctacagtg gctaagcccc tgccgccggt ggccgtggcc cgcgcgcgac ccgggggcac  18120
cgcccgccct catgcgaact ggcagagcac tctgaacagc atcgtgggtc tgggagtgca  18180
gagtgtgaag cgccgccgct gctattaaac ctaccgtagc gcttaacttg cttgtctgtg  18240
tgtgtatgta ttatgtcgcc gccgccgctg tccaccagaa ggaggagtga agaggcgcgt  18300
cgccgagttg caagatggcc acccccatcga tgctgcccca gtgggcgtac atgcacatcg  18360
ccggacagga cgcttcggag tacctgagtc cgggtctggt gcagtttgcc cgcgccacag  18420
acacctactt cagtctgggg aacaagttta ggaaccccac ggtggcgccc acgcacgatg  18480
tgaccaccga ccgcagccag cggctgacgc tgccgcttcgt gcccgtggac cgcgaggaca  18540
acacctactc gtacaaagtg cgctacacgc tggccgtggg cgacaaccgc gtgctggaca  18600
tggccagcac ctactttgac atccgcggcg tgctggatcg gggccctagc ttcaaaccct  18660
actccggcac cgcctacaac agtctggccc ccaaggagc acccaacact tgtcagtgga  18720
catataaagc cgatggtgaa actgccacag aaaaaaccta tacatatgga aatgcacccg  18780
tgcagggcat taacatcaca aaagatggta ttcaacttgg aactgacacc gatgatcagc  18840
caatctacgc agataaaacc tatcagcctg aacctacagc gggtgatgct gaatggcatg  18900
acatcactgg tactgatgaa aagtatggag gcagagctct taagcctgat accaaaatga  18960
agccttgtta tggttctttt gccaagccta ctaataaaga aggaggtcag gcaaatgtga  19020
aaacaggaac aggcactact aaagaatatg acatagacat ggctttcttt gacaacagaa  19080
gtgcggctgc tgctggccta gctccagaaa ttgttttgta tactgaaaat gtggatttgg  19140
aaactccaga tacccatatt gtatacaaag caggcacaga tgacagcagc tcttctatta  19200
atttgggtca gcaagccatg cccaacagac ctaactacat tggtttcaga gacaacttta  19260
tcggggctcat gtactacaac agcactggca atatgggggt gctggccggt caggcttctc  19320
agctgaatgc tgtggttgac ttgcaagaca gaaacaccga gctgtcctac cagctcttgc  19380
ttgactctct gggtgacaga accggtatt tcagtatgtg gaatcaggcg gtggacagct  19440
atgatcctga tgtgcgcatt attgaaaatc atggtgtgga ggatgaactt cccaactatt  19500
gtttccctct ggatgctgtt ggcagaacag atacttatca gggaattaag gctaatggaa  19560
ctgatcaaac cacatggacc aaagatgaca gtgtcaatga tgctaatgag ataggcaagg  19620
gtaatccatt cgccatggaa atcaacatcc aagccaacct gtggaggaac ttcctctaca  19680
ccaacgtggc cctgtacctg cccgactctt acaagtacac gccggccaat gttaccctgc  19740
ccaccaacac caacacctac gattacatga acggccgggt ggtggcgccc tcgctggtgg  19800
actcctacat caacatcggg gcgcgctggt cgctggatcc catggacaac gtgaacccct  19860
tcaaccacca ccgcaatgcg gggctgcgct accgctccat cctctgggc aacgggcgct  19920
acgtgccctt ccacatccag gtgccccaga aatttttcgc catcaagagc ctcctgctcc  19980
tgcccgggtc ctacacctac gagtggaact tccgcaagga cgtcaacatg atcctgcaga  20040
gctccctcgg caacgacctg cgcacggacg gggcctccat ctccttcacc agcatcaacc  20100
tctacgccac cttcttcccc atggcgcaca acacggcctc cacgctcgag gccatgctgc  20160
gcaacgacac caacgaccag tccttcaacg actacctctc ggcggccaac atgctctacc  20220
ccatcccggc caacgccacc aacgtgccca tctccatccc ctcgcgcaac tgggccgcct  20280
tccgcggctg gtccttcacg cgtctcaaga ccaaggagc gccctcgctg ggctccgggt  20340
tcgaccccta cttcgtctac tcgggctcca tccccctacg gcacggcacc ttctaccctca  20400
accacacctt caagaaggtc tccatcacct tcgactcctc cgtcagctgg cccggcaacg  20460
accggctcct gacgcccaac gagttcgaaa tcaagcgcac cgtcgacggc gagggctaca  20520
acgtggccca gtcaacatg accaaggact ggttcctggt ccagatgctg gcccactaca  20580
acatcggcta ccagggcttc tacgtgcccg agggctacaa ggaccgcatg tactccttct  20640
tccgcaactt ccagcccatg agccgccagg tggtgacaa ggtcaactac aaggactacc  20700
aggcctcac cctggcctac cagcacaaca actcgggctt cgtcggctac ctcgcgccca  20760
ccatgcgcca gggccagccc tacccgcca actacccta cccgctcatc ggcaagagcg  20820
ccgtcacca gtcacccag aaaaagttcc tctgcgacag ggtcatgtgg cgcatcccct  20880
tctccagcaa cttcatgtcc atgggcgcgc tcaccgacct cggccagaac atgctctatg  20940
ccaactccgc ccacgcgcta gacatgaatt tcgaagtcga ccccatggat gagtccaccc  21000
ttctctatgt tgtcttcgaa gtcttcgacg tcgtccgagt gcaccagccc caccgcggcg  21060
tcatcgagc cgtctacctg cgcaccccct tctcggccgg taacgccacc acctaagctc  21120
ttgcttcttg caagccatgg ccgcggggctc cggcgagcag gagctcaggg ccatcatccg  21180
cgacctgggc tgcgggccct acttcctggg caccttcgat aagcgcttcc ggggattcat  21240
ggccccgcac aagctggcct gcgccatcgt caacacggcc ggccgcgaga ccgggggcga  21300
gcactggctg gccttcgcct ggaacccgcg ctcgaacacc tgctacctct tcgaccccttt  21360
cggggttctcg gacgagcgcc tcaagcagat ctaccagttc gagtacgagg gctgctgcg  21420
ccgcagccgc ctggccaccg aggacgctg cgtcacccotg gaaaagtcca cccagacccg  21480
gcagggtccg cgctcggccg cctgcgggct cttctgctgc atgttcctgc acgccttcgt  21540
gcactggccc gaccgcccca tggacaagaa ccccaccatg aacttgctga cggggggtgcc  21600
caacggcatg ctccagtcgc cccaggtgga acccaccctg cgccgcaacc aggaggcgct  21660
ctaccgcttc ctcaactccc actccgccta ctttcgctcc caccgcgcgc gcatcgagaa  21720
ggccaccgcc ttcaccgca tgaatcaaga catgtaaacc gtgtgtgtat gttaaatgtc  21780
tttaataaac agcactttca tgttacacat gcatctgaga tgatttatttt agaaatcgaa  21840
agggttctgc cgggtctcgg catgcccgc gggcagggac acgttgcgga actggtactt  21900
ggccagccac ttgaactcgg ggatcagcag tttgggcagc ggggtgtcgg ggaaggagtc  21960
ggtccacagc ttccgcgtca gttgcagggc gcccagcagg tcgggcgcgg agatcttgaa  22020
atcgcagttg ggaccgcgt tctgcgcgcg ggagttgcgg tacacggggt tgcagcactg  22080
```

```
gaacaccatc agggccgggt gcttcacgct cgccagcacc gtcgcgtcgg tgatgctctc   22140
cacgtcgagg tcctcggcgt tggccatccc gaaggggtc atcttgcagg tctgccttcc    22200
catggtgggc acgcacccgg gcttgtggtt gcaatcgcag tgcaggggga tcagcatcat   22260
ctgggcctgc tcggcgttca tccccgggta catggccttc atgaaagcct ccaattgcct   22320
gaacgcctgc tgggccttgc ctccctcggt gaagaagacc ccgcaggact tgctagagaa   22380
ctggttggtg gcgcacccgg cgtcgtgcac gcagcagcgc gcgtcgttgt tggccagctg   22440
caccacgctg cgccccagc ggttctgggt gatcttggcc cggtcggggt tctccttcag    22500
cgcgcgctgc ccgttctcgc tcgccacatc catctcgatc atgtgctcct tctggatcat   22560
ggtggtcccg tgcaggcacc gcagcttgcc ctcggcctcg gtgcaccgt gcagccacag    22620
cgcgcacccg gtgcactccc agttcttgtg ggcgatctgg gaatgcgcgt gcacgaagcc   22680
ctgcaggaag cggccatca tggtggtcag ggtcttgttg ctagtgaagg tcagcggaat    22740
gccgcggtgc tcctcgttga tgtacaggtg gcagatgcgg cggtacacct cgccctgctc   22800
gggcatcagc tggaagttgg cttcaggtc ggtctccacg cggtagcggt ccatcagcat    22860
agtcatgatt tccataccct tctcccaggc cgagacgatg gcaggctca tagggttctt    22920
caccatcatc ttagcgctag cagccgcggc cagggggtcg ctctcgtcca gggtctcaaa   22980
gctccgcttg ccgtccttct cggtgatccg caccgggggg tagctgaagc ccacggccgc   23040
cagctcctcc tcggcctgtc tttcgtcctc gctgtcctgg ctgacgtcct gcaggaccac   23100
atgcttggtc ttgcggggtt tcttcttggg cggcagcggc ggcggagatg ttggagatgg   23160
cgaggggggag cgcgagttct cgctcaccac tactatctct tcctcttctt ggtccgaggc   23220
cacgcggcgg taggtatgtc tcttcggggg cagaggcgga ggcgacgggc tctgccgcc    23280
gcgacttggc ggatggctgg cagagcccct tccgcgttcg ggggtgcgct cccggcggcg   23340
ctctgactga cttcctccgc ggccggccat tgtgttctct tagggaggaa caacaagcat   23400
ggagactcag ccatcgccaa cctcgccatc tgccccccacc gccgacgaga agcagcagca   23460
gcagaatgaa agcttaaccg ccccgccgcc cagccccgcc acctccgacg cggccgtccc   23520
agacatgcaa gagatggagg aatccatcga gattgacctg ggctatgtga cgcccgcgga   23580
gcacgaggag gagctggcag tgcgcttttc acaagaagag atacaccaag aacagccaga   23640
gcaggaagca gagaatgagc agagtcaggc tgggctcgag catgacgcg actacctcca    23700
cctgagcggg gggaggacg cgctcatcaa gcatctggcc cggcaggcca ccatcgtcaa    23760
ggatgcgctg ctcgaccgca ccgaggtgcc cctcagcgtg gaggagctca gccgcgccta   23820
cgagttgaac ctcttctcgc cgcgcgtgcc ccccaagcgc cagcccaatg cacctgcgg    23880
gcccaacccg cgcctcaact tctaccggt cttcgcggtg cccgaggccc tggccaccta    23940
ccacatcttt ttcaagaacc aaaagatccc cgtctcctgc cgcgccaacc gcacccgcgc   24000
cgacgccctt ttcaacctgg gtcccggcgc ccgcctacct gatatcgcct ccttggaaga   24060
ggttcccaag atcttcgagg gtctgggcag cgacgagact ccgggccgcga acgctctgca   24120
aggagaagga ggagacatg agcaccacag cgccctggtc gagttggaag gcgacaacgc   24180
gcggctggcg gtgctcaaac gcacggtcga gctgacccat ttcgcctacc cggctctgaa   24240
cctgccccc aaagtcatga gcgcggtcat ggaccaggtg ctcatcaagc gcgcgtcgcc    24300
catctccgag gacgagggca tgcaagactc cgaggagggc aagcccgtgg tcagcgacga   24360
gcagctggcc cggtggctgg gtcctaatgc tagtccccag agtttggaag agcggccgaa   24420
actcatgatg gccgtggtcc tggtgaccgt ggagctggag tgcctgcgcc gcttcttcgc   24480
cgacgcggag accctgcgca aggtcgagga gaacctgcac tacctcttca ggcacgggtt   24540
cgtgcgccag gcctgcaaga tctccaacgt ggagctgacc aacctggtct cctacatggg   24600
catcttgcac gagaaccgcc tggggcagaa cgtgctgcac accaccctgc gcggggaggc   24660
ccggcgcgac tacatccgcg actgcgtcta cctctaccgc tgccacacct ggcagacggg   24720
catgggcgtg tggcagcagt gtctggagga gcagaacctg aaagagctct gcaagctcct   24780
gcagaagaac ctcaagggtc tgtggaccgg gttcgacgag cgcaccaccg cctcggacct   24840
ggccgacctc attttccccg agcgcctcag gctgacgctg gcaacggcc tgcccgactt    24900
tatgagccaa agcatgttgc aaaactttcg ctctttcatc ctcgaacgcc ccggaatcct   24960
gcccgccacc tgctccgcgc tgccctcgga ctttgtgccg ctgaccttcc gcgagtgccc   25020
cccgccgctg tggagccact gctacctgct gcgcctggcc aactacctgg cctaccactc   25080
ggacgtgatc gaggacgtca gcggcgaggg cctgctcgga tgccactgcc gctgcaacct   25140
ctgcacgccg caccgctccc tggcctgcaa cccccagctg ctgagcgaga cccagatcat   25200
cggcaccttc gagttgcaag ggccagcga aggcgaggt tcagccgcca ggggggtct     25260
gaaactcacc ccggggctgt ggacctcggc ctacttgcgc aagttcgtgc ccgaggacta   25320
ccatccctc gagatcaggt tctacgagga ccaatcccat ccgcccaagg ccgagctgtc    25380
ggcctgcgtc atcacccagg gggcgatcct ggcccaattg caagccatcc agaaatcccg   25440
ccaagaattc ttgctgaaaa agggccgcgg ggtctacctc gacccccaga ccggtgagga   25500
gctcaacccc ggcttccccc aggatgcccc gaggaaacaa gaagctgaaa gtggagctgc   25560
cgcccgtgga ggatttggag gaagactggg agaacagcag tcaggcagag gaggaggaga   25620
tgaggaaga ctgggacacg actcaggcag aggaggacag cctgcaagac agtctggagg    25680
aagacgagga ggaggcagag gaggaggtgg aagaagcagc cgccgccaga ccgtcgtcct   25740
cggcggggga gaaagcaagc agcacggata ccatctccgc tccgggtcgg ggtcccgctc   25800
gaccacacag tagatgggac gagaccggac gattcccgaa ccccaccacc cagaccggta   25860
agaaggacg gcagggatac aagtcctggc ggggggcacaa aaacgccatc gtctccctgct   25920
tgcaggcctg cgggggcaac atctccttca cccggcgcta cctgctcttc caccgcgggg   25980
tgaactttcc ccgcaacatc ttgcattact accgtcacct ccacagcccc tactacttcc   26040
aagaagaggc agcagcagca gaaaagacc agcagaaaac cagcagctag aaaatccaca    26100
gcggcggcag caggtggact gaggatcgcg gcgaacgagc cggccgcaaac ccgggagctg   26160
aggaaccgca tcttttcccac cctctatgcc atcttccagc agagtcgggg gcaggagcga   26220
gaactgaaag tcaagaaccg ttctctgcgc tcgctcaccc gcagttgtct gtatcacaag   26280
agcgaagacc aacttcagcg cactctcgag gacgccgagg ctctctttcaa caagtactgc   26340
gcgctcactc ttaaagagta gcccgcgccc gccagtcgc agaaaaggc gggaattacg     26400
tcacctgtgc ccttcgccct agccgcctcc acccatcatc atgagcaaag agattccac    26460
gccttacatg tggagctacc agccccagat gggcctgcct gccaggacta                26520
ctccacccgg atgaattggc tcagcgccgg gccgcgatg atctcacggg tgaatgacat    26580
ccgcgcccac cgaaaccaga tactcctaga acagtcagcg ctaccgcca cgccccgcaa    26640
tcacctcaat ccgcgtaatt ggccgccgc cctggtgtac caggaaattc cccagcccac     26700
gaccgtacta cttccgcgag acgccaggc cgaagtccag ctgactaact caggtgtcca    26760
gctggcgggc ggcgccacc tgtgtcgtca ccgccccgct cagggtataa agcggctggt    26820
```

```
gatccggggc agaggcacac agctcaacga cgaggtggtg agctcttcgc tgggtctgcg   26880
acctgacgga gtcttccaac tcgccggatc ggggagatct tccttcacgc ctcgtcaggc   26940
cgtcctgact ttggagagtt cgtcctcgca gccccgctcg ggtggcatcg gcactctcca   27000
gttcgtggag gagttcactc cctcggtcta cttcaacccc ttctccggct cccccggcca   27060
ctacccggac gagttcatcc cgaacttcga cgccatcagc gagtcggtgg acggctacga   27120
ttgaatgtcc catggtggcg cagctgacct agctcggctt cgacacctgg accactgccg   27180
ccgcttccgc tgcttcgctc gggatctcgc cgagtttgcc tactttgagc tgcccgagga   27240
gcaccctcag ggcccggccc acggagtgcg gatcgtcgtc gaaggggggcc tcgactccca   27300
cctgcttcgg atcttcagcc agcgtccgat cctggtcgag cgcgagcaag gacagacccct   27360
tctgactctg tactgcatct gcaaccaccc cggcctgcat gaaagtcttt gttgtctgct   27420
gtgtactgag tataataaaa gctgagatca gcgactactc cggacttccg tgtgttcctg   27480
aatccatcaa ccagtctttg ttcttcaccg ggaacgagac cgagctccag ctccagtgta   27540
agccccacaa gaagtacctc acctggctgt tccagggctc cccgatcgcc gttgtcaacc   27600
actgcgacaa cgacggagtc ctgctgagcg gccctgccaa ccttacttt tccaccccgca   27660
gaagcaagct ccagctcttc caaccccttcc tccccgggac ctatcagtgc gtctcgggac   27720
cctgccatca caccttccac ctgatcccga ataccacagc gtcgctcccc gctactaaca   27780
accaaactaa cctccaccaa cgccaccgtc gcgaccttc tgaatctaat actaccaccc   27840
acaccggagg tgagctccga ggtcaaccaa cctctgggat ttactacggc ccctgggagg   27900
tggttgggtt aatagcgcta ggcctagttc cgggtgggct tttggttctc tgctacctat   27960
acctcccttg ctgttcgtac ttagtggtgc tgtgttgctg gttaagaaa tggggaagat   28020
caccctagtg agctgcggtg cgctggtggc ggtgttgctt tcgattgtgg gactgggcgg   28080
tgcggctgta gtgaaggaga aggccgatcc ctgcttgcat ttcaatccca acaaatgcca   28140
gctgagtttt cagcccgatg gcaatccggtg cgcggtactg atcaagtgcg gatgggaatg   28200
cgagaacgtg agaatcgagt acaataacaa gactcggaac aatactctcg cgtccgtgtg   28260
gcagcccggg gaccccgagt ggtacaccgt ctctgtcccc ggtgctgacg gctccccgcg   28320
caccgtgaat aatactttca tttttgcgca catgtgcgac acggtcatgt ggatgagcaa   28380
gcagtacgat atgtgccccc cacgaagga gaacatcgtg gtcttctcca tcgcttacag   28440
cctgtgcacg gcgctaatca ccgctatcgt gtgcctgagc attcacatgc tcatcgctat   28500
tcgcccccaga aataatgccg aaaaagaaaa acagccataa cgttttttttt cacacctttt   28560
tcagaccatg gcctctgtta aatttttgct tttatttgcc agtctcattg ccgtcattca   28620
tggaatgagt aatgagaaaa ttactattta cactggcact aatcacacat tgaaaggtcc   28680
agaaaaagcc acagaagttt catggtattg ttatttttaat gaatcagatg tatctactga   28740
actctgtgga aacaataaca aaaaaaatga gagcattact ctcatcaagt ttcaatgtgg   28800
atctgactta accctaatta acatcactag agactatgat ggtatgtatt atggaactac   28860
agcaggcatt tcggacatgg aattttatca agtttctgtg tctgaaccca ccacgcctag   28920
aatgaccaca accacaaaaa ctacacctgt taccactatg cagctcacta ccaataacat   28980
ttttgccatg cgtcaaatgg tcaacaatag cactcaaccc accccaccca gtgaggaaat   29040
tcccaaatcc atgattggca ttattgttgc tgtagtggtg tgcatgttga tcatcgcctt   29100
gtgcatggtg tactatgcct tctgctacag aaagcacaga ctgaacgaca agtcgaaca   29160
cttactaagt gttgaatttt aattttttag aaccatgaag atcctaggcc ttttaatttt   29220
ttctatcatt acctctgctc tatgcaattc tgacaatgag gacgttactg tcgttgtcgg   29280
atcaaattat acactgaaag gtccagcgaa gggtatgctt tcgtggtatt gctatttgg   29340
atctgacact acagaaactg aattatgcaa tcttaagaat ggcaaaattc aaaattctaa   29400
aattaacaat tatatatgca atggtactga tctgatactc ctcaatatca cgaaatcata   29460
tgctggcagt tacaccctgcc ctggagatga tgctgacagt atgattttttt acaaagtaac   29520
tgttgttgat cccactactc caacctccacc caccacaact actcacacca cacacacaga   29580
tcaaaccgca gcagaggagg cagcaaagtt agcctttgag gtccaagaca gttcatttgt   29640
tggcattacc cctacacctg atcagccggtg tccggggctg ctagtcagcg gcattgtcgg   29700
tgtgcttttcg ggattagcag tcataatcat ctgcatgttc attttttgctt gctgctatag   29760
aaggcttttac cgacaaaaat cagacccact gctgaacctc tatgtttaat tttttccaga   29820
gtcatgaagg cagttagcgc tctagttttt tgttctttga ttggcattgt tttttgcatt   29880
cctattccta aagttagctt tattaaagat gtgaatgtta ctgagggggg caatgtgaca   29940
ctggtaggta tagagggtgc tgaaaacacc acctggacaa aataccacct caatgggtgg   30000
aaagatattt gcaattggag tgtattagtt tatacatgtg agggagttaa tcttaccatt   30060
gtcaatgcca cctcagctca aaatggtaga attcaaggac aaagtgtcag tgtatctaat   30120
gggtatttta cccaacatac ttttatctat gacgttaaag tcataccact gcctacgcct   30180
agcccaccta gcactaccac acagacaacc cacactacag agacaaccac atacagtaca   30240
ttaaatcagc ctaccaccac tacagcagca gaggttgcca gctcgtctgg ggtccgagtg   30300
gcattttga tgtgggcccc atctagcagt ccactgcta gtaccaatga gcagactact   30360
gaattttgt ccactgtcga gagccacacc acagctacct ccagtgcctt ctctagcacc   30420
gccaatctct cctcgctttc ctctacacca atcagtcccg ctactactcc tagcccccgct   30480
cctcttccca ctccccctgaa gcaaacagac ggcggcatgc aatggcagat caccctgctc   30540
attgtgatcg ggttggtcat cctggccgtg ttgctctact acatcttctg ccgccgcatt   30600
cccaacgcgc accgcaagcc ggtctacaag cccatcattg tcgggcagcc ggagccgctt   30660
caggtggaag ggggtctaag gaatcttctc ttctcttta cagtatggtg attgaactat   30720
gattcctaga caattcttga tcactattct tatctgcctc ctccaagtct gtgccaccct   30780
cgctctggtg gccaacgcca gtccagactg tattgggccc ttcgcctcct acgtgctctt   30840
tgccttcacc acctgcatct gctgctgtag catagtctgc ctgcttatca ccttcttcca   30900
gttcattgac tggatctttg tgcgcatcgc ctacctgcgc caccaccccc agtaccgcga   30960
ccagcgagtg gcgcggctgc tcaggctcct ctgataagca tgcgggctct gctacttctc   31020
gcgcttctgc tgttagtgct cccccgtccc gtcgaccccc ggtccccac ccagtccccc   31080
gaggaggtcc gcaaatgcaa attccaagaa ccctggaaat tcctcaaatg ctaccgccaa   31140
aaatcagaca tgcatcccag ctggatcatg atcattggga tcgtgaacat tctggcctgc   31200
accctcatct ccctttgtgat ttaccccgtc tttgacttgg gttgaactc gccagaggcg   31260
ctctatctcc cgcctgaacc tgacacacca ccacagcaac ctcaggcaca cgcactacca   31320
ccactacagc ctaggccaca atacatgccc atattagact atgaggccga gccacagcga   31380
cccatgctcc ccgctattag ttacttcaat ctaaccggcg gagatgactg acccactggc   31440
caacaacaac gtcaacgacc ttctcctgga catggacggc cgcgcctcgg agcagcgact   31500
cgcccaactt cgcattcgcc agcagcagga gagagccgtc aaggagctgc aggatgcggt   31560
```

```
ggccatccac cagtgcaaga gaggcatctt ctgcctggtg aaacaggcca agatctccta    31620
cgaggtcact ccaaacgacc atcgcctctc ctacgagctc ctgcagcagc gccagaagtt    31680
cacctgcctg gtcggagtca accccatcgt catcacccag cagtctggcg ataccaaggg    31740
gtgcatccac tgctcctgcg actcccccga ctgcgtccac actctgatca agaccctctg    31800
cggcctccgc gacctcctcc ccatgaacta atcacccct tatccagtga aataaagatc    31860
atattgatga tgattttaca gaaataaaaa ataatcattt gatttgaaat aaagatacaa    31920
tcatattgat gatttgagtt taacaaaaaa ataagaatc acttacttga aatctgatac    31980
caggtctctg tccatgtttt ctgccaacac cacttcactc ccctcttccc agctctggta    32040
ctgcaggccc cggcgggctg caaacttcct ccacacgctg aaggggatgt caaattcctc    32100
ctgtccctca atcttcattt tatcttctat cagatgtcca aaaagcgcgt ccgggtggat    32160
gatgacttcg accccgtcta cccctacgat gcagacaacg caccgaccgt gcccttcatc    32220
aacccccct tcgtctcttc agatggattc aagagaagc cctgggggt gttgccctg       32280
cgactggccg accccgtcac caccaagaac ggggaaatca ccctcaagct gggagagggg    32340
gtggacctcg attcctcggg aaaactcatc tccaacacgg ccaccaaggc cgccgcccct    32400
ctcagttttt ccaacaacac catttccctt aacatggatc ccccttta cactaaagat    32460
ggaaaattat ccttacaagt ttctccacca ttaaatatac tgagaacaag cattctaaac    32520
acactagctt taggttttgg atcaggttta ggactccgtg gctctgcctt ggcagtacag    32580
ttagtctctc cacttacatt tgatactgat ggaaacataa agcttacctt agacagaggt    32640
ttgcatgtta caacaggaga tgcaattgaa agcaacataa gctgggctaa aggttttaaaa    32700
tttgaagatg gagccatagc aaccaacatt ggaaatgggt tagagtttgg aagcagtagt    32760
acagaaacag gtgttgatga tgcttaccca atccaagtta aacttggatc tggccttagc    32820
tttgacagta caggagccat aatggctggt aacaaaagag acgataaact cacttttgtgg   32880
acaacacctg atccatcacc aaactgtcaa atactcgcag aaaatgatgc aaaactaaca    32940
ctttgcttga ctaaatgtgg tagtcaaata ctggccactg tgtcagtctt agttgtagga    33000
agtggaaacc taaaccccat tactggcacc gtaagcagtg ctcaggtgtt tctacgtttt    33060
gatgcaaacg tgttcttttt aacagaacat tctacactaa aaaaatactg ggggtataagg    33120
cagggagata gcatagatgg cactccatat accaatgctg taggattcat gcccaattta    33180
aaaagcttatc caaagtcaca aagttctact actaaaaata atatagtagg caagtatac    33240
atgaatggag atgtttcaaa acctatgctt ctcactataa ccctcaatgg tactgatgac    33300
agcaacagta catattcaat gtcattttca tacacctgga ctaatggaag ctatgttgga    33360
gcaacatttg gggctaactc ttatacctc tcatacatcg cccaagaatg aacactgtat    33420
cccaccctgc atgccaaccc ttcccacccc actctgtgga acaaactctg aaacacaaaa    33480
taaaataaag ttcaagtgtt ttattgattc aacagtttta caggattcga gcagttattt    33540
ttcctccacc ctcccaggac atggaataca ccaccctcc ccccgcaca gccttgaaca    33600
tctgaatgcc attggtgatg gacatgcttt tggtctccac gttccacaca gtttcagagc    33660
gagccagtct cgggtcggtc agggagatga aaccctccgg gcactccgc atctgcacct    33720
cacagctcaa cagctgagga ttgtcctcgg tggtcgggat cacggttatc tggaagaagc    33780
agaagagcgg cggtgggaat catagtccgc gaacgggatc ggccggtggt gtcgcatcag    33840
gccccgcagc agtcgctgcc gccgccgctc cgtcaagctg ctgctcaggg ggtccggtc    33900
cagggactcc ctcagcatga tgcccacggc cctcagcatc agtcgtctgg tgcggcgggc    33960
gcagcagcgc atgcggatct cgctcaggtc gctgcagtac gtgcaacaca gaaccaccag    34020
gttgttcaac agtccatagt tcaacacgct ccagccgaaa ctcatcgcgg aaggatgct    34080
acccagtgg ccgtcgtacc agatcctcag gtaaatcagg tggtgccccc tccagaacac    34140
gctgccacg tacatgatct ccttgggcat gtggcggttc accacctccc ggtaccacat    34200
caccctctgg ttgaacatgc agccccggat gatcctgcgg aaccacaggg ccagcaccgc    34260
cccgcccgcc atgcagcgaa gagacccgg gtccggcaa tggcaatgga ggacccaccg    34320
tcgtacccg tggatcatct gggagctgaa caagtctatg ttggcacagc acaggcatat    34380
gctcatgcat ctcttcagca ctctcaactc ctcggggtc aaaaccatat cccagggcac    34440
ggggaactct tgcaggacag cgaacccgc agaacagggc aatcctgcca cagaacttac    34500
attgtgcatg gacagggtat cgcaatcagg cagcaccggg tgatcctcca ccagagaagc    34560
gcgggtctcg gtcctccac agcgtggtaa ggggccggc cgatacgggt gatgcgggga    34620
cgcggctgat cgtgttcgcg accgtgtcat gatgcagttg cttcggaca ttttcgtact    34680
tgctgtagca gaacctggtc cgggcgctgc acaccgatcg ccggcggcgg tctcggcgct    34740
tggaacgctc ggtgttgaaa ttgtaaaaca gccactctct cagaccgtgc agcagatcta    34800
gggcctcagg agtgatgaag atcccatcat gcctgatggc tctgatcaa tcgaccaccg    34860
tggaatgggc cagacccagc cagatgatgc aattttgttg ggtttcggtg acggcggggg    34920
agggaagaac aggaagaacc atgattaact tttaatccaa acggtctcgg agtacttcaa    34980
aatgaagatc gcggagatgg cacctctcgc ccccgctgtg ttggtggaaa ataacagcca    35040
ggtcaaaggt gatacggttc tcgagatgtt ccacgtggc ttccagcaaa gcctccacgc    35100
gcacatccag aaacaagaca atagcgaaag cgggagggtt ctctaattcc tcaatcatca    35160
tgttacactc ctgcaccatc cccagataat tttcattttt ccagccttga atgattcgaa    35220
ctagttcgtg aggtaaatcc aagccagcca tgataaagag ctcgcgcaga gcgccctcca    35280
ccggcattct taagcacacc ctcataattc caagatattc tgctcctggt tcacctgcag    35340
cagattgcaa agcggaatat caaaatctct gccgcgcatc ctgagctcct ccctcagcaa    35400
taactgtaag tactcttttca tatcctctcc gaaatttta gccataggac caccaggaat    35460
aagattaggg caagccacag tacagataaa ccgaagtcct ccccagtgag cattgccaaa    35520
tgcaagactc ctataagcat gctggctaga cccggtgata tcttccagat aactggacag    35580
aaaatcgccc aggcaatttt taagaaaatc aacaaaagaa aaatctcca ggtggacgtt    35640
tagagcctcg ggaacaacga tgaagtaaat gcaagcgggt cgttccagca tggttagtta    35700
gctgatctgt agaaaaaaca aaaatgaaca ttaaaccatg ctagcctggc gaacaggtgg    35760
gtaaatcgtt ctctccagca ccaggcaggc cacgggtct ccggcgcgac cctcgtaaaa    35820
attgtcgcta tgattgaaaa ccatcacaga gagacgttcc cggtgccgg cgtgaatgat    35880
tcgacaagat gaatacaccc ccggaacatt ggcgtccgc agtgaaaaaa agcgcccgag    35940
gaagcaataa ggcactacaa tgtctagtct caagtccaca aaagcgatgc catgcgatg    36000
aagcacaaaa ttctcaggtg cgtacaaaat gtaattactc ccctcctgca caggcagcaa    36060
agcccccgat ccctccaggt acacataaa agcctcagcg tccatagctt accgagcagc    36120
agcacacaac aggcgcaaga gtcagagaaa ggctgagctc taacctgtcc acccgctctc    36180
tgctcaatat atagcccaga tctacactga cgtaaaggcc aaagtctaaa aatacccgcc    36240
aaataatcac acacgcccag cacacgcccca gaaaccggtg acacactcaa aaaaatacgc    36300
```

```
gcacttcctc aaacgcccaa aactgccgtc atttccgggt tcccacgcta cgtcatcaaa    36360
acacgacttt caaattccgt cgaccgttaa aaacgtcacc cgccccgccc ctaacggtcg    36420
cccgtctctc agccaatcag cgccccgcat cccccaattc aaacacctca tttgcatatt    36480
aacgcgcaca aaaagtttga ggtatattat tgatgatgg                           36519
```

```
SEQ ID NO: 2              moltype = DNA  length = 2588
FEATURE                   Location/Qualifiers
source                    1..2588
                          mol_type = other DNA
                          organism = synthetic construct
misc_feature              1..2588
                          note = Chimpanzee adenovirus C68
SEQUENCE: 2
ttacaggatt cgagcagtta tttttcctcc accctcccag gacatggaat acaccaccct      60
ctcccccgc  acagccttga acatctgaat gccattggtg atggacatgc ttttggtctc     120
cacgttccac acagtttcag agcgagccag tctcgggtcg gtcagggaga tgaaaccctc     180
cgggcactcc cgcatctgca cctcacagct caacagctga ggattgtcct cggtggtcgg     240
gatcacggtt atctggaaga agcagaagag cggcggtggg aatcatagtc cgcgaacggg     300
atcggccggt ggtgtcgcat caggccccgc agcagtcgct gccgccgccg ctccgtcaag     360
ctgctgctca gggggtccgg gtccaggggac tccctcagca tgatgcccac ggccctcagc     420
atcagtcgtc tggtgcggcg ggcgcagcag cgcatgcgga tctcgctcag gtcgctgcag     480
tacgtgcaac acagaaccac caggttgttc aacagtccat agttcaacac gctccagccg     540
aaaactcatcg cgggaaggat gctacccacg tggccgtcgt accagatcct caggtaaatc     600
aagtggtgcc cctccagaa cacgctgccc acgtacatga tctccttggg catgtggcgg     660
ttcaccacct cccggtacca catcaccctc tggttgaaca tgcagcccg gatgatcctc      720
cggaaccaca gggccagcac cgccccgccc gccatgcagc gaaagaaccc cgggtcccgg     780
caatgcaat ggaggaccca ccgctcgtac ccgtggatca tctgggagct gaacaagtct      840
atgttggcac agcacaggca tatgctcatg catctcttca gcactctcaa ctcctcgggg     900
gtcaaaacca tatcccaggg cacggggaac tcttgcagga cagcgaaccc cgcagaacag     960
ggcaatcctc gcacagaact tacattgtgc atggacaggg tatcgcaatc aggcagcacc    1020
gggtgatcct ccaccagaga agcgcggtc tcggtctcct cacagcgtgg taaggggggcc    1080
ggccgatacg ggtgatggcg ggacgcggct gatcgtgttc gcgaccgtgt catgatgcag    1140
ttgctttcgg acatttttcgt acttgctgta gcagaacctg gtccgggcgc tgcacaccga    1200
tcgccggcg cggtctcggc gcttggaacg ctccggtgttg aaattgtaaa acagccactc    1260
tctcagaccg tgcagcagat ctagggcctc aggagtgatg aagatcccat catgcctgat    1320
ggctctgatc acatcgacca ccgtggaatg ggccagaccc agccagatga tgcaattttg    1380
ttgggttttcg gtgacggcgg gggagggaag aacaggaaga accatgatta actttttaatc   1440
caaacggtct cggagtactt caaaatgaag atcgcggaga tggcacctct cgccccgct     1500
gtgttggtgg aaaataacag ccaggtcaaa ggtgatacgg ttctcgagat gttccacggt    1560
ggcttccagc aaagcctcca cgcgcacatc cagaaacaag acaatagcga aagcggagg    1620
gttctctaat tcctcaatca tcatgttaca ctcctgcacc atcccagat aatttttcatt    1680
tttcagcct tgaatgattc gaactagttc gtgaggtaaa tccaagccag ccatgataaa    1740
gagctcgcgc aagcgccct ccaccggcat tcttaagcac acccctcataa ttccaagata    1800
ttctgctcct ggttcacctg cagcagattg acaagcggaa tatcaaaatc tctgccgcga   1860
tccctgagct cctcccctcag caataactgt aagtactctt tcatatcctc tccgaaatttt   1920
ttagccatag gaccaccagg aataagatta gggcaagcca cagtacagat aaaccgaagt    1980
cctcccccagt gagcattgcc aaatgcaaga ctgctataaa catgctggct agacccggtg   2040
atatcttcca gataactgga cagaaaatcg cccaggcaat tttttaagaaa atcaacaaaa    2100
gaaaaatcct ccaggtggac gttttagagcc tcgggaacaa cgatgaagta aatgcaagcg    2160
gtgcgttcca gcatggtttag ttagctgatc tgtagaaaaa acaaaaatga acattaaacc    2220
atgctagcct ggcgaacagg tgggtaaatc gttctctcca gcaccaggca ggccacgggg    2280
tctccggcgc gaccctcgta aaaattgtcg ctatgattga aaaccatcac agagagacgt    2340
tcccggtggc cggcgtgaat gattcgacaa gatgaataca cccccggaac attggcgtcc    2400
gcgagtgaaa aaaagcgccc gaggaagcaa taaggcacta caatgctcag tctcaagtcc    2460
agcaaaagcga tgccatgcgg atgaagcaca aaattctcag gtgcgtacaa aatgtaatta    2520
ctcccctcct gcacaggcag caaagccccc gatccctcca ggtacacata caaagcctca    2580
gcgtccat                                                             2588
```

```
SEQ ID NO: 3              moltype = AA  length = 124
FEATURE                   Location/Qualifiers
source                    1..124
                          mol_type = protein
                          organism = synthetic construct
REGION                    1..124
                          note = Chimpanzee adenovirus Y25
SEQUENCE: 3
MDAEALYVFL EGAGALLPVQ EGSNYIFYAP ANFVLHPHGV ALLELRLSIV VPRGFIGRFF     60
SLTDANVPGV YASSRIIHAG HREGLSVMLF NHGDSFYEGR AGDPVACLVL ERVIYPPVRQ   120
ASMV                                                                 124

SEQ ID NO: 4              moltype = AA  length = 129
FEATURE                   Location/Qualifiers
source                    1..129
                          mol_type = protein
                          organism = synthetic construct
REGION                    1..129
                          note = Chimpanzee adenovirus Y25
SEQUENCE: 4
MLERTPCTYS IVVPEALNLH LDDFSFVDFL KNCLPDFLSS YLEDITGSSQ HAYFNLTFGN     60
```

```
AHWGGLRFIC NVACPALIPG GPMAKNFGDD MKDYIQLLLR EELRDRGRDF DIPIVNLLQV  120
NQEQNLLEL                                                          129

SEQ ID NO: 5            moltype = AA  length = 117
FEATURE                 Location/Qualifiers
source                  1..117
                        mol_type = protein
                        organism = synthetic construct
REGION                  1..117
                        note = Chimpanzee adenovirus Y25
SEQUENCE: 5
MRVCLRMPVE GALRELFIMA GLDLPQELIR IIQGWKNENY LGMVQECNMM IEELENAPAF  60
AVLLFLDVRV EALLEATVEH LENRVTFDLA VIFHQHSGGE RCHLRDLHFE VLRDRLE     117

SEQ ID NO: 6            moltype = DNA  length = 36711
FEATURE                 Location/Qualifiers
source                  1..36711
                        mol_type = other DNA
                        organism = synthetic construct
misc_feature            1..36711
                        note = Chimpanzee adenovirus AdY25
SEQUENCE: 6
ccatcatcaa taatatacct caaactttt gtgcgcgtta atatgcaaat gaggcgtttg  60
aatttgggaa gggaggaagg tgattggccg agagaagggc gaccgttagg ggcggggcga  120
gtgacgtttt gatgacgtga ccgcgaggag gagccagttt gcaagttctc gtgggaaaag  180
tgacgtcaaa cgaggtgtgg tttgaacacg gaaatactca attttcccgc gctctctgac  240
aggaaatgag gtgtttctag gcggatgcaa gtgaaaacgg gccattttcg cgcgaaaact  300
gaatgaggaa gtgaaaatct gagtaattc gcgtttatga cagggaggag tatttgccga  360
gggccgagta gactttgacc gattacgtgg gggtttcgat taccgtgttt ttcacctaaa  420
tttccgcgta cggtgtcaaa gtccggtgtt tttacgtagg tgtcagctga tcgccagggt  480
atttaaacct gcgctctcca gtcaagaggc cactcttgag tgccagcgag aagagttttc  540
tcctccgcgc cgcgagtcag atctacactt gaaagatga ggcacctgag agacctgccc  600
gatgagaaaa tcatcatcgc ttccgggaac gagattctgg aactggtggt aaatgccatg  660
atgggcgacg accctccgga gccccccacc ccatttgagg caccttcgct cacgatttg  720
tatgatctgg aggtggatgt gcccgaggac gaccccaacg aggaggcggt aaatgattta  780
tttagcgatg ccgcgctgct agctgccgag gaggcttcga gccctagctc agacagcgac  840
tcttcactgc ataccctag accggacaga ggtgagaaaa agatcccga gcttaaaggg  900
gaagagatgg acttgcgctg ctatgaggaa tgcttgcccc cgagcgatga tgaggacgag  960
caggcgatcc agaacgcagc gagccaggga atgcaagccg ccagcgagag ttttgcgctg  1020
gactgcccgc ctctgcccgg acacggctgt aagtcttgtg aatttcatcg cttgaatact  1080
ggagataaag ctgtgttatg tgcactttgc tatatgagag cttacaacca ttgtgtttac  1140
agtaagtgtg attaagttga actttagagg gaggcagaga gcagggtgac tgggcgatga  1200
ctggtttatt tatgtatata tgttctttat ataggtccgg tctctgacgc agatgatgag  1260
acccccacta cagagtccac ttcgtcaccc ccagaaattg gcacatctcc acctgagaat  1320
attgttagac cagttcctgt tagagccact gggaggagag cagctgtgga atgtttggat  1380
gacttgctac aggctgggga tgaacctttg gacttgtgta cccggaaacg ccccaggcac  1440
taagtgccac acatgtgtgt ttacttgagg tgatgtcagt atttataggg tgtggagtgc  1500
aataaaaaat gtgttgactt taagtgcgtg gtttatgact caggggtggg gactgtgggt  1560
atataagcag gtgcagacct gtgtggttag ctcagagcgg catggagatt tggacgatct  1620
tggaagatct tcacaagact agacagctgc tagagaacgc ctcgaacgga gtctctcacc  1680
tgtggagatt ctgcttcggt ggcgacctag ctaagctagt ctataggcc aaacaggatt  1740
atagcgaaca atttgaggtt attttgagag agtgtccggg tcttttgac gctcttaatt  1800
tgggtcatca gactcacttt aaccagagga ttgtaagagc ccttgatttt actactcccg  1860
gcagatccac tgcggcagta gccttttttg ctttcttct tgacaaatgg agtcaagaaa  1920
cccatttcag cagggattac cagctggatt tcttagcagt agctttgtgg agaacatgga  1980
aatcccagcg cctgaatgca atctcaggct acttgccggt acagccacta gacactctga  2040
agatcctgaa tctccaggag agtcccaggg cacgccaacg tcgccggcag cagcagcggc  2100
agcaggagga ggatcaagaa gagaacccga gagccggcct ggaccctccg gcggaggagg  2160
agtagctgac ctgttttcctg aactgcgccg ggtgctgact aggtcttcga gtggtcggga  2220
gaggggagtt aagcgggaga ggcatgatga gactaatgaa gaaactgaac tgactgtggga  2280
tctgatgagc cgcaagcgtc cagaaacagt gtggtggcat gaggtgcagt cgactggcac  2340
agatgaggtg tcagtgatgc atgagaggtt tccctagaa caagtcaaga cttgttggtt  2400
agagcctgag gatgattggg aggtagccat caggaattat gccaagctgg ctctgaggcc  2460
agacaagaag tacaagatta ctaagctgat aaatatcagg aatgcctgct acatctcagg  2520
gaatggggct gaagtggaga tctgtcttca ggaaagggtg gctttcagat gctgcatgat  2580
gaatatgtac ccgggagtgg tgggcatgga tggggtcacc tttatgaaca tgaggttcag  2640
gggagatggg tataatggca cggtctttat ggccaatacc aagctgacag ttcatggctg  2700
ctccttcttt gggtttaata acacctgcat tgaggcctgg gtcaggttg tgtgaggg  2760
ctgtagtttt tcagccaact ggatggggt cgtgggcagg accaaggta tgctgtccgt  2820
gaagaaatgc ttgttcgaga ggtgccacct gggggtgatg agcgaggggcg aagccagaat  2880
ccgccactgc gcctctaccg agacgggctg tttttgtgctg tgcaagggca atgctaagat  2940
caagcataat atgatctgtg agcctcgga cgagcgcggc taccagatgc tgacctgcgc  3000
cggtgggaac agccatatgc tggccaccgt gcatgtggcc tccatgccc gcaagccctg  3060
gcccgagttc gagcaataatg tcatgaccag catcatcggg ccgccaacgg  3120
catgttcatg cccctatcagt gcaacctgaa ttatgtgaag gtgctgctgg agcccgatgc  3180
catgtccaga gtgagcctga cggggtgttt tgacatgaat gtggaggtgt ggaagattct  3240
gagatatgat gaatccaaga ccaggtgccg agcctgcgag tgcgggggga agcatgccag  3300
gttccagccc gtgtgtgtgg aggtgacgga ggacctgcga cccgatcatt tggtgttgtc  3360
ctgcaccggg acggagttcg gttccagcgg ggaagaatct gactagagtg agtagtgttc  3420
```

-continued

```
tggggcgggg gaggacctgc atgagggcca gaatgactga aatctgtgct tttctgtgtg    3480
ttgcagcatc atgagcggaa gcggctcctt tgagggaggg gtattcagcc cttatctgac    3540
ggggcgtctc ccctcctggg cgggagtgcg tcagaatgtg atgggatcca cggtggacgg    3600
ccggcccgtg cagcccgcga actcttcaac cctgacctat gcaaccctga gctcttcgtc    3660
ggtggacgca gctgccgccg cagctgctgc atccgcgcc agcgccgtgc gcggaatggc    3720
catgggcgcc ggctactacg gcactctggt ggccaactcg agttccacca ataatcccgc    3780
cagcctgaac gaggagaagc tgctgctgct gatgggccag cttgaggcct tgacccagcg    3840
cctgggcgag ctgacccagc aggtggctca gctgcaggag cagacgcggg ccgcggttgc    3900
cacggtgaaa tccaaataaa aaatgaatca ataaataaac ggagacggtt gttgatttta    3960
acacagagtc tgaatcttta tttgattttt cgcgcgcggt aggccctgga ccaccggtct    4020
cgatcattga gcaccggtg gatcttttcc aggaccggt agaggtgggc ttggatgttg    4080
aggtacatgg gcatgagccc gtcccggggg tggaggtagc tccattgcag ggcctcgtgc    4140
tcgggggtgg tgttgtaaat cacccagtca tagcagggg gcagggcgtg gtgttgcaca    4200
atatctttga ggaggagact gatggccacg ggcagcctct tggtgtaggt gtttacaaat    4260
ctgttgagct gggagggatg catgcggggg gagatgaggt gcatcttggc ctggatcttg    4320
agattggcga tgttaccgcc cagatcccgc ctggggttca tgttgtgcag gaccaccagc    4380
acggtgtatc cggtgcactt ggggaattta tcatgcaact tggaagggaa ggcgtgaaag    4440
aatttggcga cgcccttgtg tccgcccagg ttttccatgc actcatccat gatgatggca    4500
atgggcccgt gggcggcggc ctgggcaaag acgtttcggg ggtcggacac atcatagttg    4560
tggtcctggg tgaggtcatc ataggccatt ttaatgaatt tggggcggag ggtgccggac    4620
tggggggacaa aggtaccctc gatcccgggg gcgtagttcc cctcacagat ctgcatctcc    4680
caggctttga gctcagaggg ggggatcatg tccacctgcg gtgcgataaa gaacacggtt    4740
tccggggcg gggagatgag ctgggccgaa agcaagttcc ggagcagctg ggacttgcca    4800
cagccggtgg ggccgtaaat gaccccgatg accggctgca ggtggtagtt gagggagaga    4860
cagctgccgt cctcccggag gaggggggcc acctcgttca tcatctcgcg cacgtgcatg    4920
ttctcgcgca ccagttccgc caggaggcgc tctccccca agataggag ctcctggagc    4980
gaggcgaagt ttttcagcgg cttgagtccg tcggccatgg gcattttgga gagggtctgt    5040
tgcaagagtt ccaagcggtc ccagagctcg gtgatgtgct ctacggcatc tcgatccagc    5100
agacctcctc gtttcgcggg ttgggacgac tgcgggagta gggcaccaga cgatgggcgt    5160
ccagcgcagc caggtccgg tccttccagg gccgcagcgt ccgcgctcagg gtggtctccg    5220
tcacggtgaa ggggtgcgcg ccgggctggg cgcttgcgag ggtgcgcttc aggctcatcc    5280
ggctggtcga aaaccgctcc cgatcggcgc cctgcgcgtc ggccaggtag caattgacca    5340
tgagttcgta gttgagcgcc tcggccgcgt ggcctttggc gcggagctta cctttggaag    5400
tctcccgca ggcgggacag aggagggact tgagggcgta gagctggggg gcgaggaaga    5460
cggaatcggg ggcgtaggcg tccgcgccgc agtcggcgca gacggtctcg cactccacga    5520
gccaggtgag gtcgggctgg tcggggtcaa aaaccagttt cccgccgttc ttttttgatgc    5580
gtttcttacc tttggtctcc atgagctcgt gtccccgctg ggtgacaaag aggctgtccg    5640
tgtccccgta gaccgacttt atgggccggt cctcgagcgg tgtgccgcgg tcctcctcgt    5700
agaggaaccc cgcccactcc gagacgaaag cccgggtccg ggccagcacg aaggaggcca    5760
cgtgggacgg gtagcggtcg ttgtccacca gcgggtccac ttttttccagg gtatgcaaac    5820
acatgtcccc ctcgtccaca tccaggaagg tgattggctt gtaagtgtag gccacgtgac    5880
cggggtcccc ggccgggggg gtataaaagg gggcgggccc ctgctcgtcc tcactgtctt    5940
ccggatcgct gtccaggagc gccagctgtt gggtaggta ttccctctcg aaggcgggca    6000
tgacctcggc actcaggttg tcagtttcta gaaacgagga ggatttgata ttgacggtgc    6060
cagcggagat gcctttcaag agcccctcgt ccatctggtc agaaaagacg atttttttgt    6120
tgtcgagctt ggtggcgaag gagccgtaga gggcgttgga aaggagcttg gcgatggagc    6180
gcatgtctg gttttttttcc ttgtcggcgc gctccttggc cgcgatgttg agctgcacgt    6240
actcgcgcgc cacgcacttc cattcgggga agacggtggt catctcgtcg ggcacgattc    6300
tgacctgcca acctcgatta tgcagggtga tgaggtccac actggtgcc acctcgccgc    6360
gcaggggctc gttggtccag cagaggcggc cgcccttgcg cgagcagaag gggggcagag    6420
ggtccagcat gacctcgtcg gggggtcgg catcgatggt gagcaggagt cgcaggagat    6480
cggggtcgaa gtagctgatg gaagtggcca gatcgtccag ggaagcttgc cattcgcgca    6540
cggccagcgc gcgctcgtag ggactgaggg gcgtgcccca gggcatgggg tgggtgagcg    6600
cggaggcgta catgccgcag atgtcgtaga cgtagagggg ctcctcgagg atgccgatgt    6660
aggtgggta gcagcgcccc ccgcggatgc tggcgcgcac gtagtcatac agctcgtcgg    6720
agggcgcgag gagccccggg cccaggttgg tgcgactggg cttttcggcg cggtagacga    6780
tctggcgaaa gatggcatgc gagttggagg agatggtggg cctttggaag atgttgaagt    6840
gggcgtgggg gaggccgacc gagtcgcgga tgaagtgggc gtaggagtct tgcagtttgg    6900
cgacgagctc ggccggtgacg aggacgtcca gagcgaggtc tcctggatga    6960
tgtcatactt gagctggccc ttttgttttcc acagctgcg gttgaagg aactcttcgc    7020
ggtccttcca gtactcttcg agggggaacc cgtcctgatc tgcacggtaa gagcctagca    7080
tgtagaactg gttgacggcc ttgtaggcgc agcagccctt ctccacgggg agggcgtagg    7140
cctgggcggc cttgcgcagg gaggtgtgcg tgagggcgaa ggtgtccctg accatgacct    7200
tgaggaactg gtgcttgaaa tcgatatcgt cgcagccccc ctgctcccag agctggaagt    7260
ccgtgcgctt cttgtaggcg gggttggca aagcgaaagt aacatcgttg aaaaggatct    7320
tgcccgcgcg gggcataaag ttgcgagtga tgcggaaagt ctgggcacc tcggcccggt    7380
tgttgatgac ctgggcggcg agcacgatct cgtcgaaacc gttgatgttg tggcccacga    7440
tgtagagttc cacgaatcgc gggcggccct tgacgtgggg cagcttcttg agctcctcgt    7500
aggtgagctc gtcgggtcg ctgagaccgt gctgctccga cgccagtcg gcgagatggg    7560
ggttggcgcg gaggaaggaa gtccagagat ccacgccag gcggttttgc agacggtccc    7620
ggtactgacg gaactgctgc ccgacggcca tttttttcggg ggtgacgcag tagaaggtgc    7680
gggggtcccc gtgccagcgg tcccatttga gctggagggc gagatcgagg gcgagctcga    7740
cgaggcggtc gtccctgag agtttcatga ccagcatgaa ggggacgagc tgcttgccga    7800
aggacccat ccaggtgtag gttttccacat cgtaggtgag gaagagcctt ccggtgcgag    7860
gatgcgagcc gatggggaag aactggatct cctgccacca attggaggaa tggctgttga    7920
tgtgatggaa gtagaaatgc cgacggcgcg ccgaacactc gtgcttgtgt ttatacaagc    7980
ggccacagtg ctcgcaacgc tgcacggat gcacgtgctg cacgagcgt acctgagttc    8040
cttttgacgag gaatttcagt gggaagtgga gtcgtgcgc ctgcatctcg tgctgtacta    8100
cgtcgtggtg gtcggcctgg ccctcttctg cctcgatggt ggtcatgctg acgagcccgc    8160
```

```
gcgggaggca ggtccagacc tcggcgcgag cgggtcggag agcgaggacg agggcgcgca  8220
ggccggagct gtccagggtc ctgagacgct gcggagtcag gtcagtgggc agcggcggcg  8280
cgcggttgac ttgcaggagt ttttccaggg cgcgcgggag gtccagatgg tacttgatct  8340
ccaccgcgcc gttggtggcg acgtcgatgg cttgcagggt cccgtgcccc tggggtgtga  8400
ccaccgtccc ccgtttcttc ttgggcgcag ggggcggtgc gggcggtgcc tcttccatgg  8460
ttagaagcgg cggcgaggac gcgcgccggg cggcagaggc ggctcggggc ccggaggcag  8520
gggcggcagg ggcacgtcgg cgccgcgcgc gggtaggttc tggtactgcg cccggagaag  8580
actggcgtga gcgacgacgc gacggttgac gtcctggatc tgacgcctct gggtgaaggc  8640
cacgggaccc gtgagtttga acctgaaaga gagttcgaca gaatcaatct cggtatcgtt  8700
gacggcggcc tgccgcagga tctccttgcac gtcgcccgag ttgtcctggt aggcgatctc  8760
ggtcatgaac tgctcgatct cctcctcctg aaggtctccg cgaccggcgc gctccacggt  8820
ggccgcgagg tcgttggaga tgcggcccat gagctgcgag aaggcgttca tgcccgcctc  8880
gttccagacg cggctgtaga ccacgacgcc ctcgggatcg cgggcgcgca tgaccacctg  8940
ggcgaggttg agctccacgt ggcgcgtgaa gaccgcgtag ttgcagaggc gctggtagag  9000
gtagttgagc gtggtggcga tgtgctcggt gacgaagaaa tacatgatcc agcggcggag  9060
cggcatctcg ctgacgtcgc ccagcgcctc aagcgttcc atggcctcgt aaaagtccac   9120
ggcgaagttg aaaaactggg agttgcgcgc cgagacggtc aactcctcct ccagaagacg  9180
gatgagctcg gcgatggtgg cgcgcacctc gcgctcgaag gccccggga gttcctccac   9240
ttcctcctct tcttcctcct ccactaacat ctcttctact tcctcctcag gcggtggtgg  9300
tggcggggga gggggcctgc gtcgcggcgc gcgcacgggc agacggtcga tgaagcgctc  9360
gatggtctcg ccgcgccggc gtcgcatggt ctcggtgacg gcgcgccgt cctcgcgggg   9420
ccgcggcgtg aagacgccgc cgcgcatctc caggtgcgca gggggtccc cgttgggcag  9480
ggagagggcg ctgacgatgc atcttatcaa ttgccccgta gggactccgc gcaaggacct  9540
gagcgtctcg agatccacgg gatctgaaaa ccgttgaacg aagcttcga gccagtcgca   9600
gtcgcaaggt aggctgagca cggtttcttc tgccgggtca tgttggggag cggggcgggc  9660
gatgctgctg gtgatgaagt tgaaataggc ggttctgaga cggcggatgg tggcgaggag  9720
caccaggtct ttgggcccgg cttgctggat gcgcagacgg tcggccatgc cccaggcgtg  9780
gtcctgacac ctgccaggt ccttgtagta gtcctgcatg agccgctcca cgggcacctc   9840
ctcctcgccc gcgcggccgt gcatgcgcgt gagcccgaag ccgcgctggg gctggacgag  9900
cgccaggtcg gcgacgacgc gctcggccag gatggcctgc tggatctgag tgagggtggc  9960
ctggaagtcg tcaaagtcga cgaagcggtg gtaggctccg gtgttgatgg tgtaggagca  10020
gttggccatg acgaccagt tgacggtctg gtggcccgga cgcacgagct cgtggtactt   10080
gaggcgcgag taggcgcgcg tgtcgaagat gtagtcgttg caggtgcgca ccaggtactg  10140
gtagccgatg aggaagtgcg gcggcggctg gcggtagagc ggccatcgct cggtggcggg  10200
ggcgccgggc gcgaggtcct cgagcatggt gcggtggtag ccgtagatgt acctggacat  10260
ccaggtgatg ccggcggcgg tggtggaggc gcgcgggaac tcgcggacgc ggttccagat  10320
gttgcgcagc ggcaggaagt agttcatggt gggcacggtc tggcccgtga ggcgcgcgca  10380
gtcgtggatg ctctatacgg gcaaaaacga aagcggtcag cggctcgact ccgtggcctg  10440
gaggctaagc gaacgggttg ggctgcgcgt gtaccccggt tcgaatctcg aatcaggctg  10500
gagccgcagc taacgtggta ctggcactcc cgtctcgacc caagcctgca ccaaccctcc  10560
aggatacgga ggcgggtcgt tttgcaactt tttttggagg ccggaaatga aactagtaag  10620
cgcggaaagc ggccgaccgc gatggctcgc tgccgtagtc tggagaagaa tcgccagggt  10680
tgcgttgcgg tgtgccccgg ttcgaggccg gccggattcc gcggctaacg agggcgtggc  10740
tgccccgtcg tttccaagac cccatagcca gccgacttct ccagttacgg agcgagcccc  10800
tcttttgttt tgtttgtttt tgccagatgc atcccgtact gcggcagatg cgcccccacc  10860
accctccacc gcaacaacag cccccctcctc cacagccggc gcttctgccc ccgccccagc  10920
agcagcagca acttccagcc acgaccgccg cggccgccgc gagcggggct ggacagactt  10980
ctcagtatga tcacctggcc ttggaagagg gcgaggggct ggcgcgcctg ggggcgtcgt  11040
cgccggagcg gcacccgcgc gtgcagatga aaagggacgc tcgcgaggcc tacgtgccca  11100
agcagaacct gttcagagac aggagcggcg aggagcccga ggagatgcgc gcggcccggt  11160
tccacgcggg gcgggagctg cggcgggcc tggaccgaaa gagggtgctg agggacgagg  11220
atttcgaggc ggacgagctg acggggatca gccccgcgcg cgcgcacgtg gccgcggcca  11280
acctggtcac ggcgtacgag cagaccgtga aggaggagag caacttccaa aaatccttca  11340
acaaccacgt gcgcacccctg atcgcgcgcg aggaggtgac cctgggcctg atgcacctgt  11400
gggacctgct ggaggccatc gtgcagaacc ccaccagcaa gccgctgacg gcgcagctgt  11460
tcctggtggt gcagcatagt cgggacaacg aggcgttcag ggaggcgctg ctgaatatca  11520
ccgagcccga gggccgctgg ctcctggacc tggtgaacat tctgcagagc atcgtggtgc  11580
aggagcgcgg gctgccgctg tccgagaagc tggcggccat caacttctcg gtgctgagtc  11640
tgggcaagta ctacgctagg aagatctaca agaccccgta cgtgcccata gacaaggagg  11700
tgaagatcga cgggttttac atgcgcatga ccctgaaagt gctgacccgtg agcgacgatc  11760
tggggggtgta ccgcaacgac aggatgcacc gcgcggtgag cgccagcagg cggcgcgagc  11820
tgagcgacca ggagctgatg cacagcctgc agcgggccct gaccgggggcc gggaccgagg  11880
gggagagcta ctttgacatg ggcgcggacc tgcactggca gcccagccgc cgggccttgg  11940
aggcggcagg cggtccccccc tacatagaag aggtggacga tgaggtggca gaggagggaa  12000
agtacctgga agactgatgg cgcgaccgta tttttgctag atgcaacaac agccaccctcc  12060
tgatcccgcg atgcgggcgg cgctgcagag ccagccgtcc ggcattaact cctcggacga  12120
ttggacccag gccatgcaac gcatcatggc gctgacgacc cgcaacccg aagctttag    12180
acagcagccc caggccaacc ggctctcggc catcctggag gccggtggtgc cctcgcgctc  12240
caaccccacg cacgagaagg tcctggccat cgtggtggaga ctggtggaga acaaggccat  12300
ccgcggcgac gaggccggcc tggtgtacaa cgcgctgctg gagcgcgtgg cccgctacaa  12360
cagcaccaac gtgcagacca acctggaccg catggtgacc gacgtgcgcg aggccgtggc  12420
ccagcgcgag cggttccacc gcgagtccaa cctgggatcc atggtggcgc tgaacgcctt  12480
cctcagcacc cagcccgcca acgtgccccg gggccaggag gactacacca acttcatcag  12540
cgccctgcgg ctgatggtga cgcgagtgcc ccagagcgag gtgtaccagt ccgggccgga  12600
ctacttcttc cagaccagtc gccagggctt cgcagaccgtg aacctgagcc aggcgttcaa  12660
gaacttgcag ggcctgtggg gcgtgcaggc cccggtcggg gaccgcgcga cggtgtcgag  12720
cctgctgacg ccgaactcgc gcctgctgct gctgctggtg gccccccttca cggacagcgg  12780
cagcatcaac cgcaactcgt acctgggcta cctgattaac ctgtaccgcg aggccatcgg  12840
ccaggcgcac gtggacgagc agacctacca ggagatcacc cacgtgagcc gcgccctggg  12900
```

```
ccaggacgac ccgggcaatc tggaagccac cctgaacttt ttgctgacca accggtcgca  12960
gaagatcccg ccccagtaca cgctcagcgc cgaggaggag cgcatcctgc gatacgtgca  13020
gcagagcgtg ggcctgttcc tgatgcagga gggggccacc cccagcgccg cgctcgacat  13080
gaccgcgcgc aacatggagc ccagcatgta cgccagcaac cgcccgttca tcaataaact  13140
gatggactac ttgcatcggg cggccgccat gaactctgac tatttcacca acgccatcct  13200
gaatccccac tggctcccgc cgccgggggtt ctacacgggc gagtacgaca tgcccgaccc  13260
caatgacggg ttcctgtggg acgatgtgga cagcagcgtg ttctcccccc gaccgggtgc  13320
taacgagcgc cccttgtgga agaaggaagg cagcgaccga cgcccgtcct cggcgctgtc  13380
cggccgcgag ggtgctgccg cggcggtgcc cgaggccgcc agtcctttcc cgagcttgcc  13440
cttctcgctg aacagtattc gcagcagcga gctgggcagg atcacgcgcc cgcgcttgct  13500
gggcgaggag gagtacttga atgactcgct gttgagaccc gagcgggaga agaacttccc  13560
caataacggg atagagagcc tggtggacaa gatgagccgc tggaagacgt atgcgcagga  13620
gcacagggac gatccgtcgc aggggccac gagccggggc agcgccgccc gtaaacgccg  13680
gtggcacgac aggcagcggg gactgatgtg ggacgatgag gattccgccg acgacagcag  13740
cgtgttggac ttgggtggga gtggtaaccc gttcgctcac ctgcgccccc gcatcgggcg  13800
catgatgtaa gagaaaccga aaataaatga tactccaccaa ggccatggcg accagcgtgc  13860
gttcgttct tctctgttgt tgtatctagt atgatgaggc gtgcgtaccc ggagggtcct  13920
cctccctcgt acgagagcgt gatgcagcag gcgatgcggc cggcggcggc gatgcagccc  13980
ccgctggagg ctccttacgt gccccccgcg tacctggcgc ctacgggagg cggaacagc  14040
attcgttact cggagctggc acccttgtac gataccacc ggttgtacct ggtgacaac  14100
aagtcggcgg acatcgcctc gctgaactac cagaacgacc acagcaactt cctgaccacc  14160
gtggtgcaga acaatgactt caccccccacg gaggccagcc cccagaccat caactttgac  14220
gagcgctcgc ggtggggcgg tcagctgaaa accatcatgc acaccaacat gcccaacgtg  14280
aacgagttca tgtacagcaa caagttcaag gcgcgggtga tggtctcccg caagacccc  14340
aacgggtgta cagtgacaga tggtagtcag gatatcttgg agtatgaatg ggtggagttt  14400
gagctgcccg aaggcaactt ctcggtgacc atgaccatcg acctgatgaa caacgccatc  14460
atcgacaatt acttggcggt ggggcggcag aacgggtcc tggagagcga tatcggcgtg  14520
aagttcgaca ctaggaactt caggctgggc tgggaccccg tgaccgagct ggtcatgccc  14580
ggggtgtaca ccaacgaggc cttccacccc gatattgtct tgctgcccgg ctgcggggtg  14640
gacttcaccg agagccgcct cagcaacctg ctgggcattc gcaagaggca gcccttccag  14700
gagggcttcc agatcatgta cgaggatctg gagggggca acatcccgc gctcctggat  14760
gtcgacgcct atgagaaaag caaggaggag agccgccgcg cggcgactgc agctgtagcc  14820
accgcctcta ccgaggtcag gggcgataat tttgccagcc ctgcagcagt ggcagcggcc  14880
gaggcggctg aaaccgaaag taagatagtc attcagccgg tggagaagga tagcaaggac  14940
aggagctaca acgtgctgcc ggacaagata aacaccgcct accgcagctg gtacctgccc  15000
tacaactatg gcgaccccga gaagggcgtg cgctcctgga cgctgctcac cacctcggac  15060
gtcacctgcg gcgtggagca agtctactgg tcgctgcccg acatgatgca agacccggtc  15120
accttccgct ccacgcgtca agttagcaac taccggtgtg tgggcgccga gctcctgccc  15180
gtctactcca agagcttctt caacgagcag gccgtctact ccagcagct gcggccttc  15240
acctcgctca cgcacgtctt caaccgcttc cccgagaacc agatcctcgt ccgcccgccc  15300
gcgcccacca ttaccaccgt cagtgaaaac gttcctgctc tcacagatca cgggaccctg  15360
ccgctgcgca gcagtatccg gggagtccag cgcgtgaccg ttactgacgc cagacgccgc  15420
acctgcccct acgtctacaa ggccctgggc atagtcgcgc cgcgtcct ctcgagccgc  15480
accttctaaa aaatgtccat tctcatctcg cccagtaata acaccggttg ggcctgcgc  15540
gcgcccagca agatgtacgg aggcgctcgc aacgctcca cgcaacaccc cgtgcgcgtg  15600
cgcgggcact tccgcgctcc ctggggcgcc ctcaaggggc gcgtgcggtc gcgcaccacc  15660
gtcgacgacg tgatcgacca ggtggtggcc gacgcgcgca actacacccc cgccgccgcc  15720
cccgtctcca ccgtgacgc cgtcatcgac agcgtggtgg ccgacgcgcg ccggtacgcc  15780
cgcgccaaga gccggcggcg gcgcatcgcc cggcggcacc ggagcacccc cgccatgcgc  15840
gcggcgcgag ccttgctgcg cagggccagg cgcacgggac gcagggccat gctcagggcg  15900
gccagacgcg cggcttcagg cgccagcgcc ggcaggaccc ggagacgcgc ggccacggcg  15960
gcggcagcgg ccatcgccag catgtcccgc ccgcggcgag ggaacgtgta ctgggtgcgc  16020
gacgccgcca ccggtgtgcg cgtgcccgtg cgcacccgcc cccctcgcac ttgaagatgt  16080
tcacttcgcg atgttgatgt gtcccagcgg cgaggaggat gtccaagcgc aaattcaagg  16140
aagagatgct ccaggtcatc gcgcctgaga tctacggccc cgcggtggtg aaggaggaaa  16200
gaaagcccg caaaatcaag cgggtcaaaa aggacaaaaa ggaagaagat gacgatctgg  16260
tggagtttgt gcgcgagttc gcccccccggc ggcgcgtgca gtggcgcggg cggaaagtgc  16320
acccggtgct gagacccggc accaccgtgg tcttcacgcc cggcgagcgc tccggcagcg  16380
cttccaagcg ctcctacgac gaggtgtacg gggacgagga catcctcgag caggcggccg  16440
agcgcctggg cgagtttgct tacggcaagc gcaccgcc cgccctgaag gaagaggcgg  16500
tgtccatccc gctggaccac ggcaacccca cgccgagcct caagcccgtg acctgcagc  16560
aggtgctgcc gagcgcagcg ccgcgccggg ggttcaagcg cgagggcgag gatctgtacc  16620
ccaccatgca gctgatggtg cccaagcgcc agaagctgga agacgtgctg gagaccatga  16680
aggtggaccc ggacgtgcag cccgaggtca aggtgcgcc catcaagcag gtggcccggg  16740
gcctgggcgt gcagaccgtg gacatcaaga tccccacgcg gcccatggaa acgcagaccg  16800
agcccatgat caagcccagc accagcacca tggaggtgca gacggatccc tggatgccat  16860
cggctcctag ccgaagaccc cggcgcaagt acggcgcggc cagcctgctg atgcccaact  16920
acgcgctgca tccttccatc atcccacgc gggctaccg cggcacgcgc ttctaccgcg  16980
gtcatacaac cagccgccgc cgcaagacca ccaccccgc cccgcgtcgc cgcacagccg  17040
ctgcatctac ccctgccgcc ctggtgcgga gagtgtaccc ccggccgc gcgcctctga  17100
ccctaccgcg cgcgcgctac caccccgagca tcgccattta aactttcgcc tgctttgcag  17160
atggccctca catgccgcct ccgcgttccc attacgggct accgaggaag aaaccgcgc  17220
cgtagaaggc tggcggggaa cgggatgcgt cgccaccacc atcggcggcg gcgcgccatc  17280
agcaaggt tgggggagg cttcctgccc gcgctgatcc ccatcatgc ggcggcgatc  17340
ggggcgatcc ccggcattgc ttccgtggcg gtgcaggcct ctcagcgcca ctgagacact  17400
tggaaaacat cttgtaataa accaatggac tctgacgctc ctggtcctgt gatgtgtttt  17460
cgtagacaga tggaagacat caattttcg tccctggctc cgcgacacgg cacgcggccg  17520
ttcatgggca cctggagcga catcggcacc agccaactga acggggcgc cttcaattgg  17580
agcagtctct ggagcgggct taagaatttc gggtccacgc ttaaaaccta tggcagcaag  17640
```

```
gcgtggaaca gcaccacagg gcaggcgctg agggataagc tgaaagagca gaacttccag   17700
cagaaggtgg tcgatgggct cgcctcgggc atcaacgggg tggtggacct ggccaaccag   17760
gccgtgcagc ggcagatcaa cagccgcctg gacccgtgc cgcccgcgg ctccgtggag     17820
atgccgcagg tggaggagga gctgcctccc ctggacaagc ggggcgagaa gcgacccgc    17880
cccgacgcgg aggagacgct gctgacgcac acggacgagc cgcccccgta cgaggaggcg   17940
gtgaaactgg gtctgcccac cacgcggccc atcgcgcccc tggccaccgg ggtgctgaaa   18000
cccgaaagta ataagcccgc gaccctggac ttgcctcctc ccgcttcccg cccctctaca   18060
gtggctaagc cctgccgcc ggtggccgtg gcccgcgcgc gacccggggg ctccgcccgc    18120
cctcatgcga actggcagag cactctgaac agcatcgtgg gtctgggagt gcagagtgtg   18180
aagcgccgcc gctgctatta aacctaccgt agcgcttaac ttgcttgtct gtgtgtgtat   18240
gtattatgtc gccgctgtcc gccagaagga ggagtgaaga ggcgcgtcgc cgagttgcaa   18300
gatgccacc ccatcgatgc tgccccagtg ggcgtacatg cacatcgccg acaggacgc     18360
ttcggagtac ctgagtccgg gtctggtgca gttcgcccgc gccacagaca cctacttcag   18420
tctggggaac aagtttagga acccacggt ggcgaccacg cacgatgtga ccaccgaccg    18480
cagccagcgg ctgacgctgc gcttcgtgcc cgtggaccgc gaggacaaca cctactcgta   18540
caaagtgcgc tacacgctgg ccgtgggcga caaccgcgtg ctggacatgg ccagcaccta   18600
ctttgacatc cgcggcgtgc tggatcgggg ccctagcttc aaaccctact ccggcaccgc   18660
ctacaacagc ctggctccca agggagcgcc caattccagc cagtgggagc aaaaaaaggc   18720
aggcaatggt gacactatgg aaacacacac atttggtgtg gccccaatgg gcggtgagaa   18780
tattacaatc gacggattac aaattggaac tgacgctaca gctgatcagg ataaaccaat   18840
ttatgctgac aaaacattcc agcctgaacc tcaagtagga aagaaaatt ggcaagaaac    18900
tgaaagcttt tatgcgggta ggctcttaa aaaagacaca agcatgaaac cttgctatgg    18960
ctcctatgct agaccccacca atgtaaaggg aggtcaagct aaacttaaag ttggagctga   19020
tggagttcct accaaagaat tgacataga cctggctttc tttgatactc ccggtggcac    19080
agtgaatgga caagatgagt ataaagcaga cattgtcatg tataccgaaa acacgtatct   19140
ggaaactcca gacacgcatg tggtatacaa accaggcagg gatgatgcaa gttctgaaat   19200
taacctggtt cagcagtcca tgcccaatag acccaactat attgggttca gagacaacttc   19260
tattgggctc atgtattaca acagtactgg caatatgggg gtgctggctg tcaggcctc    19320
acagctgaat gctgtggtcg acttgcaaga cagaaacacc gagctgtcat accagctctt   19380
gcttgactct ttgggtgaca gaacccggta tttcagtatg tggaatcagg cggtggacag   19440
ttatgatcct gatgtgcgca ttattgaaaa ccatgtgtg aagacgaac ttcccaacta     19500
ttgcttcccc ctggatgggt ctggcactaa tgccgcttac caaggtgtga agtaaaaaa    19560
tggtaacgat ggtgatgttg agagcgaatg ggaaaatgat gatactgtcg cagctcgaaa   19620
tcaattatgc aagggcaaca tttttgccat ggaaattaac ctccaagcca acctgtggag   19680
aagtttcctc tactcgaacg tggcctgta cctgcccgac tcttacaagt acacgccagc    19740
caacatcacc ctgcccacca acaccaacac ttatgattac atgaacggga gagtggtgcc   19800
tcctcgctg gtggacgcct acatcaacat cggggcgcgc tggtcgctgg accccatgga    19860
caacgtcaat cccttcaacc accaccgcaa cgcgggcctg cgctaccgct ccatgctcct   19920
gggcaacgg cgctacgtgc ccttccacat ccaggtgccc cagaaatttt tcgccatcaa    19980
gagcctcctg ctcctgcccg gtcctacac ctacgagtgg aacttccgca aggacgtcaa    20040
catgatcctg cagagctccc tcggcaacga cctgcgcacg gacggggcct ccatctcctt   20100
caccagcatc aacctctacg ccaccttctt ccccatggcg cacaacacgg cctccacgct   20160
cgaggccatg ctgcgcaacg acaccaacga ccagtccttc aacgactacc tctcggcgac   20220
caacatgctc taccccatcc cggccaacgc caccaacgtg cccatctcca tcccctcgcg   20280
caactggggcc gccttccgcg gctggtcctt cacgcgcctc aagaccaagg agacgccctc   20340
gctgggctcc gggttcgacc cctacttcgt ctactcgggc tccatcccct acctcgacgg   20400
caccttctac ctcaaccaca ccttcaagaa ggtctccatc accttcgct cctccgtcag    20460
ctggcccggc aacgaccggc tcctgacgcc caacgagttc gaaatcaagc gcaccgtcga   20520
cggcgaggga tacaacgtgg cccagtgcaa catgaccaag gactggttcc tggtccagat   20580
gctggcccac tacaacatcg gctaccaggg cttctacgtg cccgagggct acaaggaccg   20640
catgtactcc ttcttccgca acttccagcc catgagccgc caggtggtgg acgaggtcaa   20700
ctacaaggac taccaggccg tcacccctgg cctaccagcac aacaactcgg gcttcgtcgg   20760
ctacctcgcg cccaccatgc gccagggcca gccctaccc gccaactacc cgtacccgct    20820
catcggcaag agcgccgtca ccagcgtcac ccagaaaag ttcctctgcg acagggtcat     20880
ggcgccatc cccttctcca gcaacttcat gtccatgggc gcgctcaccg acctcggcca    20940
gaacatgctc tatgccaact ccgcccacgc gctagacatg aatttcgaag tcgaccccat   21000
ggatgagtcc acccttctct atgttgtctt cgaagtcttc gacgtcgtcc gagtgcacca   21060
gccccaccgc ggcgtcatcg aggccgtcta cctgcgcacc cccttctcgg ccggtaacgc   21120
caccacctaa attgctactt gcatgatggc tgagcccaca ggctccggcg agcaggagct   21180
cagggccatc atccgcgacc tgggctgcgg gccctacttc ctgggcacct tcgataagcg   21240
cttcccggga ttcatggccc cgcacaagct ggcctgcgcc atcgtcaaca cggccggccg   21300
cgagaccggg ggcgagcact ggctggcctt cgcctgaac ccgcgctcga cacctgcta    21360
cctcttcgac cccttcggt tcggaacgac gcgcctcaag cagatctacc agttcgtaga    21420
cgagggccg ctgcgccgta ggccctggc caccgaggac cgctgcgtca ccctggaaaa    21480
gtccaccag accgtgcagg tccgcgctc ggccgcctgc gggctcttct gctgcatgtt     21540
cctgcacgcc ttcgtgcact ggcccgaccg cccatggac aagaaccca ccatgaactt     21600
gctgacgggg gtgcccaacg gcatgctcca gtcgccccag gtggaaccca ccctgcgccg    21660
caaccaggag gcgctctacc gcttcctcaa ctcccactcc gcctacttc gctcccaccg    21720
cgcgcgcatc gagaaggcca ccgcttcga ccgcatgacc aatcaagaca tgtaaaccgt    21780
gtgtgtatgt ttaaaatatc ttttaataaa cagcacttta atgttacaca tgcatctgag   21840
atgattttat tttagaaatc gaaagggttc tgccgggtct cggcatggcc cgcgggcagg   21900
gacacgttgc ggaactggta cttggccagc cacttgaact cggggatcag cagtttgggc   21960
agcggggtgt cggggaagga gtcggtccac agcttccgcg tcagctgcag ggcgcccagc   22020
aggtcggggc cggagatctt gaaatcgcag tgggacccg cgttctgcgc ggagagttg    22080
cggtacacgg ggttcagcca ctggaacacc atcagggccg ggtgcttcac gctcgccagc   22140
accgccgcgt cggtgatgct ctccacgtcg aggtcctcgg cgttggccat cccgaagggg   22200
gtcatcttgc aggtctgcct tcccatggtg ggcacgcacc cgggcttgtg gttgcaatcg   22260
cagtgcaggg ggatcagcat catctgggcc tggtcggcgt tcatccccgg gtacatggcc   22320
ttcatgaaag cctccaattg cctgaacgcc tgctgggcct tggctccctc ggtgaagaag   22380
```

```
accccgcagg acttgctaga gaactggttg gtggcacagc cggcatcgtg cacgcagcag   22440
cgcgcgtcgt tgttggccag ctgcaccacg ctgcgcccc  agcggttctg ggtgatcttg   22500
gcccggtcgg ggttctcctt cagcgcgcgc tgcccgttct cgctcgccac atccatctcg   22560
atcatgtgct ccttctggat catggtggtc ccgtgcaggc accgcagttt gccctcggcc   22620
tcggtgcacc cgtgcagcca cagcgcgcac ccggtgcact cccagttctt gtgggcgatc   22680
tgggaatgcg cgtgcacgaa cccttgcagg aagcggccca tcatggtcgt cagggtcttg   22740
ttgctagtga aggtcaacgg gatgccgcgg tgctcctcgt tgatgtacag gtggcagatg   22800
cggcggtaca cctcgccctg ctcgggcatc agttggaagt tggctttcag gtcggtctcc   22860
acgcggtagc ggtccatcag catagtcatg atttccatgc ccttctccca ggcgagacg    22920
atgggcaggc tcatagggtt cttcaccatc atcttagcac tagcagccgc ggccagggag   22980
tcgctctcat ccagggtctc aaagctccgc ttgccgtcct tctcggtgat ccgcaccggg   23040
gggtagctga agcccacggc cgccagctcc tcctcggcct gtctttcgtc ctcgctgtcc   23100
tggctgacgt cctgcatgac cacatgcttg gtcttgcggg gtttcttctt gggcggcagt   23160
ggcggcggag atgcttgtgg cgagggggag cgcgagttct cgctcaccac tactatctct   23220
tcctcttctt ggtccgaggc cacgcggcgg taggtatgtc tcttcggggg cagaggcgga   23280
ggcgacgggc tctcgccgcc gcgacttggc ggatggctgg cagagcccct tccgcgttcg   23340
ggggtgcgct cccggcggcg ctctgactga cttcctccgc ggccggccat tgtgttctcc   23400
tagggaggaa caacaagcat ggagactcag ccatcgccaa cctcgccatc tgcccccacc   23460
gccggcgacg agaagcagca gcagcagaat gaaaagctta accgccccgcc gcccagcccc  23520
gcctccgacg cagccgcggt cccagacatg caagagatgg aggaatccat cgagattgac   23580
ctgggctatg tgacgcccgc ggagcatgag gaggagctgg cagtgcgctt tcaatcgtca   23640
agccaggaag ataaagaaca gccagagcag gaagcagaga acgagcagga tcagctggg   23700
ctcgagcatg gcgactacct ccacctgagc ggggaggagg acgcgctcat caagcatctg   23760
gcccggcagg ccaccatcgt caaggacgcg ctgctcgacc gcaccgaggt gcccctcagc   23820
gtggaggagc tcagccgcgc ctacgagctc aacctcttct cgccgcgcgt gccccccaag   23880
cgccagccca acggcacctg cgagcccaac ccccgcctca acttctaccc ggtcttcgcg   23940
gtgcccgagg ccctgccac  ctaccacatc tttttcaaga accaaaagat ccccgtctcc   24000
tgccgcgcca accgcacccg cgccgacgcc ctcttcaacc tgggtccggg cgcccgccta   24060
cctgatatcg cctccttgga agaggttccc aagatcttcg agggtctggg cagcgacgag   24120
actcgggccg cgaacgctct gcaaggagaa ggaggaggag agcatgagca ccacagccgc   24180
ctggtcgagt tggaaggcga caacgcgcgg ctggcggtgc tcaaacgcac ggtcgagctg   24240
acccatttcg cctacccggc tctgaacctg ccccccgaaag tcatgagcgc ggtcatggac   24300
caggtgctca tcaagcgcgc gtcgccatc  tccgaggacg agggcatgca agactccgag   24360
gagggcaagc ccgtggtcag cgacgagcag ctggcccggt ggctgggtcc taatgctacc   24420
cctcaaagtt tggaagagcg gcgcaagctc atgatggccg tggtcctggt gaccgtggga   24480
ctggagtgcc tgcgccgctt cttcgccgac gcggagaccc tgcgcaagct cgaggagaac   24540
ctgcactacc tcttcaggca cgggttcgtg cgccaggcct gcaagatctc caacgtggag   24600
ctgaccaacc tggtctccta catgggcatc ttgcacgaga accgcctggg gcagaacgtg   24660
ctgcacacca ccctgcgcgg ggaggcccgc cgcgactaca tccgcgactg cgtctacctg   24720
tacctctgcc acacctggca gacgggcatg ggcgtgtggc agcagtgtct ggaggagcag   24780
aacctgaaag agctctgcaa gctcctgcaa aagaacctca agggtctgtg gacccgggttc  24840
gacgagcgga ccaccgcctc ggacctggcc gacctcatct tccccgagcg cctcaggctg   24900
acgctgcgca acggcctgcc cgactttatg agccaaagca tgttgcaaaa ctttcgctct   24960
ttcatcctcg aacgctccgg aatcctgccc gccacctcgg ccgcgctgcc ctcggacttc   25020
gtgccgctga ccttccgcga gtgccccccg ccgctgtgga gccactgcta cctgctgcgc   25080
ctggccaact acctggccta ccactcggac gtgatcgagg acgtcagcgg cgagggcctg   25140
ctcgagtgcc actgccgctg caacctctgc acgccgcacc gctccctgcc ctgcaacccc   25200
cagctgctga gcgagaccca gatcatcggc accttcgagt tgcaagggcc cagcgagggc   25260
gagggagcca aggggggtct gaaactcacc ccggggctgt ggacctcggc ctacttgcgc   25320
aagttcgtgc ccgaggatta ccatcccttc gagatcaggt tctacgagga ccaatcccag   25380
ccgcccaagg ccgagctgtc ggcctgcgtc atcacccagg gggcgatcct ggcccaattg   25440
caagccatcc agaaatcccg ccaagaattc ttgctgaaaa agggccgcgg ggtctacctc   25500
gacccccaga ccggtgagga gctcaacccc ggcttccccc aggatgcccc gaggaaacaa   25560
gaagctgaaa gtggagctgc cgcccgtgga ggatttggag gaagactggg agaacagcag   25620
tcaggcagag gagatggagg aagactggga cagcactcag gcagaggagg acagcctgca   25680
agacagtctg gaggaagacg aggaggaggc agaggaggag gtggaagaag cagccgccgc   25740
cagaccgtcg tcctcggcgg gggagaaagc aagcagcacg gataccatct ccgctccggg   25800
tcggggtccc gctcggcccc acagtagatg ggacgagacc gggcgattcc cgaaccccac   25860
cacccagacc ggtaagaagg agcggcaggg atacaagtgc tggccgggcg acaaaaacgc   25920
catcgtctcc tgcttgcagg cctgcggggg caacatctcc ttcaccgggc gctacctgct   25980
cttccaccgc ggggtgaact tccccgcaa  catcttgcat tactaccgtc acctccacag   26040
ccctactac  ttccaagaag aggcagcagc agcagaaaaa gaccagaaaa ccagctagaa   26100
aatccacagc ggcggcagcg gcaggtggac tgaggatcgc ggcgaacgag ccggcgcaga   26160
cccgggagct cggaaccgg  atctttccca ccctctatgc catcttccag cagagtcggg   26220
ggcaggagca ggaactgaaa gtcaagaacc gttctctgcg ctcgctcacc cgcagttgtc   26280
tgtatcacaa gagcgaagac caacttcagc gcactctcga ggacgccgag gctctcttca   26340
acaagtactg cgcgctcact cttaaagagt agcccgcgcc cgcccagtcg cagaaaaagg   26400
cgggaattac gtcacctgtg cccttcgccc tagccgcctc cacccagcac cgccatgagc   26460
aaaagagattc ccacgccttt acatgtggagc taccagccgc agatgggcct ggccgccggc  26520
gccgccagg  actactccac ccgcatgaat tggctcagcg ccgggcccgc gatgatctca   26580
cggtgaatg  acatccgcgc ccaccgaaac cagatactcc tagaacagtc agcgctcacc   26640
gccacgcccc gcaatcacct caatccgcgt aattggcccg ccgccctggt gtaccaggaa   26700
attccccagc ccacgaccgt actacttccg cgagacgccc aggccgaagt ccagctgact   26760
aactcaggtg tccagctggc ggggcggcgc accctgctgc gtcaccgccc gctcagggt   26820
ataaagcggc tggtgatccg gggcagaggc acacagctca acgcgaggt  ggtgagctct   26880
tcgctgggtc tgcgacctga cggagtcttc caactcgccg gatcgggag  atcttccttc   26940
acgcctcgtc aggcggtcct gactttggag agttcgtcct cgcagcccg  ctcgggcggc   27000
atcggcactc tccagttcgt ggaggagttc actccctcgg tctacttcaa cccccttctcc   27060
ggctccccg  gccactaccc ggacgagttc atcccgaact ttgacgccat cagcgagtcg   27120
```

```
gtggacggct acgattgaat gtcccatggt ggcgcggctg acctagctcg gcttcgacac   27180
ctggaccact gccgccgctt tcgctgcttc gctcgggacc tcgccgagtt cacctacttt   27240
gagctgcccg aggagcatcc tcagggcccg gccacggag tgcggatcgt cgtcgaaggg    27300
ggcctagact cccacctgct tcggatcttc agccagcgcc cgatcctggt cgagcgccaa   27360
cagggcaaca ccctcctgac cctctactgc atctgcgaca accccggcc gcatgaaagt    27420
cttttgttgtc tgctgtgtac tgagtataat aaaagctgag atcagcgact actccggact  27480
caactgtggt gtttctgcat ccatcaatcg gtctctgacc ttcaccggga acgagaccga   27540
gctccaggtc cagtgtaagc cccacaagaa gtacctcacc tggctgtacc agggctcccc   27600
gatcgccgtt gttaaccact gcgacgacga cggagtcctg ctgaacggcc ccgccaacct   27660
tacttttttcc acccgcagaa gcaagctact gctcttccga cccttcctcc ccggcaccta  27720
tcagtgcatc tcgggaccct gccatcacac cttccacctg atcccgaata ccacctcttc   27780
cccagcaccg ctccccacta caaccaaac taaccaccac caacgctacc gacgcgacct    27840
cgtttctgaa tctaatacca cccaccggg aggtgagctc cgaggtcgca aaccctctgg    27900
gatttattac ggcccctggg aggtggtggg gttaatagct ttaggcttag tggcgggtgg   27960
gcttttggct ctctgctacc tatacctccc ttgcttttcc tacttagtgg tgctttgttg   28020
ctggtttaag aaatggggaa gatcacccta gtgtgcggtg tgctggtgac ggtggtgctt   28080
tcgattctgg gaggggaag cgcggctgta gtgacggaga agaaggccga tccctgcttg    28140
acttttcaacc ccgataaatg ccggctgagt tttcagcccg atggcaatcg gtgcgcggtg   28200
ttgatcaagt gcggatggga atgcgagagc gtgttggtcc agtataaaaa caagacctgg   28260
aacaatactc tcgcgtccac atggcagccc ggggaccccg agtggtacac cgtctctgtc   28320
cctggtgctg acggctccct ccgcacggtg aacaacactt tcatttttga gcacatgtgc   28380
gagaccgcca tgttcatgag caagccgtac ggtatgtgcc ccccacgtga agagaatatc   28440
gtggtcttct ccatcgctta cagcgcgtgc acggtgctaa tcaccgcgat cgtgtgcctg   28500
agcattcaca tgctcatcgc tattcgcccc agaataatg ccgagaaaga gaaacagcca    28560
taacacactt ttcacatacc tttttcagac catggcctct gttacaatcc ttatttattt   28620
tttgggactt gtgggcacta gcagcacttt tcagcatata aacaaaactg tttatgctgg   28680
ttcaaattct gtgttagctg gacatcagtc ataccagaaa gtttcatggt actggtatga   28740
taaaaatcaa acaccccgtta cactctgcaa gggtccacaa cagcccgtaa accgtagtgg   28800
gattttttttt agctgtaatc ataataatat cacactactt tcaattacaa agcactatgc   28860
tggaacttac tatggaacca atttcaatat caaacatgac ttactata gtgtcagagt     28920
attggatcca actacccta gaacaactac aaagcccacc acaactaaga agcccactac    28980
acctaagaag cctaccacgc ccaaaaccac taagacaact actaagacca ctaccacaga   29040
gccaaccaca accagcaccc acacttgcta taactacaca cacacacaca cactgagctg   29100
acctcacagg caactactga aaaatggttt gccctgttac aaaaggggga aaacagtagc   29160
agcagtcctc tgcctaccac ccccagtgag gaaataccta aatccatggt tggcattatc   29220
gctgctgtag tggtgtgtat gctgattatc atcttgtgca tgatgtacta tgcctgctac   29280
tacagaaaac acaggctgaa caacaagctg gaccccctac tgaatgttga ttttttaattt   29340
tttagaacca tgaagatcct aagccttttt tgtttttcta taattattac ctctgctatt  29400
tgtaactcag tggataagga cgttactgtc accactggct ctaattatac actgaaagga   29460
cctccctcag gtatgctttc gtggtattgc tatttttggaa ctgatgtttc acaaactgaa   29520
ttgtgtaatt ttcaaaaagg caaaacccaa aatcctaaaa ttcataacta tcaatgcaat   29580
ggtactgatt tagtactgtt caatatcacg aaaacatatg ctggaagtta ttactgcccg   29640
ggagataatg ttgacaatat gattttttac gaattacaag tagttgatcc cactactcca   29700
gcaccaccca cccacaactac caaggcacat agcacagaca cacaggaaaac cactccagag   29760
gcagaagtag cagagttagc aaagcagatt catgaagatt cctttgttgc caatacccc    29820
acacaccccg gaccgcaatg tccagggcca ttagtcagcg gcattgtcgg tgtgctttgc   29880
gggttagcag ttataatcat ctgcatgttc attttttgct gctgctacag aaggcttcac   29940
cgacaaaaaat cagacccact gctgaacctc tatgtttaat ttttgatttt ccagagccat   30000
gaaggcactt agcactttag tttttttgac cttgattggc attgttttta atagtaaaat   30060
taccagggtt agctttctca aacatgttaa tgttactgaa ggaaataata tcacactagt   30120
aggtgtagaa ggtgctcaaa acaccacctg gacaaaatac catctcgggt ggaaagatat   30180
ttgcacctgg aatgtcactt attttttgcat aggagttaat cttaccattg ttaatgctaa   30240
tcaatctcag aatggattaa ttaaagggca gagcgtgagt gttaccagtg atgggtacta   30300
tacccagcat aatttcaact acaacattac tgttatacca ctgccaacac ctagcccacc   30360
tagcactact cagaccacac aaaaaactca cactacacag agctccacaa ctaccatgca   30420
gaccactcag acaaccacat acactacttc ccctcagccc accaccacta cagcagaggc   30480
gagtagctca cccaccatca aagtggcatt tttaatgctg gccccatcta gcagtccac    30540
tgctagtacc aatgagcaga ctactgaatt tttgtccact attcagagca gcaccacagc   30600
tacctcgagt gccttctcta gcaccgccaa tctcacctcg ctttcctcta tgccaatcag   30660
taatgctact accctccccg ctcctctttcc cactcctctg aagcaatccg agtccagcac   30720
gcagctgcag atcaccctgc tcattgtgat cggggtggtc atcctggcag tgctgctcta   30780
ctttatcttc tgccgtcgca tccccaacgc aaagccggcc tacaagccca ttgttatcgg   30840
gacgccggag ccgcttcagg tggagggagg tctaaggaat cttctcttct cttttacagt   30900
atggtgattt gaactatgat tcctagacat ttcattatca cttctctaat ctgtgtgctc   30960
caagtctgtg ccaccctcgc tctcgtggct aacgcgagtc cagactgcat ggagcgttc    31020
gcctcctacg tgctctttgc cttcatcacc tgcatctgct gctgtagcat agtctgcctg   31080
cttatcacct tcttccagtt cgttgactgg gtctttgtgc gcatcgccta cctgcgccac   31140
caccccagt accgcgacca gagagtggcg caactgttga gactcatctg atgataagca   31200
tgcgggtctct gctactactt ctcgcgcttc tgctagctcc cctcgccgcc cccctatccc  31260
tcaaatcccc cacccagtcc cctgaagagg ttcgaaaatg taaattccaa gaaccctgga   31320
aattcctttc atgctacaaa ctcaaatcag aaatgcaccc cagctggatc atgatcgttg   31380
gaatcgtgaa catccttgcc tgtacctct tctcctttgt gatttacccc cgctttgact    31440
ttgggtggaa cgcacccgag gcgctctggc tcccgctga tcccgacaca ccaccacagc   31500
agcagcagca aaatcaggca caggcacacg caccaccaca gctaggcca caatacatgc    31560
ccatcttaaa ctatgaggcc gaggcacagc gagccatgct tcctgctatt agttacttca   31620
atctaaccgg cggagatgac tgaccccatg gccaacaaca ccgtcaacga cctcctggac   31680
atggacggcc gcgcctcgga gcagcgactc gcccaactcc gcatccgcca gcagcaggag   31740
agagccgtca aggagctgca ggatgcggtg gccatccacc agtgcaagag aggcatcttc   31800
tgcctggtga agcaggccaa gatctccttc gaggtcacgt ccaccgacca tcgcctctcc   31860
```

```
tacgagctcc tgcagcagcg ccagaagttc acctgcctgg tcggagtcaa ccccatcgtc   31920
atcacccagc agtctggcga taccaagggt tgcatccact gctcctgcga ctcccccgag   31980
tgcgttcaca ccctgatcaa gaccctctgc ggcctccgcg acctcctccc catgaactaa   32040
tcaactaacc ccctacccct ttaccctcca gtaaaaataa agattaaaaa tgattgaatt   32100
gatcaataaa gaatcactta cttgaaatct gaaaccaggt ctctgtccat gttttctgtc   32160
agcagcactt cactcccctc ttcccaactc tggtactgca ggcccggcg ggctgcaaac    32220
ttcctccaca ctctgaaggg gatgtcaaat tcctcctgtc cctcaatctt cattttatc    32280
ttctatcaga tgtccaaaaa gcgcgcgcgg gtggatgatg gcttcgaccc cgtgtacccc   32340
tacgatgcag acaacgcacc gactgtgccc ttcatcaacc ctcccttcgt ctcttcagat   32400
ggattccaag aaaagcccct gggggtgttg tccctgcgac tggccgaccc cgtcaccacc   32460
aagaatgggg ctgtcaccct caagctgggg gaggggggtgg acctcgacga ctcgggaaaa   32520
ctcatctcca aaaatgccac caaggccact gcccctctca gtatttccaa cggcaccatt   32580
tcccttaaca tggctgcccc ttttacaac aacaatggaa cgttaagtct caatgtttct    32640
acaccattag cagtatttcc cacttttaac actttaggta tcagtcttgg aaacggtctt   32700
caaacttcta ataagttgct gactgtacag ttaactcatc ctcttacatt cagctcaaat   32760
agcatcacag taaaaacaga caaaggactc tatattaatt ctagtggaaa cagagggctt   32820
gaggctaaca taagcctaaa aagaggactg attttttgatg gtaatgctat tgcaacatac   32880
cttggaagtg gtttagacta tggatcctat gatagcaggt ggaaaacaag acccatcatc   32940
accaaaattg gagcaggttt gaattttgat gctaataatg ccatggctgt gaagctaggc   33000
acaggtttaa gttttgactc tgccggtgcc ttaacagctg gaaacaaaga ggatgacaag   33060
ctaacacttt ggactacacc tgacccaagc cctaattgtc aattactttc agacagagat   33120
gccaaattta cccctatgct tacaaaatgc ggtagtcaaa tactaggcac tgttgcagta   33180
gctgctgtta ctgtaggttc agcactaaat ccaattaatg acacagtaaa aagcgccata   33240
gtattcctta gatttgactc tgacggtgtg ctcatgtcaa actcatcaat ggtaggtgat   33300
tactggaact ttagggaagg acagaccacc caaagtgtgg cctatacaaa tgctgtggga   33360
ttcatgccca atctaggtgc atatcctaaa acccaaagca aaacaccaaa aaatagtata   33420
gtaagtcagg tatatttaaa tggagaaact actatgccaa tgacactgac aataactttc   33480
aatggcactg atgaaaaaga cacaacaccct gtgagcactt actccatgac ttttacatgg   33540
cagtggactg gagactataa ggacaagaat attacctttg ctaccaactc ctttactttc   33600
tcctacatgg cccaagaata aaccctgcat gccaacccca ttgttcccac cactatggaa   33660
aactctgaag cagaaaaaaa taaagttcaa gtgtttttatt gattcaacag ttttcacaga   33720
attcgagtag ttatttccc tcctccctcc caactcatgg aatacaccac cctctcccca   33780
cgcacagcct taaacatctg aatgccattg gtaatggaca tggttttggt ctccacattc   33840
cacacagttt cagagcgagc cagtctcggg tcggtcaggg agatgaaacc ctccgggcac   33900
tcctgcatct gcacctcaaa gttcagtagc tgaggggctgt cctcggtggt cgggatcaca   33960
gttatctgga agaagagcgg tgagagtcat aatccgcgaa cgggatcggg cggttgtggc   34020
gcatcaggcc ccgcagcagt cgctgtctgc gccgctccgt caagctgctg ctcaagggggt   34080
ctgggtccag ggactccctg cgcatgatgc cgatggccct gagcatcagt cgcctggtgc   34140
ggcgggcga gcagcggatg cggatctcac tcaggtcgga gcagtacgtg cagcacagca   34200
ctaccaagtt gttcaacagt ccatagttca acgtgctcca gccaaaactc atctgtggaa   34260
ctatgctgcc cacatgtcca tcgtaccaga tcctgatgta aatcaggtgg cgccccctcc   34320
agaacacact gcccatgtac atgatctcct tgggcatgtg caggttcacc acctcccggt   34380
accacatcac ccgctggttg aacatggcac cctggataat cctgcggaac cagatgccca   34440
gcaccgcccc gcccgccatg cagcgcaggg acccccgggtc ctggcaatgg cagtggagca   34500
cccaccgctc acgcgcgtgg attaactggg agctgaacaa gtctatgttg gcacagcaca   34560
ggcacacgct catgcatgtc ttcagcactc tcagttcctc gggggtcagg accatgtccc   34620
agggcagggg gaactcttgc aggacagtga acccggcagg acggggcctc cctcgcacac   34680
aacttacatt gtgcatggac agggtatcgc aatcaggcag caccggatga tcctccacca   34740
gagaagcgcg ggtctcggtc tcctcacagc gaggtaaggg ggccggcggt tggtacggat   34800
gatggcggga tgacgctaat cgtgttctgg atcgtgtcat gatggagctg tttcctgaca   34860
ttttcgtact tcacgaagca gaacctggta cgggcactgc acaccgctcg ccggcgacgg   34920
tctcggcgct tcgagcgctc ggtgttgaag ttatagaaca gccactccct cagagcgtgg   34980
agtatctcct gagcctcttg ggtgatgaaa atcccatccg ctctgatggc tctgatcaca   35040
tcggccacgg tggaatgggc cagacccagc cagatgatgc aatttttgttg ggtttcggtg   35100
acggagggag agggaagaac aggaagaacc atgattaact ttattccaaa cggtctcgga   35160
gcacttcaaa atgcaggtcc cggaggtggc acctctcgcc cccactgtgt tggtggaaaa   35220
taacagccag gtcaaaggtg acacggttct cgagatgttc cacggtggct tccagcaaag   35280
cctccacgcg cacatccaga aacaagagga cagcgaaagc gggagcgttt tctaattcct   35340
caatcatcat attacactcc tgcaccatcc ccagataatt ttcatttttc cagccttgaa   35400
tgattcgtat tagttcctga ggtaaatcca agccagccat gataaaaagc tcgcgcagag   35460
cgccctccac cggcattctt aagcacaccc tcataattcc aagagattct gctcctggtt   35520
cacctgcagc agattaacaa tgggaatatc aaaatctctg ccgcgatccc taagctcctc   35580
cctcaacaat aactgtatgt aatctttcat atcatctccg aaattttag ccataggggcc   35640
gccaggaata agagcagggc aagccacatt acagataagg cgaagtcctc cccagtgatt   35700
attgccaaat gtaagattga aataagcatg ctggctagac cctgtgatat cttccagata   35760
actggacaga aaatcaggca agcaattttt aagaaaatca acaaaagaaa agtcgtccag   35820
gtgcaggttt agagcctcag gaacaacgat ggaataagtg caaggagtgc gttccagcat   35880
ggttagtgtt tttttggtga tctgtagaac aaaaaataaa catgcaatat taaaccatgc   35940
tagcctggcg aacaggtggg taaatcactc tttccagcac caggcaggct acggggtctc   36000
cggcgcgacc ctcgtagaag ctgtcgccat gattgaaaag catcaccgag agaccttccc   36060
ggtggccggc atggatgatt cgagaagaag catacactcc gggaacattg gcatccgtga   36120
gtgaaaaaaa gcgacctata aagcctcggg gcactacaat gctcaatctc aattccagca   36180
aagccacccc atgcggatgg agcacaaaat tggcaggtgc gtaaaaaatg taattactcc   36240
cctcctgcac aggcagcaaa ccccccgctc cctccagaaa cacatcacaaa gcctcagcgt   36300
ccatagctta ccgagcacgg caggcgcaag agtcagagaa aaggctgagc tctaacctga   36360
ctgcccgctc ctgtgctcaa tatatagccc taacctacac tgacgtaaag gccaaagtct   36420
aaaaatacccc gccaaaatga cacacacgcc cagcacacgc ccagaaaccg gtgacacact   36480
caaaaaaata cgtgcgcttc ctcaaacgcc caaaccggcg tcatttccgg gttcccacgc   36540
tacgtcaccg ctcagcgact ttcaaattcc gtcgaccgtt aaaaacgtca ctcgcccgc    36600
```

```
cctaacggt cgccttctc tcggccaatc accttcctcc cttcccaaat tcaaacgcct    36660
catttgcata ttaacgcgca caaaaagttt gaggtatata tttgaatgat g           36711

SEQ ID NO: 7           moltype = AA  length = 114
FEATURE                Location/Qualifiers
source                 1..114
                       mol_type = protein
                       organism = synthetic construct
REGION                 1..114
                       note = Human adenovirus AdHu5
SEQUENCE: 7
MVLPALPAPP VCDSQNECVG WLGVAYSAVV DVIRAAAHEG VYIEPEARGR LDALREWIYY    60
NYYTERSKRR DRRRRSVCHA RTWFCFRKYD YVRRSIWHDT TTNTISVVSA HSVQ         114

SEQ ID NO: 8           moltype = AA  length = 294
FEATURE                Location/Qualifiers
source                 1..294
                       mol_type = protein
                       organism = synthetic construct
REGION                 1..294
                       note = Human adenovirus AdHu5
SEQUENCE: 8
MTTSGVPFGM TLRPTRSRLS RRTPYSRDRL PPFETETRAT ILEDHPLLPE CNTLTMHNVS    60
YVRGLPCSVG FTLIQEWVVP WDMVLTREEL VILRKCMHVC LCCANIDIMT SMMIHGYESW   120
ALHCHCSSPG SLQCIAGGQV LASWFRMVVD GAMFNQRFIW YREVVNYNMP KEVMFMSSVF   180
MRGRHLIYLR LWYDGHVGSV VPAMSFGYSA LHCGILNNIV VLCCSYCADL SEIRVRCCAR   240
RTRRLMLRAV RIIAEETTAM LYSCRTERRR QQFIRALLQH HRPILMHDYD STPM         294

SEQ ID NO: 9           moltype = AA  length = 150
FEATURE                Location/Qualifiers
source                 1..150
                       mol_type = protein
                       organism = synthetic construct
REGION                 1..150
                       note = Human adenovirus AdHu5
SEQUENCE: 9
MTTSGVPFGM TLRPTRSRLS RRTPYSRDRL PPFETETRAT ILEDHPLLPE CNTLTMHNAW    60
TSPSPPVKQP QVGQQPVAQQ LDSDMNLSEL PGEFINITDE RLARQETVWN ITPKNMSVTH   120
DMMLFKASRG ERTVYSVCWE GGGRLNTRVL                                    150

SEQ ID NO: 10          moltype = DNA  length = 30842
FEATURE                Location/Qualifiers
misc_feature           1..30842
                       note = Viral vector based on Chimpanzee adenovirus C68
source                 1..30842
                       mol_type = other DNA
                       organism = synthetic construct
SEQUENCE: 10
ccatcttcaa taatatacct caaacttttt gtgcgcgtta atatgcaaat gaggcgtttg     60
aatttgggga ggaagggcgg tgattggtcg agggatgagc gaccgttagg ggcggggcga   120
gtgacgtttt gatgacgtgg ttgcgaggag gagccagttt gcaagttctc gtgggaaaag   180
tgacgtcaaa cgaggtgtgg tttgaacacg gaaatactca атттттcccgc gctctctgac   240
aggaaatgag gtgtttctgg gcggatgcaa gtgaaaacgg gccattttcg cgcgaaaact   300
gaatgaggaa gtgaaaatct gagtaatttc gcgттттaтgg caggagggag tatttgccga   360
gggccgagta gactttgacc gattacgtgg gggtttgtat taccgtgttt ттcacccтaaa  420
ttccgcgta cggtgtcaaa gtccggtgtt tttacgcgat cgctagcgac atcgatcaca   480
agtttgtaca aaaaagctga acgagaaacg taaaatgata taaatatcaa tatattaaat   540
tagattttgc ataaaaaaca gactacataa tactgtaaaa cacaacatat ccagtcacta   600
tggcggccgc cgatttattc aacaaagcca cgttgtgtct caaaatctct gatgttacat   660
tgcacaagat aaaaatatat catcatgaac aataaaactg tctgcttaca taaacagtaa   720
tacaaggggt gttatgagcc atattcaacg ggaaacgtct tgctcgaggc cgcgattaaa   780
ttccaacatg gatgctgatt tatatgggta taaatgggct cgtgataatg tcgggcaatc   840
aggtgcgaca atctatcgat tgtatgggaa gcccgatgcg ccagatttgt ттстgaaaaca   900
tggcaaaggt agcgttgcca atgatgttac agatgagatg gtcagactaa actggctgac   960
ggaatttatg ccтстттccga ccatcaagca ttttatccgt actcctgatg atgcatggtt  1020
actcaccact gcgatccccg ggaaaacagc attccaggta ttagaagaat atcctgattc  1080
aggtgaaaat attgttgatg cgctggcagt gttcctgcgc cggttgcatt cgattcctgt  1140
ttgtaattgt cстттттaaca gcgatcgcgt atttcgtctc gctcaggcgc aatcacgaat  1200
gaataacggt ttggttgatg cgagtgattt tgatgacgag cgtaatggct ggcctgttga  1260
acaagtctgg aaagaaatgc aтaagcттттт gccattctca ccggattcag tcgtcactca  1320
tggtgatttc tcacttgata accttatttt tgacgagggg aaattaatag gttgtattga  1380
tgttggacga gtcggaatcg cagaccgata ccaggatctt gccatcctat ggaactgcct  1440
cggtgagttt tctccttcat tacagaaacg cttttttcaa aaatggta ttgataatcc  1500
tgatatgaat aaattgcagt ттcaттттgaт gctcgatgag tttttctaat cagaattggt  1560
taattggttg taacactggc acgcgtggat ccggcttact aaaagccaga taacagtatg  1620
cgtatttgcg cgctgatttt tgcggtataa gaatatatac tgatatgtat accccgaagтa  1680
tgtcaaaaag aggттaтgcтa tgaagcagcg tattacagtg acagttgaca gcgacagcta  1740
tcagttgctc aaggcatata tgatgtcaat atctccggtc tggtaagcac aaccatgcag  1800
aatgaagccc gtcgtctgcg tgccgaacgc tggaaagcgg aaaatcagga agggatggct  1860
```

```
gaggtcgccc ggtttattga aatgaacggc tcttttgctg acgagaacag gggctggtga  1920
aatgcagttt aaggtttaca cctataaaag agagagccgt tatcgtctgt ttgtggatgt  1980
acagagtgat attattgaca cgcccgggcg acggatggtg atcccctgg ccagtgcacg  2040
tctgctgtca gataaagtct cccgtgaact ttacccggtg gtgcatatcg gggatgaaag  2100
ctggcgcatg atgaccaccg atatggccag tgtgccgatc tccgttatcg ggaagaagt   2160
ggctgatctc agccaccgcg aaaatgacat caaaaacgcc attaacctga tgttctgggg  2220
aatataaatg tcaggctccc ttatacacag ccagtctgca ggtcgaccat agtgactgga  2280
tatgttgtgt tttacagtat tatgtagtct gttttttatg caaaatctaa tttaatatat  2340
tgatatttat atcattttac gtttctcgtt cagctttcct gtacaaagtg gtgatcgatt  2400
cgacagatcg cgatcgcaag tgagtagtgt tctggggcgg gggaggacct gcatgagggc  2460
cagaataact gaaatctgtg cttttctgtg tgttgcagca gcatgagcgg aagcggctcc  2520
tttgagggag gggtattcag cccttatctg acggggcgtc tcccctcctg ggcgggagtg  2580
cgtcagaatg tgatgggatc cacggtggac ggccggcccg tgcagcccgc gaactcttca  2640
accctgacct atgcaaccct gagctcttcg tcgttggacg cagctgccgc cgcagctgct  2700
gcatctgccg ccagcgccgt gcgcggaatg gccatgggcg ccggctacta cggcactctg  2760
gtggccaact cgagttccac caataatccc gccagcctga acgaggagaa gctgttgctg  2820
ctgatggccc agctcgaggc cttgacccag cgcctgggcg agctgaccca gcaggtggct  2880
cagctgcagg agcagacgcg ggccgcgggt gccacggtga aatccaaata aaaaatgaat  2940
caataaataa acgagacggt tgttgattt taacacagag tctgaatctt tatttgattt   3000
ttcgcgcgcg gtaggccctg gaccaccggt ctcgatcatt gagcaccggg tggatctttt  3060
ccaggacccg gtagaggtgg gcttggatgt tgaggtacat gggcatgagc ccgtcccggg  3120
ggtggaggta gctccattgc agggcctcgt gctcgggggt ggtgttgtaa atcacccagt  3180
catagcaggg gcgcagggca tggtgttgca caatatcttt gaggaggaga ctgatgccca  3240
cgggcagccc tttggtgtag gtgtttacaa atctgttgag ctgggaggga tgcatgcggg  3300
gggagatgag gtgcatcttg gcctggatct tgagattggc gatgttaccg cccagatccc  3360
gcctgggggtt catgttgtgc aggaccacca gcacggtgta tccggtgcac ttggggaatt  3420
tatcatgcaa cttggaaggg aaggcgtgaa agaatttggc gacgcctttg tgcccgccca  3480
ggttttccat gcactcatcc atgatgatgg cgatgggccc gtgggcggcg gcctgggcaa  3540
agacgtttcg ggggtcggac acatcatagt tgtggtcctg ggtgaggtca tcataggcca  3600
ttttaatgaa tttggggcgg aaggtgccgg actggggggac aaaggtaccc tcgatcccgg  3660
gggcgtagtt cccctcacag atctgcatct cccaggcttt gagctcggag ggggggatca  3720
tgtccacctg cggggcgata agaacacgg tttccgggc gggggagatg agctgggccg   3780
aaagcaagtt ccggagcagc tgggacttgc cgcagccggt ggggcgtag atgacccga    3840
tgaccggctg caggtggtag ttgagggaga gacagctgcc gtcctcccgg aggagggggg  3900
ccacctcgtt catcatctcg cgcacgtgca tgttctccgcg caccagttcc gccaggaggc  3960
gctctccccc cagggatagg agctcctgga gcgaggcgaa gttttttcagc ggcttgagtc  4020
cgtcggccat gggcattttg gagagggttt gttgcaagag ttccaggcgg tcccagagct  4080
cggtgatgtg ctctacggca tctcgatcca gcagacctcc tcgtttcgcg ggtttgggacg  4140
gctgcgggga tagggcacca gacgatgggc gtccagcgca gccaggggtcc ggtccttcca  4200
gggtcgcagc gtccgcgtca gggtggtctc cgtcacggtg aagggggtgcg cgccgggctg  4260
ggcgcttgcg agggtgcgct tcaggctcat ccggctggtc gaaaaccgct cccgatcggc  4320
gccctgcgcg tcggccaggt agcaattgac catgagttcg tagttgagcg cctcggccgc  4380
gtggccttttg gcgcggagct tacctttgga agtctgcccg gagcgggac agaggaggga  4440
cttgagggcg tagagcttgg gggcgaggaa gacggactcg ggggcgtagg cgtccgcgcc  4500
gcagtgggcg cagacggtct cgcactccac gagccaggtg aggtcgggct ggtcgggtc    4560
aaaaaccagt ttcccgccgt tcttttttgat gcgtttcttta cctttggtct ccatgagctc  4620
gtgtccccgc tgggtgacaa agaggctgtc cgtgtccccg tagaccgact ttatgggccg    4680
gtcctcgagc ggtgtgccgc ggtcctcctc gtagacgaac cccgcccact ccgagacgaa    4740
agcccggggtc caggccagca cgaaggaggc cacgtgggac gggtagcggt cgttgtccac    4800
cagcgggtcc acctttttcca gggtatgcaa acacatgtcc ccctcgtcca catccaggaa    4860
ggtgattggc ttgtaagtga aggccacgtg accgggggtc ccggccgggg gggtatataa    4920
gggtgcgggt ccctgctcgt cctcactgtc ttccggatcg ctgtccagga gcgccagctg    4980
ttggggtagg tattccctct cgaaggcggg catgacctcg gcactcaggt tgtcagtttc    5040
tagaaacgag gaggatttga tattgacggt gccggcggag atgcctttca agagcccctc    5100
gtccatctgg tcagaaaaga cgatcttttt gttgtcggac ttggtggcga aggagccgta    5160
gagggcgttg gagaggagct tggcgatgga gcgcatggtc tggttttttt ccttgtcggc    5220
gcgctccttg gcggcgatgt tgagctgcac gtactcgcgc gccacgcact tccattcggg    5280
gaagacggtg gtcagctcgt cgggcacgat tctgacctgc cagcccgat tatgcagggt     5340
gatgaggtcc acactggtgg ccacctcgcc gcgcaggggc tcattagtcc agcagaggcg     5400
tccgcccttg cgcgagcaga aggggggcag ggggtccagc atgacctcgt cgggggggtc     5460
ggcatcgatg gtgaagatgc cggggcaggag gtcgggggtca aagtagctga tggaagtggc     5520
cagatcgtcc agggcagctt gccattcgcg cacggccagc gcgcgctcgt agggactgag     5580
gggcgtgccc cagggcatgg gatgggtaag cgcggaggcg tacatgccgc agatgtcgta     5640
gacgtagagg ggctcctcga ggatgccgat gtaggtgggg tagcagcgcc ccccgaggat     5700
gctggcgcgc acgtagtcat acagctcgtg cgaggggggcg aggagcccg ggcccaggtt     5760
ggtgcgactg gcttttcgg cgcggtagac gatctggcgg aaaatggcat gcgagttgga     5820
ggagatggtg ggcttttgga agatgttgaa gtgggcgtgg ggcagtccga ccgagtcgcg     5880
gatgaagtgg gcgtaggagt cttgcagctt ggcgacgagc tcggcggtga ctaggacgtc     5940
cagagcgcag tagtcgaggg tctcctggat gatgtcatac ttgagctgtc cctttttgttt     6000
ccacagctcg cggttgagaa ggaactcttc gcggtcctt cagtactctt cgagggggaa     6060
cccgtcctga tctgcacggt aagagcctag catgtagaac tggttgacgg ccttgtaggc     6120
gcagcagccc ttctccacgg ggagggcgta ggcctgggcg ccttgcgca gggaggtgtg     6180
cgtgagggcg aaagtgtccc tgaccatgac cttgaggaac tggtgcttga agtcgatatc     6240
gtcgcagccc ccctgctccc agagctggaa gtccgtgcc ttcttgtagg cggggttggg     6300
caaagcgaaa gtaacatcgt tgaagaggat cttgcccgcg cgggggcataa agttgcgagt    6360
gatgcggaaa ggttggggca cctcggcccg gttgttgatg acctgggcgg cgagcacgat    6420
ctcgtcgaag ccgttgatgt tgtggcccac gatgtagagt tccacgaatc gcggacggcc    6480
cttgacgtgg ggcagtttct tgagctcctc gtaggtgagc tcgtcgggt cgctgagccc    6540
gtgctgctcg agcgcccagt cggcgagatg ggggttggcg cggaggaagg aagtccagag    6600
```

```
atccacggcc agggcggttt gcagacggtc ccggtactga cggaactgct gcccgacggc   6660
cattttttcg ggggtgacgc agtagaaggt gcggggtgtcc ccgtgccagc gatcccattt   6720
gagctggagg gcgagatcga gggcgagctc gacgagccgg tcgtcccegg agagtttcat   6780
gaccagcatg aaggggacga gctgcttgcc gaaggacccc atccaggtgt aggtttccac   6840
atcgtaggtg aggaagagcc tttcggtgcg aggatgcgag ccgatgggga agaactggat   6900
ctcctgccac caattggagg aatggctgtt gatgtgatgg aagtagaaat gccgacggca   6960
cgccgaacac tcgtgcttgt gtttatacaa gcggccacag tgctcgcaac gctgcacggg   7020
atgcacgtgc tgcacgagct gtacctgagt tcctttgacg aggaatttca gtgggaagtg   7080
gagtcgtggc gcctgcatct cgtgctgtac tacgtcgtgg tggtcggcct ggccctcttc   7140
tgcctcgatg gtggtcatgc tgacgagccc gcgcgggagg caggtccaga cctcggcgcg   7200
agcgggtcgg agagcgagga cgagggcgcg caggccggag ctgtccaggg tcctgagacg   7260
ctgcggagtc aggtcagtgg gcagcggcgg cgcgcggttg acttgcagga gttttttccag  7320
ggcgcgcggg aggtccagat ggtacttgat ctccaccgcg ccattggtgg cgacgtcgat   7380
ggcttgcagg gtcccgtgcc cctggggtgt gaccaccgtc ccccgttttct tcttgggcgg   7440
ctggggcgac gggggcggtg cctcttccat ggttagaagc ggcggcgagg acgcgcgccg   7500
ggcggcaggg gcggctcggg gcccggaggc aggggcggca ggggcacgtc ggcgccgcgc   7560
gcgggtaggt tctggtactg cgcccggaga agactggcgt gagcgacgac gcgacggttg   7620
acgtcctgga tctgacgcct ctgggtgaag gccacgggac ccgtgagttt gaacctgaaa   7680
gagagttcga cagaatcaat ctcggtatcc ttgacggcgg cctgccgcag gatctcttgc   7740
acgtcgcccg agttgtcctg gtaggcgatc tcggtcatga actgctcgat ctcctcctct   7800
tgaaggtctc cgcggccggc gcgctccacg gtggccgcga ggtcgttgga gatgcggccc   7860
atgagctgcg agaaggcgtt catgcccgcc tcgttccaga cgcggcgtga gaccacgacg   7920
ccctcgggat cgccgcgcgc catgaccacc tgggcgaggt tgagctccac gtggcgcgtg   7980
aagaccgcgt agttgcagag gcgctggtag aggtagttga gcgtggtggc gatgtgctcg   8040
gtgacgaaga aatacatgat ccagcggcgg agcggcatct cgctgacgtc gcccagcgcc   8100
tccaaacgtt ccatggcctc gtaaaagtcc acggcgaagt tgaaaaactg ggagttgcgc   8160
gccgagacgg tcaactcctc ctccagaaga cggatgagct cggcgatggt ggcgcgcacc   8220
tcgcgctcga aggcccccgg gagttcctcc acttcctctt cttcctcctc cactaacatc   8280
tcttctactt cctcctcagg cggcagtggt ggcggggag ggggcctgcg tcgccggcgg    8340
cgcacgggca gacggtcgat gaagcgctcg atggtctgcc cggccggcg tcgcatggtc    8400
tcggtgacgg cgcgcccgtc ctcgcggggc cgcagcgtga agacgccgcc gcgcatctcc   8460
aggtggccgg gggggtcccc gttgggcagg gagagggcgc tgacgatgca tcttatcaat   8520
tgccccgtag ggactccgcg caaggacctg agcgtcgga gatccacggg atctgaaaac    8580
cgctgaacga aggcttcgag ccagtcgcag tcgcaaggta ggctgagcac ggtttcttct   8640
ggcgggtcat gttggttggg agcggggcgg gcgatgctgc tggtgatgaa gttgaaatag   8700
gcggttctga gacggcggat ggtggcgagg agcaccaggt ctttgggccc ggcttgctgg   8760
atgcgcagac ggtcggccat gccccaggcg tggtcctgac acctggccag gtccttgtag   8820
tagtcctgca tgagccgctc cacgggcacc tcctcctcgc ccgcgcggcc gtgcatgcgc   8880
gtgagcccga agcgcgcgtc gggctggacg agcgccaggt cggcgacggc gcgctcggcg   8940
aggatggctt gctggatctg ggtgagggtg gtctggaagt catcaaagtc gacgaagcgg   9000
tggtaggctc cggtgttgat ggtgtaggag cagttggcca tgacgaccca gttgacggtc   9060
tggtggcccg gacgcacgag ctcgtggtac ttgaggcgcg agtaggcgcg cgtgtcgaag   9120
atgtagtcgt tgcaggtgcc caccaggtac tggtagccga tggcggcgag cggcggcggc   9180
tggcggtaga gcggccatcg ctcggtggcg ggggcgccgg gcggagggtc ctcgagcatg   9240
gtgcggtggt agccgtagat gtacctggac atccaggtga tgccggcggc ggtggtggag   9300
gcgcgcggga actcgcggac gcggttccag atgttgcgca gcggcaggaa gtagttcatg   9360
gtgggcacgg tctgcccgt gaggcggcg cagtcgtgga tgctctatac gggcaaaaac    9420
gaaagcggtc agcggctcga ctccgtggcc tggaggctaa gcgaacgggt tgggctgcgc   9480
gtgtaccccg gttcgaatct cgaatcaggc tggagccgca gctaacgtgg tattggcact   9540
cccgtctcga cccaagcctg caccaaccct ccaggatacg gaggcgggtc gttttgcaac   9600
ttttttttgg aggccggatg agactagtaa gcgcggaaag cggccgaccg cgatggctcg   9660
ctgccgtagt ctggagaaga atcgccaggg ttgcgttgcg gtgtgccccg gttcgaggcc   9720
ggccggattc cgcggctaac gagggcgtgg ctgcccgtc gtttccaaga ccccatagcc    9780
agccgacttc tccagttacg gagcgagccc ctctttgtt ttgtttgttt ttgccagatg    9840
catcccgtac tgcggcagat gcgccccac caccctccac cgcaacaaca gccccctcca   9900
cagccggcgc ttctgccccc gcccagcag caacttccag ccacgaccgc cgcggccgc    9960
gtgagcgggc ctgacagag ttatgatcac cagctggcct tggaagaggg cgaggggctg    10020
gcgcgcctgg gggcgtcgtc gccggagcgg cacccgcgcg tgcagatgaa agggacgct    10080
cgcgaggcct acgtgccaa gcagaacctg ttcagagaca ggagcggcga ggagcccgag   10140
gagatgcgcg cggccggtt ccacgcgggg cgggagctgc ggcgcggcct ggaccgaaag    10200
agggtgctga gggacgagga tttcgaggcg gacgagctga cggggatcag ccccgcgcgc   10260
gcgcacgtgg ccgcggccaa cctggtcacg gcgtacgagc agaccgtgaa ggaggagagc   10320
aacttccaaa aatccttcaa caaccacgtg cgcaccctga tcgcgcgcga ggaggtgacc   10380
ctgggcctga tgcacctgtg gacctgctg gaggccatcg tgcagaaccc caccagcaag   10440
ccgctgacgg cgcagctgtt cctggtggtg cagcatagtc gggacaacga agcgttcagg   10500
gaggcgctgc tgaatatcac cgagcccgag ggccgctggc cctgacctt ggtgaacatt   10560
ctgcagagca tcgtggtgca ggagcgcggg ctgccgctgt ccgagaagct ggcggccatc   10620
aacttctcgg tgctgagttt gggcaagtac acgctagga agatctacaa gaccccgtac   10680
gtgcccatag acaaggaggt gaagatcgac gggttttaca tgcgcatgac cctgaaagtg   10740
ctgaccctga gcgacgatct gggggtgtac cgcaacagac ggatgcaccg tgcggtgagc   10800
gccagcaggc ggcgcgagct gagcgaccag gagcgatgac atagtctgca gcgggccctg   10860
accggggccg ggaccgaggg ggagagctac tttgacatgg gcgcggacct gcactggcag   10920
cccagccgcc gggccttgga ggcggcggca ggaccctacg tagaagaggt ggacgatgag   10980
gtggacgagg aggggcagta cctggaagac tgatgacgca accgtatttt tgctagatgc   11040
aacaacaaca gccaccttcctt gatcccgcga tgcgggcggc gctgcagagc cagccgtccg   11100
gcattaactc ctcggacgat tgaccccagg ccatgcaacg catcatgcg ctgacgaccc    11160
gcaacccccga agctttaga cagcagcccc aggccaaccg gctctcggcc atcctggagg   11220
ccgtggtgcc ctcgcgctcc aaccccacgc acgaagaggt cctggccatc gtgaacgcgc   11280
tggtggagaa caaggccatc cgcggcgacg aggccggcct ggtgtacaac gcgctgctgg   11340
```

```
agcgcgtggc cgctacaac agcaccaacg tgcagaccaa cctgaccgc atggtgaccg   11400
acgtgcgcga ggccgtggcc cagcgcgagc ggttccaccg cgagtccaac ctgggatcca   11460
tggtggcgct gaacgccttc ctcagcaccc agcccgccaa cgtgcccgg ggccaggagg   11520
actacaccaa cttcatcagc gccctgcgcc tgatggtgac cgaggtgccc cagagcgagg   11580
tgtaccagtc cgggccggac tacttcttcc agaccagtca ccagggcttg cagaccgtga   11640
acctgagcca ggcttttcaag aacttgcagg gcctgtgggg cgtgcaggcc ccggtcgggg   11700
accgcgcgac ggtgtcgagc ctgctgacgc cgaactcgcg cctgctgctg ctgctggtgg   11760
ccccccttcac ggacagcggc agcatcaacc gcaactcgta cctgggctac ctgattaacc   11820
tgtaccgcga ggccatcggc caggcgcacg tggacgagca gacctaccag gagatcaccc   11880
acgtgaccg cgccctgggc caggacgacc cgggcaacct ggaagccacc ctgaacttt   11940
tgctgaccaa ccggtcgcag aagatcccgc cccagtacgc gctcagcacc gaggaggagc   12000
gcatcctgcg ttacgtgcag cagagcgtgg gcctgttcct gatgcaggag ggggccaccc   12060
ccagcgccgc gctcgacatg accgcgcgca acatggagcc cagcatgtac gccagcaacc   12120
gcccgttcat caataaactg atggactact tgcatcgggc ggccgccatg aactctgact   12180
atttcaccaa cgccatcctg aatcccact ggctcccgcc gccggggttc tacacgggcg   12240
agtacgacat gcccgacccc aatgacgggt tcctgtggga cgatgtggac agcagcgtgt   12300
tctccccccg accgggtgct aacgagcgcc ccttgtggaa gaaggaaggc agcgaccgac   12360
gcccgtcctc ggcgctgtcc ggccgcgagg gtgctgccgc ggcggtgccc gaggccgcca   12420
gtccttttccc gagcttgccc ttctcgctga acagtatccg cagcagcgag ctgggcagga   12480
tcacgcgccc gcgcttgctg ggcgaagagg agtacttgaa tgactcgctg ttgagacccg   12540
agcgggagaa gaacttcccc aataacggga tagaaagcct ggtggacaag atgagccgct   12600
ggaagacgta tgcgcaggag cacagggacg atccccggc gtcgcagggg gccacgagca   12660
ggggcagcgc cgcccgtaaa cgccggtggc acgacaggga gcgggacag atgtgggacg   12720
atgaggactc cgccgacgac agcagcgtgt tggacttggg tgggagtggt aacccgttcg   12780
ctcacctgcg ccccccgtatc gggcgcatga tgtaagagaa accgaaaata aatgatactc   12840
accaaggcca tggcgaccag cgtgcgttcg tttcttctct gttgttgttg tatctagtat   12900
gatgaggcgt gcgtaccgg agggtcctcc tccctcgtac gagagcgtga tgcagcaggc   12960
gatgcgcgg gcgcgatgc agcccccgct ggaggctcct tacgtgcccc cgcggtacct   13020
ggcgcctacg gaggggcgga acagcattcg ttactcggag ctggcaccct tgtacgatac   13080
cacccggttg tacctggtgg acaacaagtc ggccgacatc gcctcgctga actaccagaa   13140
cgaccacagc aacttcctga ccaccgtggt gcagaacaat gacttcaccc ccacggaggc   13200
cagcaccccag accatcaact tgacgagcg ctcgcggtgg ggcggccagc tgaaaaccat   13260
catgcacacc aacatgccca acgtgaacga gttcatgtac agcaacaagt tcaaggcgcg   13320
ggtgatggtc tcccgcaaga cccccaatgg ggtgacagtg acagaggatt atgatggtag   13380
tcaggatgag ctgaagtatg aatgggtgga atttgacgtg cccgaaggca acttctcggt   13440
gaccatgacc atcgacctga tgaacaacgc catcatcgac aattacttgg cggtggggcg   13500
gcagaacggg gtgctggaga gcgacatcgg cgtgaagttc gacactagga acttcaggct   13560
gggctgggac cccgtgaccg agctggtcat gcccggggtg tacaccaacg aggctttcca   13620
tccgatattt gtcttgctgc ccggctgcgg ggtggacttc accgagagcc gcctcagcaa   13680
cctgctggcc attcgcaaga ggcagccctt ccaggaaggc ttccagatca tgtacgagga   13740
tctgaggggg ggcaacatcc ccgcgctcct ggatgtcgac gcctatgaga aaagcaagga   13800
ggatgcagca gctgaagcaa ctgcagccgt agctaccgcc tctaccgagg tcaggggcga   13860
taatttttgca agcgccgcag cagtggcagc ggccgaggcg gctgaaaccg aaagtaagat   13920
agtcattcag ccggtggaga aggatagcaa gaacaggagc tacaacgtac taccggacaa   13980
gataaacacc gcctaccgca gctggtacct agcctacaac tatggcgacc ccagaaaggg   14040
cgtgcgctcc tggacgctgc tcaccacctc ggacgtcacc tgcggcgtgg agcaagtcta   14100
ctggtcgctg cccgacatga tgcaagaccc ggtcaccttc cgctccacgc gtcaagttag   14160
caactacccg gtggtgggcg ccgagctcct gccccgtctac tccaagagct tcttcaacga   14220
gcaggccgtc tactcgcagc agctgcgcgc cttcacctcg cttacgcacg tcttcaaccg   14280
cttccccgag aaccagatcc tcgtccgccc gccccgcgccc accattacca ccgtcagtga   14340
aaacgttcct gctctcacag atcacggac cctgccgctg cgcagcagta tccggggagt   14400
ccagcgcgtg accgttactg acgccagacg ccgcacctgc ccctacgtct acaaggccct   14460
gggcatagtc gcgccgcgcg tcctctcgag ccgcaccttc taaatgtcca ttctcatctc   14520
gcccagtaat aacaccggtt ggggcctgcg cgcgcccagc aagatgtacg gaggcgctcg   14580
ccaacgctcc acgcaacacc ccgtcgcgct gcgcgggcaa ttccgcgctc cctgggcgg   14640
cctcaagggc cgcgtgcggt cgcgcaccac cgtcgacgac gtgatcgacc aggtggttgg   14700
cgacgcgcgc aactacaccc ccgcgccgc gcccgtctcc accgtggacg ccgtcatcga   14760
cagcgtggtg gcggacgcgc gccggtacgc ccgcgccaag agccggcggc ggcgcatcgc   14820
ccggcggcac cggagccacc ccgcccatgcg cgcggcgcga gccttgctgc gcagggccag   14880
gcgcacggga cgcagggcca tgctccaggc ggccagcgc gcggcttcag gcgccagcgc   14940
cggcaggacc cggagacgcg cggccacggc ggcggcagcg gccatcgcca gcatgtcccg   15000
cccgcggcga gggaacgtgt actgggtgcg cgacgccgcc accggtgtgc gcgtgcccgt   15060
gcgcacccgc ccccctcgca cttgaagatg ttcacttcgc gatgttgatg tgtcccagcg   15120
gcgaggagga tgtccaagcg caaattcaag gaagagatgc tccaggtcat cgcgcctgag   15180
atctacggcc ctgcgtggt gaaggaggaa agaaagcccc gcaaaatcaa gcgggtcaaa   15240
aaggacaaaa aggaagaaga aagtgatgtg gacggattgg tggagtttgt gcgcgagttc   15300
gccccccggc ggcgcgtgca gtggcgcggg cggaaggtgc aaccggtgct gagacccggc   15360
accacccgtgg tcttcacgcc cggcgagcgc tccggcaccg cttccaagcg ctcctacgac   15420
gaggtgtacg gggatgatga tatttctgag caggcgccgg aggcgcctgc cgagtttgct   15480
tacggcaagc gcagccgttc cgcaccgaag aagaggcgg tgtccatccc gctggaccac   15540
ggcaacccca cgccgagcct caagcccgtg accttgcagc aggtgctgcc gaccgcggcg   15600
ccgcgccggg ggttcaagcg cgagggcgag atctgtacc ccaccatgca gctgatggtg   15660
cccaagcgcc agaagctgga agacgtgctg gagaccatga aggtggaccc ggacgtgcag   15720
cccggaggtca aggtgcggcc catcaagcag gtggcccgcg aggcaagcgg cgacatcaaga   15780
gacatcaaga ttcccacgga gcccatgaaa acgcagaccc agcccatgat caagcccagc   15840
accagcacca tggaggtgca gacggatccc tggatgccat cggctcctag tcgaagaccc   15900
cggcgcaagt acgcgcgggc cagcctgctg atgcccaact acgcgctgca tccttccatc   15960
atccccacgc cgggctaccg cggcacgcgc ttctaccgcg gtcataccag cagccgccgc   16020
cgcaagacca ccactcgccg ccgccgtcgc cgcaccgccg ctgcaaccac ccctgccgcc   16080
```

-continued

```
ctggtgcgga gagtgtaccg ccgcggccgc gcacctctga ccctgccgcg cgcgcgctac   16140
caccccgagca tcgccattta aactttcgcc agctttgcag atcaatggcc ctcacatgcc   16200
gccttcgcgt tcccattacg ggctaccgag gaagaaaacc gcgccgtaga aggctggcgg   16260
ggaacgggat gcgtcgccac caccaccggc ggcggcgcgc catcagcaag cggttggggg   16320
gaggcttcct gcccgccgctg atccccatca tcgccgcccgg gatcggggcg atccccggca  16380
ttgcttccgt ggcggtgcag gcctctcagc gccactgaga cacacttgga aacatcttgt   16440
aataaaccca tggactctga cgctcctggt cctgtgatgt gttttcgtag acagatggaa   16500
gacatcaatt tttcgtccct ggctccgcga cacggcacgc ggccgttcat gggcacctgg   16560
agcgacatcg gcaccagcca actgaacggg ggcgccttca attggagcag tctctggagc   16620
gggcttaaga atttcgggtc cacgcttaaa acctatggca gcaaggcgtg gaacagcacc   16680
acagggcagg cgctgaggga taagctgaaa gagcagaact tccagcagaa ggtggtcgat   16740
gggctcgcct cgggcatcaa cggggtggtg gacctggcca accaggccgt gcagcggcag   16800
atcaacagcc gcctggaccc ggtgccgccc gccggctccg tggagatgcc gcaggtggag   16860
gaggagctgc ctcccctgga caagcggggc gagaagcgac cccgccccga tgccggaggag  16920
acgctgctga cgcacacgga cgagccgccc ccgtacgagg aggcggtgaa actgggtctg   16980
cccaccacgc ggcccatcgc gcccctggcc accggggtgc tgaaacccga aaagcccgcg   17040
accctggact tgcctcctcc ccagccttcc cgccctcta cagtggctaa gcccctgccg     17100
ccggtgggcg tggcccgcgc gcgacccggg ggcaccgccc gccctcatgc gaactggcag   17160
agcactctga acagcatcgt gggtctggga gtgcagagtg tgaagcgccg ccgctgctat   17220
taaacctacc gtagcgctta acttgcttgt ctgtgtgtgt atgtattatg tcgccgccgc   17280
cgctgtccac cagaaggagg agtgaagagg cgcgtcgccg agttgcaaga tggccacccc   17340
atcgatgctg cccccagtggg cgtacatgca catcgccgga caggacgctt cggagtacct   17400
gagtccgggt ctggtgcagt ttgcccgcgc cacagacacc tacttcagtc tgggggaacaa   17460
gtttaggaac cccacggtgg cgcccacgca cgatgtgacc accgaccgca gccagcggct   17520
gacgctcgcg ttcgtgcccg tggaccgcga ggacaacacc tactcgtaca aagtgcgcta   17580
cacgctggcc gtgggcgaca accgcgtgct ggacatgcc agcacctact ttgacatccg   17640
cggcgtgctg gatcggggcc ctagcttcaa accctactcc ggcaccgcct acaacagtct   17700
ggcccccaag ggagcaccca acacttgtca gtggacatat aaagccgatg gtgaaactgc   17760
cacagaaaaa acctatacat atggaaatgc acccgtgcag ggcattaaca tcacaaaaga   17820
tggtattcaa cttggaactg acaccgatga tcagccaata tacgcagata aaacctatca   17880
gcctgaacct caagtgggtg atgctgaatg gcatgacatc actggtactg atgaaaagta   17940
tggaggcaga gctcttaagc ctgataccaa aatgaagcct tgttatggtt cttttgccaa   18000
gcctactaat aaagaaggag gtcaggcaaa tgtgaaaaca ggaacaggca ctactaaaga   18060
atatgacata gacatggctt tctttgacaa cagaagtgcg gctgctgctg gcctagctc   18120
agaaattgtt tttgtatactg aaaatgtgga tttggaaact ccagataccc atattgtata   18180
caaagcaggc acagatgaca gcagctcttc tattaatttg ggtcagcaag ccatgcccaa   18240
cagacctaac tacattggtt tcagagacaa ctttatcggg ctcatgtact acaacagcac   18300
tggcaatatg ggggtgctgg ccggtcaggc ttctcagctg aatgctgtgg ttgacttgca   18360
agacagaaac accgagctgt cctaccagct cttgcttgac tctctgggtg acagaaccccg   18420
gtatttcagt atgtgtaatc aggcggtgga cagctgatgat cctgatgtgc gcattattga   18480
aaatcatggt gtgaaggatg aacttccaa ctattgtttc cctctggatg ctgttggcag    18540
aacagatact tatcagggaa ttaaggctaa tggaactgat caaaccacat ggaccaaaga   18600
tgacagtgtc aatgatgcta atgagatagg caagggtaat ccattcgcca tggaaatcaa   18660
catccaagcc aacctgtgga ggaacttcct ctacgccaac gtggccctgt acctgcccga   18720
ctcttacaag tacacgccgg ccaatgttac cctgcccacc aacaccaaca cctacgatta   18780
catgaacggc cgggtggtgg cgccctcgct ggtggactcc tacatcaaca tcggggcgcg   18840
ctggtcgctg gatcccatgg acaacgtgaa ccccttcaac caccaccgca atgcgggggct  18900
gcgctaccgc tccatgctcc tgggcaacgg cgcgctacgtg cccttccaca tccaggtgcc   18960
ccagaaattt tcgccatca agagcctcct gctcctgccc gggtcctaca cctacgagtg    19020
gaacttccgc aaggacgtca acatgatcct gcagagctcc ctcggcaacg acctgcgcac   19080
ggacggggcc tccatctcct tcaccagcat caacctctac gccaccttct cccccatgga   19140
gcacaacacg gcctccacgc tcgaggccat gctgcgcaac gacaccaacg accagtcctt   19200
caacgactac ctctcggcgg ccaacatgct ctacccccatc ccggccaacg ccaccaacgt   19260
gcccatctcc atcccctcgc gcaactgggc cgccttccgc ggctggtcct tcacgcgtct   19320
caagaccaag gagacgcccc cgctggggctc cgggttcgac ccctacttcg tctactcggg   19380
ctccatcccc tacctcgacg gcaccttcta cctcaaccac accttcaaga ggtctccatc    19440
caccttcgac tcctccgtca gctggcccgg caacgaccgg ctcctgacgc ccaacgagtt   19500
cgaaatcaag cgcaccgtcg acggcgaggg ctacaacgtg gcccagtgca acatgaccaa   19560
ggactggttc ctggtccaga tgctggccca ctacaacatc ggctaccggg gcttctacgt   19620
gccccgagggc tacaaggacc gcatgtactc cttcttccgc aacttccagc ccatgagccg   19680
ccaggtggtg gacgaggtca actacaagga ctaccaggcc gtcaccctgg cctaccagca   19740
caacaactcg ggcttcgtcg gctacctcgc gccaccatg cgccagggcc agccctaccc     19800
cgccaactac ccctaccccgc tcatcggcaa gagcgccgtc accagcgtca cccagaaaaa   19860
gttcctctgc gacagggtca tgtggcgcat cccttcctcc agcaacttca tgtccatgca   19920
cgcgctcacc gacctcggcc agaacatgct ctatgccaac tccgcccacg cgctagacat   19980
gaatttcgaa gtcgaccca tggatgagtc caccttctc tatgttgtct tcgaagtctt     20040
cgacgtcgtc cgagtgcacc agccccaccg cggcgtcatc gaggccgtct acctgcgcac   20100
cccccttctcg gccggtaacg ccaccaccta agctcttgct tcttgcaagc catggccgcg   20160
ggctccggcg agcaggagct cagggccatc atccgcacc tgggctgcgg gccctacttc   20220
ctggcaccct tcgataagcg cttcccggga ttcatggccc cgcacaagct ggcctcgcgcc   20280
atcgtcaaca cggccggccg cgagaccggg ggcgagcact ggctggcctt cgcctggaac   20340
ccgcgctcga acacctgcta cctcttcgac cccttcgggt tctcggacga cgcgcctcaag   20400
cagatctacc agttcgagta cgagggcctg ctgcgccgca gcgccctggc caccgaggac   20460
cgctgcgtca ccctggaaaa gtccaccag accgtgcagg gccctgctgc ggccgctgc      20520
gggctcttct gctgcatgtt cctgcacgcc ttcgtgcact ggcccgaccg cccccatggac   20580
aagaacccca ccatgaactt gctgacgggg tgtgccaacg gcatgctcca gtcgcccag    20640
gtggaaccca ccctgcgccg caaccaggag gcgctctacc gcttcctcaa ctcccactcc   20700
gcctactttc gctcccaccg cgcgcgcatc gagaaggcca ccgccttcga ccgcatgaat   20760
caagacatgt aaaaccgtgtg tgtatgttaa atgtctttaa taaacagcac tttcatgtta   20820
```

```
cacatgcatc tgagatgatt tatttagaaa tcgaaagggt tctgccgggt ctcggcatgg   20880
cccgcgggca gggacacgtt gcggaactgg tacttggcca gccacttgaa ctcggggatc   20940
agcagtttgg gcagcggggt gtcggggaag gagtcggtcc acagcttccg cgtcagttgc   21000
agggcgccca gcaggtcggg cgcggagatc ttgaaatcgc agttgggacc cgcgttctgc   21060
gcgcgggagt tgcggtacac ggggttgcag cactggaaca ccatcaggcc cgggtgcttc   21120
acgctcgcca gcaccgtcgc gtcggtgatg ctctccacgt cgaggtcctc ggcgttggcc   21180
atcccgaagg gggtcatctt gcaggtctgc cttccatgg tgggcacgca cccgggcttg   21240
tggttgcaat cgcagtgcag ggggatcagc atcatctggg cctggtcggc gttcatcccc   21300
gggtacatgg ccttcatgaa agcctccaat tgcctgaacg cctgctgggc cttggctcgc   21360
tcggtgaaga agaccccgca ggacttgcta gagaactggt tggtggcgca cccggcgtcg   21420
tgcacgcagc agcgcgcgtc gttgttggcc agctgcacca cgctgcgccc ccagcggttc   21480
tgggtgatct tggcccggtc gggttctcc ttcagcgcgc gctgcccgtt ctcgctcgcc   21540
acatccatct cgatcatgtg ctccttctgg atcatggtag tcccgtgcag gcaccgcagc   21600
ttgccctcgg cctcggtgca cccgtgcagc cacagccgcg accggtgca ctcccagttc   21660
ttgtgggcga tctgggaatg cgcgtgcacg aagcccgtca ggaagcggcc catcatggtg   21720
gtcagggtct tgttgctagt gaaggtcagc ggaatgccgc ggtgctcctc gttgatgtac   21780
aggtggcaga tgcggcggta caccctcgcc tgctcggca tcagctggaa gttggctttc   21840
aggtcggtct ccacgcggta gcggtccatc agcatagtca tgatttccat acccttctcc   21900
caggccgaga cgatgggcag gctcataggg ttcttcacca tcatcttagc gctagcagcc   21960
gcggccaggg ggtcgctctc gtccagggtc tcaaagctcc gcttgccgtc cttctcggtg   22020
atccgcaccg ggggtagct gaagcccacg gccgccagct cctcctcggc ctgtctttcg   22080
tcctcgctgt cctggctgac gtcctgcagg accacatgct tggtcttgcg gggttcttc   22140
ttgggcggca gcggcggcgg agatgttgga gatggcgagg gggagcgcga gttctcgctc   22200
accactacta tctcttcctc ttcttggtcc gaggccacgc ggcggtaggt atgtctcttc   22260
gggggcagag gcggaggcga cgggctctcg ccgccgcgac ttggcggatg gctggcagag   22320
cccctttccgc gttcgggggt gcgctcccgg cggcgctctg actgacttcc tccgcggccg   22380
gccattgtgt tctcctaggg aggaacaaca agcatggaga ctcagccatc gccaacctcg   22440
ccatctgccc ccaccgccga cgagaagcag cagcagcaga atgaaagctt aaccgccccg   22500
ccgcccagcc ccgccacctc cgacgcggcc gtcccagaca tgcaagagat ggaggaatcc   22560
atcgagattg acctgggcta tgtgagcgcc gcggagcacg aggaggagct ggcagtgcgc   22620
ttttcacaag aagagataca ccaagaacag ccagagcagg aagcagagaa tgagcagagt   22680
caggctgggc tcgagcatga cggcgactac ctccacctga gcgggggggga ggacgcgctc   22740
atcaagcatc tggcccggca ggccaccatc gtcaaggatg cgctgctcga ccgcaccgag   22800
gtgccctca gcgtggagga gctcagccgc gcctacgagt tgaacctctt ctcgccgcgc   22860
gtgccccca agcgccagcc caatgcacc tgcgagccca accgcgcct caacttctac   22920
ccggtcttcg cggtgcccga ggccctggcc acctaccaca tctttttcaa gaaccaaaag   22980
atccccgtct cctgccgcgc caaccgcacc cgcgccgacg cccttttcaa cctgggtccc   23040
ggcgcccgcc tacctgatat cgcctccttg gaagaggttc ccaagatctt cgagggtctg   23100
ggcagcgacg agactcgggc cgcgaacgct ctgcaaggag aaggaggaga gcatgagcac   23160
cacagcgccc tggtcgagtt ggaaggcgac aacgcgcggc tggcggtgct caaacgcacg   23220
gtcgagctga cccatttcgc ctaccccgct ctgaacctgc cccccaaagt catgagcgcg   23280
gtcatgacc aggtgctcat caagcgcgcg tcgcccatct ccgaggacga gggcatgcaa   23340
gactccgagg agggcaagcc cgtggtcagc gacgagcagc tggccgggtg gctgggtcct   23400
aatgctagtc cccagagttt ggaagagcgg cgcaaactca tgatggccgt ggtcctggtg   23460
accgtgagc tggagtgcct gcgccgcttc ttcgccgacg cggagaccct gcgcaaggtc   23520
gaggagaacc tgcactacct cttcaggcac gggttcgtgc gccaggcctg caagatctcc   23580
aactgtgagc tgaccaacct ggtctcctac atgggacttt gcacgagaa ccgcctgggg   23640
cagaacgtgc tgcacaccac cctgcgcggg gaggcccggc gcgactacat ccgcgactgc   23700
gtctacctct acctctgcca cacctggcag acgggcatgg gcgtgtgca gcagtgtctg   23760
gaggagcaga acctgaaaga gctctgcaag ctcctgcaga agaacctcaa gggtctgtgg   23820
accggttcg acgagcgcac caccgcctcg gacctgcattt ccccgagcgc   23880
ctcaggctga cgctgcgcaa cggcctgccc gactttatga gccaaagcat gttgcaaaac   23940
tttcgctctt tcatcctcga acgctccgga atcctgcccg ccacctgctc cgcgctgccc   24000
tcggacttcg tgccgctgac cttccgcgag tgccccgc cgctgtggag ccactgctac   24060
ctgctgcgcc tggccaacta cctggcctac cactcggacg tgatcgagga cgtcagcggc   24120
gagggcctgc tcgagtgcca ctgccgctgc aacctctgca cgccgcaccg ctccctggcc   24180
tgcaacccc agctgctgag cgagacccag atcatcggca ccttcgagtt gcaagggccc   24240
agcgaaggcc agggttcagc cgccaagggg ggtctgaaac tcaccccggg gctgtggacc   24300
tcggcctact tgcgcaagtt cgtgccgag gactaccatc ccttcgagat caggttctac   24360
gaggaccaat cccatccgcc caaggccgag ctgtcggcct gcgtcatcac ccagggggcg   24420
atcctggccc aattgcaagc catccagaaa tcccgcaag aattcttgct gaaaagggc   24480
cgcgggtct acctcgaccc ccagaccggt gaggagctca accccggctt cccccaggat   24540
gccccgagga acaagaagc tgaaagtgga gctgccgccc gtggaggatt tggaggaaga   24600
ctgggaaac agcagtcagg cagaggagga ggagtggaa gaagactcaa acagcactca   24660
ggcagaggag gacagcctgc aagacagtct ggaggaagac gaggaggagg cagaggagga   24720
ggtgaagaa gcagccgccg ccagaccgtc gtcctcggcg gggagaaag caagcagcac   24780
ggataccatc tccgctccgg gtcggggtcc cgctcgacca cacagtagat gggacggagc   24840
cggacgattc ccgaacccca ccacccagac cggtaagaag gagcggcagg gatacaagtc   24900
ctggcgggg cacaaaaacg ccatcgtctc ctgcttgcg gcctgcgggg gcaacatctc   24960
cttcacccgg cgctacctgc tcttccaccg cgggtgaac tttccccgca acatcttgca   25020
ttactaccgt cacctccaca gccctacta cttccaagaa gaggcagcag cagcagaaaa   25080
agaccagcag aaaaccagca gctagaaaat ccacagcggc ggcagcaggt ggactgagga   25140
tcgcggcgaa cgagccggcg caaacccggg agctgaggaa ccggatcttt cccacccct   25200
atccttt ccagcagagt cgggggcagg agcaggaact gaaagtcaag aaccgtctctc   25260
tgcgctcgct cacccgcagt tgtctgtatc acaagagcga agaccaactt cagcgcactc   25320
tcgaggacgc cgaggctctc ttcaacaagt actgcgcgct cactcttaaa gagtagcccg   25380
cgccccgcca gtcgcagaaa aaggcgggaa ttacgtcacc tgtgcccttc gcctgagccg   25440
cctcacccca tcatcatgag caagagatt cccacgcctt acatgtggag ctaccagccc   25500
cagatgggcc tggccgccgg tgccgcccag gactactcca cccgcatgaa ttggctcagc   25560
```

```
gccgggcccg cgatgatctc acgggtgaat gacatccgcg cccaccgaaa ccagatactc  25620
ctagaacagt cagcgctcac cgccacgccc cgcaatcacc tcaatccgcg taattgggcc  25680
gccgccctgg tgtaccagga aattcccag cccacgaccg tactacttcc gcgagacgcc   25740
caggccgaag tccagctgac taactcaggt gtccagctgg cgggcggcgc caccctgtgt  25800
cgtcaccgcc ccgctcaggg tataaagcgg ctggtgatcg ggggcagagg cacacagctc  25860
aacgacgagg tggtgagctc ttcgctgggc ctgcgacctg acggagtctt ccaactcgcc  25920
ggatcgggga gatcttcctt cacgcctcgt caggccgtcc tgactttgga gagttcgtcc  25980
tcgcagcccc gctcggtgg catcggcact ctccagttcg tggaggagtt cactccctcg   26040
gtctacttca accccttctc cggctccccc ggccactacc cggacgagtt catcccgaac  26100
ttcgacgcca tcagcgagtc ggtggacggc tacgattgag tttaaactca cccccttatc  26160
cagtgaaata aagatcatat tgatgatgat tttacagaaa taaaaaataa tcatttgatt  26220
tgaaataaag atacaatcat attgatgatt tgagtttaac aaaaaaataa agaatcactt  26280
acttgaaatc tgataccagg tctctgtcca tgttttctgc caacaccact tcactcccct  26340
cttcccagct ctggtactgc aggccccggc gggctgcaaa cttcctccac acgctgaagg  26400
ggatgtcaaa ttcctcctgt ccctcaatct tcattttatc ttctatcaga tgtccaaaaa  26460
gcgcgtccgg gtggatgatg acttcgaccc cgtctacccc tacgatgcag acaacgcacc  26520
gaccgtgccc ttcatcaacc ccccttcgt ctcttcagat ggattccaag agaagcccct   26580
gggggtgttg tccctgcgac tggccgaccc cgtcaccacc aagaacgggg aaatcacccct 26640
caagctggga gaggggtgg acctcgattc ctcgggaaaa ctcatctcca cacggccac    26700
caaggccgcc gcccctctca gttttttccaa caacaccatt tccccttaaca tggatcaccc 26760
cttttacact aaagatggaa aattatcctt acaagtttct ccaccattaa atatactgag   26820
aacaagcatt ctaaacacac tagctttagg ttttggatca ggtttaggac tccgtggctc  26880
tgccttggca gtacagttag tctctccact tacatttgat actgatgaa acataaagct    26940
taccttagac agaggtttgc atgttacaac aggagatgca attgaaagca cataagctg    27000
ggctaaaggt ttaaaatttg aagatggagc catagcaacc aacattggaa atgggttaga  27060
gtttggaagc agtagtacag aaacaggtgt tgatgatgct tacccaatcc aagttaaact  27120
tggatctggc cttagctttg acagtacagg agccataatg gctggtaaca aagaagacga  27180
taaactcact ttgtggacaa cacctgatcc atcaccaaac tgtcaaatac tcgcagaaaa  27240
tgatgcaaaa ctaacacttt gcttgactaa atgtggtagt caaatactgg ccactgtgtc  27300
agtcttagtt gtaggaagtg gaaacctaaa ccccattact ggcaccgtaa gcagtgctca  27360
ggtgttttcta cgttttgatg caaacgtgt tcttttaaca gaacattcta cactaaaaaa   27420
atactgggggg tataggcagg gagatagcat agatggcact ccatatacca atgctgtagg  27480
attcatgccc aatttaaaag cttatccaaa gtcacaaagt tctactacta aaaataatat  27540
agtagggcaa gtatacatga atggagatgt ttcaaaacct atgcttctca ctataaccct  27600
caatggtact gatgacagca acagtacata ttcaatgtca ttttcataca cctggactaa  27660
tggaagctat gttggagcaa catttgggc taactcttat accttctcat acatcgccca   27720
agaatgaaca ctgtatccca ccctgcatgc caacccttcc caccccactc tgtggaacaa  27780
actctgaaac acaaaataaa ataaagttca agtgttttat tgattcaaca gtttcacaga  27840
accctagtat tcaacctgcc acctccctcc caacacacag agtacacagt cctttctccc   27900
cggctggcct taaaaagcat catatcatgg gtaacagaca tattcttagg tgttatattc   27960
cacacggttt cctgtcgagc caaacgctca tcagtgatat taataaactc cccgggcagc  28020
tcacttaagt tcatgtcgct gtccagctgc tgagccacag gctgctgtcc aacttgcggt   28080
tgcttaacgg gcggcgaagg agaagtccac gcctacatgg gggtagagtc ataatcgttgc 28140
atcaggatag ggcggtggtg ctgcagcagc gcgcgaataa actgctgccg ccgccgctcc  28200
gtcctgcagg aatacaacat ggcagtggtc tcctcagcga tgattcgcac cgcccgcagc  28260
ataaggcgcc ttgtcctccg ggcacagcag cgcaccctga tctcacttaa atcagcacag  28320
taactgcagc acagcaccac aatattgttc aaaatcccac agtgcaaggc gctgtatcca  28380
aagctcatgg cggggaccac agaacccacg tggccatcat accacaagcg caggtagatt  28440
aagtggcgac ccctcataaa cacgctggac ataaacatta cctcttttgg catgttgtaa  28500
ttcaccacct cccggtacca tataaacctc tgattaaaca tggcgccatc caccaccatc  28560
ctaaaccagc tggccaaaac ctgcccgccg gctatacact gcagggaacc gggactggaa  28620
caatgacagt ggagagccca ggactcgtaa ccatggatca tcatgctcgt catgatatca  28680
atgttggcac aacacaggca cacgtgcata cacttcctca ggattacaag ctcctcccgc  28740
gttagaacca tatcccaggg aacaaaccat tcctgaatca gcgtaaatcc cacactgcag  28800
ggaagaccct gcacgtaact cacgttgtgc atttgtcaaca tgttacattc gggcagcagc  28860
ggatgatcct ccagtatggt agcgcgggtt tctgtctcaa aaggaggtag acgatccta   28920
ctgtacggag tgcgccgaga caaccgagat cgtgttggtc gtagtgtcat gccaaatgga  28980
acgccggacg tagtcatatt tcctgaagca aaaccaggtg cgggcgtgac aaacagatct  29040
gcgtctccgg tctcgccgct tagatcgctc tgtgtagtag ttgtagtata tccactctct  29100
caaagcatcc aggcgcgccc tggcttcggg ttctatgtaa actccttcat gcgccgctgc  29160
cctgataaca tccaccaccg cagaataagc cacacccagc caacctacac attcgttctg  29220
cgagtcacac acgggaggag cgggaagagc tggaagaacc atgattaact ttattccaaa  29280
cggtctcgga gcacttcaaa atgcaggtcc cggaggtggc acctctcgcc cccactgtgt  29340
tggtggaaaa taacagccag gtcaaaggtg acacggttct ccgagtgttc cacggtggtc  29400
tccagcaaag cctccacgcg cacatccaga aacaagagga cagcgaaagc gggagcgttt  29460
tctaattcct caatcatcat attacactcc tgcaccatcc ccagataatt tcattttttc   29520
cagccttgaa tgattcgtat tagttcctga ggtaaatcca agccagccat gataaaaagc  29580
tcgcgcgagag cgccctccac cggcattctt aagcacaccc tcataattcc aagagattct  29640
gctcctggtt cacctgcagc agattaacaa tgggaatatc aaaatctctg ccgcgatccc  29700
taagctcctc cctcaacaat aactgtatgt aatctttcat atcatctccg aaattttag    29760
ccatagggcc gccaggaata agagcagggc aagccacatt acagataaag cgaagtcctc  29820
cccagtgwgc attgccaaat gtaagattga aataagcatg ctggctagac cctgtgtatat  29880
cttccagata actggacaga aaatcaggca agcaatttt aagaaaatca acaaaagaaa   29940
agtcgtccag gtgcaggttt agagcctcag gaacaacgat caaggagtgc                30000
gttcagcat ggttagtgtt ttttggtga tctgtagaac aaaaaataa catgcaatat      30060
taaaccatgc tagcctggcg aacaggtggg taaatcactc tttccagcac caggcaggct   30120
acggggtctc cggcgcgacc ctcgtagaag ctgtcgccat gattgaaaag catcaccgag   30180
agaccttccc ggtggccggc atggatgatt cgagaagaag catacactcc gggaacattg   30240
gcatccgtga gtgaaaaaaa gcgacctata aagcctcggg gcactacaat gctcaatctc   30300
```

-continued

```
aattccagca aagccacccc atgcggatgg agcacaaaat tggcaggtgc gtaaaaaatg  30360
taattactcc cctcctgcac aggcagcaaa gccccgctc cctccagaaa cacatacaaa  30420
gcctcagcgt ccatagctta ccgagcacgg caggcgcaag agtcagagaa aaggctgagc  30480
tctaacctga ctgcccgctc ctgtgctcaa tatatagccc taacctacac tgacgtaaag  30540
gccaaagtct aaaaataccc gccaaataat cacacacgcc cagcacacgc ccagaaaccg  30600
gtgacacact caaaaaaata cgcgcacttc ctcaaacgcc caaaactgcc gtcatttccg  30660
ggttcccacg ctacgtcatc aaaacacgac tttcaaattc cgtcgaccgt taaaaacgtc  30720
acccgccccg cccctaacgg tcgcccgtct ctcagccaat cagcgccccg catccccaaa  30780
ttcaaacacc tcatttgcat attaacgcgc acaaaaagtt tgaggtatat tattgatgat  30840
gg                                                                 30842

SEQ ID NO: 11          moltype = DNA  length = 1107
FEATURE                Location/Qualifiers
source                 1..1107
                       mol_type = other DNA
                       organism = Mycobacterium tuberculosis
SEQUENCE: 11
atggacgcca tgaagagggg cctgtgctgc gtgctgctgc tgtgtggcgc cgtgttcgtg  60
tcccccagcc aggaaatcca cgcccggttc agacggggca gcatgcagct ggtggacaga  120
gtcagaggcg ccgtgaccgg catgagcaga cggctggtcg tgggagctgt cggagccgct  180
ctggtgtctg gactcgtggg agccgtgggc ggaacagcta cagccggcgc tttcagcaga  240
cccggcctgc ccgtggaata tctgcaggtc cccagcccca gcatgggccg ggacatcaag  300
gtgcagttcc agtctggcgg agccaacagc cctgctctgt acctgctgga cggcctgaga  360
gcccaggacg acttcagcgg ctgggacatc aacacccccg ccttcgagtg gtacgaccag  420
agcggcctgt ctgtggtcat gcctgtgggc ggccagagca gcttctacag cgactggtat  480
cagcccgctt gtggcaaggc cggctgccag acctacaagt gggagacatt cctgaccagc  540
gagctgcccg gctggctgca ggccaacaga cacgtgaagc ccaccggctc tgccgtcgtg  600
ggcctgtcta tggctgccag ctctgccctg accctggcca tctaccaccc ccagcagttc  660
gtgtacgctg gcgccatgtc tggcctgctg gatccttctc aggccatggg acccaccctg  720
atcggactgg ctatgggaga tgccggcgga tacaaggcca gcgacatgtg gggccctaaa  780
gaggaccccg cctggcagag aaacgacccc ctgctgaacg tgggcaagct gatcgccaac  840
aacaccagag tgtgggtgta ctgcggcaac ggcaagctga gcgacctggg cggcaacaac  900
ctgcccgcca agttcctgga aggcttcgtg cggaccagca acatcaagtt ccaggacgcc  960
tacaacgctg gcggcggaca caacggcgtg ttcgacttcc ccgacagcgg cacccacagc  1020
tgggagtatt ggggagccca gctgaatgcc atgaagcccg acctgcagag aggcagcatc  1080
cctaatcctc tgctgggcct ggactga                                  1107

SEQ ID NO: 12          moltype = AA  length = 368
FEATURE                Location/Qualifiers
source                 1..368
                       mol_type = protein
                       organism = Mycobacterium tuberculosis
SEQUENCE: 12
MDAMKRGLCC VLLLCGAVFV SPSQEIHARF RRGSMQLVDR VRGAVTGMSR RLVVGAVGAA  60
LVSGLVGAVG GTATAGAFSR PGLPVEYLQV PSPSMGRDIK VQFQSGGANS PALYLLDGLR  120
AQDDFSGWDI NTPAFEWYDQ SGLSVVMPVG GQSSFYSDWY QPACGKAGCQ TYKWETFLTS  180
ELPGWLQANR HVKPTGSAVV GLSMAASSAL TLAIYHPQQF VYAGAMSGLL DPSQAMGPTL  240
IGLAMGDAGG YKASDMWGPK EDPAWQRNDP LLNVGKLIAN NTRVWVYCGN GKLSDLGGNN  300
LPAKFLEGFV RTSNIKFQDA YNAGGGHNGV FDFPDSGTHS WEYWGAQLNA MKPDLQRGSI  360
PNPLLGLD                                                       368

SEQ ID NO: 13          moltype = DNA  length = 2274
FEATURE                Location/Qualifiers
misc_feature           1..2274
                       note = Influenza A virus nucleoprotein and matrix protein 1
misc_feature           1495..1515
                       note = Linker
misc_feature           1..1494
                       note = Nucleoprotein sequence
misc_feature           1516..2274
                       note = Matrix protein 1 sequence
source                 1..2274
                       mol_type = other DNA
                       organism = unidentified
SEQUENCE: 13
atggccagcc agggcaccaa gcggagctac gagcagatgg aaaccgacgg cgaccggcag  60
aacgccaccg agatccgggc cagcgtgggc aagatgatcg acggcatcgg ccggttctac  120
atccagatgt gcaccgagct gaagctgtcc gactacgagg gccggctgat ccagaacagc  180
ctgaccatcg agaagatggt gctgtccgcc ttcgacgagc ggcggaacag atacctggaa  240
gagcacccca gcgccggcaa ggaccccaag aaaaccggcg gacccatcta ccggcgggtg  300
gacggcaagt ggatgcggga gctggtgctg tacgacaaag aggaaatccg gcggatctgg  360
cggcaggcca acaacggcga ggacgccaca gccggcctga cccacatgat gatctggcac  420
agcaacctga acgacaccac ctaccagcgg accagggccc tcgtgcggac cggcatggac  480
ccccggatgt gcagcctgat gcagggcagc acactgccca gaagaagcgg agctgccgga  540
gccgccgtga agggcatcgg caccatggtg atggaactga tccggatggt gaagcggggc  600
atcaacgacc ggaatttttg gagggggcgag aacggcagaa agactagaag cgcctacgag  660
cggatgtgca acatcctgaa gggcaagttc cagacagccg cccagcgggc catggtggac  720
caggtccggg agagccggaa ccccggcaac gccgagatcg aggacctgat cttcctggcc  780
cggtccgccc tgatcctgcg gggcagcgtg gcccacaaga gctgcctgcc cgcctgcgtg  840
```

-continued

```
tacggccctg  ccgtgagcag  cggctacgac  ttcgagaaag  agggctacag  cctggtcggc   900
atcgacccct  tcaagctgct  gcagaacagc  caggtgtaca  gcctgatccg  gcccaacgag   960
aaccccgccc  acaagtccca  gctggtctgg  atggcctgcc  acagcgccgc  cttcgaggat  1020
ctgcggctgc  tgtccttcat  ccggggcacc  aaggtgtccc  caggggcaa   gctgtccacc  1080
agaggcgtgc  agatcgccag  caacgagaac  atggacaatg  tgggcagcag  cacccctgga  1140
ctgcggagcg  gctactgggc  catccggacc  cggtccggcg  gcaacaccaa  ccagcagcgg  1200
gccagcgccg  gacagatcag  cgtgcagccc  accttctccg  tgcagcggaa  cctgcccttc  1260
gagaagagca  ccgtgatggc  cgccttcacc  ggcaacaccg  agggccggac  cagcgacatg  1320
cgggccgaga  ttatccggat  gatggaaggc  gccaagcccg  aggaagtgag  cttccggggc  1380
agggcgtgt   tcgagctgtc  cgatgagaag  gccaccaacc  ccatcgtgcc  cagcttcgag  1440
atgagcaacg  agggcagcta  cttcttcggc  gacaacgccg  aggaatacga  caatggcggc  1500
ggaccaggcg  gcgaatgag   cctgctgacc  gaggtggaga  cctacgtgct  gtccatcgtg  1560
cctagcggcc  ctctgaaggc  cgagatcgcc  cagcggctgg  aagatgtgtt  cgccggcaag  1620
aacaccgacc  tggaagccct  gatggaatgg  ctgaaaaccc  ggcccatcct  gagcccccta  1680
accaagggca  tcctgggctt  cgtgttcacc  ctgaccgtgc  ccagcgagcg  ggcctgcag   1740
cggcggagat  tcgtgcagaa  cgccctgaac  ggcaacggcg  accccaacaa  catggataag  1800
gccgtgaagc  tgtaccggaa  gctgaagcgg  agatcaccct  tccacggcgc  caagagatc   1860
gccctgagct  acagcgccgg  agccctggcc  agctgcatgg  gcctgatcta  caaccggatg  1920
ggcgccgtga  ccaccgaggt  ggccttcggc  ctggtctgcg  ccacctgcga  gcagatcgcc  1980
gacagccagc  acagatccca  ccggcagatg  gtggccacaa  ccaaccctct  gatcaagcac  2040
gagaaccgga  tggtgctggc  tagcaccacc  gccaaggcca  tggaacagat  ggccggcagc  2100
agcgagcagg  ccgccgaagc  catggaaatc  gccagcagat  ggtgcaggcc  2160
atgcggaccg  tgggcaccca  ccccagcagc  tccaccggcc  tgcggacga   cctgctggaa  2220
aacctgcaga  cctaccagaa  acggatgggg  gtgcagatgc  agcggttcaa  gtga        2274
```

```
SEQ ID NO: 14           moltype = AA   length = 757
FEATURE                 Location/Qualifiers
REGION                  1..757
                        note = Influenza A virus nucleoprotein and matrix protein 1
source                  1..757
                        mol_type = protein
                        organism = unidentified
SEQUENCE: 14
MASQGTKRSY EQMETDGDRQ NATEIRASVG KMIDGIGRFY IQMCTELKLS DYEGRLIQNS   60
LTIEKMVLSA FDERRNRYLE EHPSAGKDPK KTGGPIYRRV DGKWMRELVL YDKEEIRRIW  120
RQANNGEDAT AGLTHMMIWH SNLNDTTYQR TRALVRTGMD PRMCSLMQGS TLPRRSGAAG  180
AAVKGIGTMV MELIRMVKRG INDRNFWRGE NGRKTRSAYE RMCNILKGKF QTAAQRAMVD  240
QVRESRNPGN AEIEDLIFLA RSALILRGSV AHKSCLPACV YGPAVSSGYD FEKEGYSLVG  300
IDPFKLLQNS QVYSLIRPNE NPAHKSQLVW MACHSAAFED LRLLSFIRGT KVSPRGKLST  360
RGVQIASNEN MDNMGSSTLE LRSGYWAIRT RSGGNTNQQR ASAGQISVQP TFSVQRNLPF  420
EKSTVMAAFT GNTEGRTSDM RAEIIRMMEG AKPEEVSFRG RGVFELSDEK ATNPIVPSFE  480
MSNEGSYFFG DNAEEYDNGG GPGGGMSLLT EVETYVLSIV PSGPLKAEIA QRLEDVFAGK  540
NTDLEALMEW LKTRPILSPL TKGILGFVFT LTVPSERGLQ RRRFVQNALN GNGDPNNMDK  600
AVKLYRKLKR EITFHGAKEI ALSYSAGALA SCMGLIYNRM GAVTTEVAFG LVCATCEQIA  660
DSQHRSHRQM VATTNPLIKH ENRMVLASTT AKAMEQMAGS SEQAAEAMEI ASQARQMVQA  720
MRTVGTHPSS STGLRDDLLE NLQTYQKRMG VQMQRFK                           757
```

```
SEQ ID NO: 15           moltype = AA   length = 9
FEATURE                 Location/Qualifiers
REGION                  1..9
                        note = Polypeptide linker sequence
source                  1..9
                        mol_type = protein
                        organism = synthetic construct
SEQUENCE: 15
IPNPLLGLD                                                            9
```

```
SEQ ID NO: 16           moltype = DNA  length = 2948
FEATURE                 Location/Qualifiers
source                  1..2948
                        mol_type = other DNA
                        organism = synthetic construct
misc_feature            1..2948
                        note = Chimpanzee adenovirus Ch68
SEQUENCE: 16
gtaggtgtca gctgatcgcc agggtattta aacctgcgct ctccagtcaa gaggccactc   60
ttgagtgcca gcgagaagag ttttctcctc cgcgccgcga gtcagatcta cactttgaaa  120
gatgaggcac ctgagagacc tgcccgatga gaaaatcatc atcgcttccg ggaacgagat  180
tctggaactg gtggtaaatg ccatgatggg cgacgaccct ccggagcccc ccactccatt  240
tgagacacct tcgctgcacg atttgtatga tctggaggtg gatgtgcccg gaacgatcc   300
caatgaggag gcgtaaatg atttttttag cgatgccgcg ctgctagctg ccgaggaggc  360
ttcgagctct agctcagaca gcgactcttc actgcatacc cctagacccg gcagaggtga  420
gaaaaagatc cccgagctta aggggaaga  gatggacttc gctgctatg  aggaatgctt   480
gccccgcagc gatgatgagg acgagcaggc gatcagaac gcaggagtgca  540
agccgccagc gagagctttg cgctggactc cccgcctctg ccggacacg  gctgtaagtc  600
ttgtgaattt catcgcatga atactggaga taaagctgtg ttgtgtgcac tttgctatat  660
gagagcttac aaccattgtg tttacagtaa gtgtgattaa gttgaacttt agagggaggc  720
agagagcagg gtgactgggc gatgactggt ttatttatgt atatatgttc tttatatagg  780
tcccgtctct gacgcagatg atgagacccc cactacaaag tccacttcgt caccccaga   840
```

```
aattggcaca tctccacctg agaatattgt tagaccagtt cctgttagag ccactgggag   900
gagagcagct gtggaatgtt tggatgactt gctacagggt ggggttgaac ctttggactt   960
gtgtaccggg aaacgcccca ggcactaagt gccacacatg tgtgtttact tgaggtgatg  1020
tcagtattta tagggtgtgg agtgcaataa aaaatgtgtt gactttaagt gcgtggttta  1080
tgactcaggg gtggggactg tgagtatata agcaggtgca gacctgtgtg gttagctcag  1140
agcggcatgg agatttggac ggtcttgaaa gactttcaca agactagaca gctgctagag  1200
aacgcctcga acggagtctc ttacctgtgg agattctgct tcggtggcga cctagctagg  1260
ctagtctaca gggccaaaca ggattatagt gaacaatttg aggttatttt gagagagtgt  1320
tctggtcttt ttgacgctct taacttgggc catcagtctc actttaacca gaggatttcg  1380
agagcccttg attttactac tcctggcaga accactgcag cagtagcctt ttttgctttt  1440
attcttgaca aatggagtca agaaacccat ttcagcaggg attaccagct ggatttctta  1500
gcagtagctt tgtggagaac atggaagtgc agcgcctga atgcaatctc cggctacttg  1560
ccggtacagc cgctagacac tctgaggatc ctgaatctcc aggagagtcc cagggcacgc  1620
caacgtcgcc agcagcagca gcaggaggag gatcaagaag agaacccgag agccggcctg  1680
gaccctccgg cggaggagga ggagtagctg acctgtttcc tgaactgcgc cgggtgctga  1740
ctaggtcttc gagtggtcgg gagaggggga ttaagcggga gaggcatgat gagactaatc  1800
acagaactga actgactgtg ggtctgatga gtcgcaagcg cccagaaaca gtgtggtggc  1860
atgaggtgca gtcgactggc acagatgagg tgtcggtgat gcatgagagg ttttctcttg  1920
aacaagtcaa gacttgttgg ttagagcctg aggatgattg ggaggtagcc atcaggaatt  1980
atgccaagct ggctctgagg ccagacaaga agtacaagat tactaagctg ataaatatca  2040
gaaatgcctg ctacatctca gggaatgggg ctgaagtgga gatctgtctc caggaaaggg  2100
tggctttcag atgctgcatg atgaatatgt acccgggagt ggtgggcatg gatggggtta  2160
cctttatgaa catgaggttc aggggagatg ggtataatgg cacggtcttt atggccaata  2220
ccaagctgac agtccatggc tgctccttct ttgggtttaa taacacctgc atcgaggcct  2280
ggggtcaggt cggtgtgagg ggctgcagtt tttcagccaa ctggatgggg gtcgtgggca  2340
ggaccaagag tatgctgtcc gtgaagaaat gcttgtttga gaggtgccac ctggggggtga 2400
tgagcgaggg cgaagccaga atccgccact gcgcctctac cgagacgggc tgctttgtgc  2460
tgtgcaaggc caatgctaag atcaagcata atatgatctg tggagcctcg gacgagcgcg  2520
gctaccagat gctgacctgc gccggcggga acagccatat gctggccacc gtacatgtgg  2580
cttcccatgc tcgcaagccc tggcccgagt tcagacacaa tgtcatgacc aggtgcaata  2640
tgcatctggg gtcccgccga ggcatgttca tgccctacca gtgcaacctg aattatgtga  2700
aggtgctgct ggagcccgat gccatgtcca gagtgagcct gacggggggtg tttgacatga 2760
atgtggaggt gtggaagatt ctgagatatg atgaatccaa gaccaggtgc cgagcctgcg  2820
agtgcggagg gaagcatgcc aggttccagc ccgtgtgtgt ggatgtgacg gaggacctgc  2880
gacccgatca tttggtgttg ccctgcaccg ggacggagtt cggttccagc ggggaagaat  2940
ctgactag                                                          2948
SEQ ID NO: 17         moltype = DNA   length = 4707
FEATURE               Location/Qualifiers
source                1..4707
                      mol_type = other DNA
                      organism = synthetic construct
misc_feature          1..4707
                      note = Chimpanzee adenovirus C68
SEQUENCE: 17
atgtcccatg gtggcgcagc tgacctagct cggcttcgac acctggacca ctgccgccgc    60
ttccgctgct tcgctcggga tctcgccgag tttgcctact ttgagctgcc cgaggagcac   120
cctcagggcc cggcccacgg agtgcggatc gtcgtcgaag ggggcctcga ctcccacctg   180
cttcggatct tcagccagcg tccgatcctg gtcgagcgcg agcaaggaca gacccttctg   240
actctgtact gcatctgcaa ccaccccggc ctgcatgaaa gtctttgttg tctgctgtgt   300
actgagtata ataaaagctg agatcagcga ctactccgga cttccgtgtg ttcctgcatc   360
catcaaccag tctttgttct tcaccggaa cgagaccgag ctccagctcc agtgtaagc    420
ccacaagaag tacctcacct ggctgttcca gggctcccg atcgccgttg tcaaccactg    480
cgacaacgac ggagtcctgc tgagcggcc tgccaacctt acttttttcca cccgcagaag   540
caagctccag ctcttccaac cctcctccc cgggacctat cagtgcgtct cgggaccctg    600
ccatcacacc ttccacctga tcccgaatac cacagcgtcg ctcccgcta ctaacaacca    660
aactaacctc caccaacgcc accgtcgcga cctttctgaa tctaatacta ccacccacac   720
cggaggtgag ctccgaggtc aaccaacctc tgggatttac tacggcccct gggaggtggt   780
tgggttaata gcgctaggcc tagttgcggg tgggcttttg gttctctgct acctataact   840
ccctttgctgt tcgtacttag tggtgcgtgt ttgctggtt aagaaatggg gaagatcacc   900
ctagtgagct gcggtgcgct ggtggcggtg ttgctttcga ttgtgggact gggcggtgcg   960
gctgtagtga aggagaaggc cgatccctgc ttgcatttca atccaacaa atgccagctg  1020
agttttcagc ccgatggcaa tcggtgcgcg gtactgatca agtgcggatg ggaatgcgag  1080
aacgtgagaa tcgagtcaa taacaagact cggaacaatca ctctcgcgtc cgtgtggcag  1140
cccgggggacc ccgagtggta caccgtctct gtccccggtg ctgacggctc ccgcgcacc  1200
gtgaataata cttcatttt tgcgcacatg tgcgacacgg tcatgtggat gagcaagcag  1260
tacgatatgt ggccccccac gaaggagaac atcgtggtct tctccatcgc ttacagcctg  1320
tgcacggcgc taatcaccgc tatcgtgtgc ctgagcattc acatgctcat cgctattcgc  1380
cccagaaata tgccgaaaa agaaaaacag ccataacgtt tttttcaca ccttttcag   1440
accatggcct ctgttaaatt tttgctttta tttgccagtc tcattgccgt cattcatgg   1500
atgagtaatg agaaaattac tatttacact ggcactaatc acacattgaa aggtccagaa  1560
aaagccacag aagtttcatg gtattgttat tttaatgaat cagatgtatc tactgaactc  1620
tgtgaaaaca ataacaaaaa aaatgagagc attactctca tcaagtttca atgtggatct  1680
gacttaacc taattaacat cactagagac tatgtaggta tgtattatgg aactacagca  1740
ggcatttcgg acatggaatt ttatcaagtt tctgtgtctg aacccaccac gcctagaatg  1800
accacaacca caaaaactac acctgttacc actatgcagc tcactaccaa taacatttt   1860
gccatgcgtc aaatggtcaa caatagcact caacccaccc cacccagtga ggaaattccc  1920
aaatccatga ttggcattat tgttgctgta gtggtgtgca ttgtgatcat cgccttgtgc  1980
atggtgtact atgccttctg ctacagaaag cacagactga acgacaagct ggaacactta  2040
```

```
ctaagtgttg aatttaatt ttttagaacc atgaagatcc taggcctttt aattttttct    2100
atcattacct ctgctctatg caattctgac aatgaggacg ttactgtcgt tgtcggatca    2160
aattatacac tgaaaggtcc agcgaagggt atgctttcgt ggtattgcta ttttggatct    2220
gacactacag aaactgaatt atgcaatctt aagaatggca aaattcaaaa ttctaaaatt    2280
aacaattata tatgcaatgg tactgatctg atactcctca atatcacgaa atcatatgct    2340
ggcagttaca cctgccctgg agatgatgct gacagtatga ttttttacaa agtaactgtt    2400
gttgatccca ctactccacc tccacccacc acaactactc acaccacaca cacagatcaa    2460
accgcagcag aggaggcagc aaagttagcc ttgcaggtcc aagacagttc atttgttggc    2520
attaccccta cacctgatca gcggtgtccg gggctgctag tcagcggcat tgtcggtgtg    2580
ctttcgggat tagcagtcat aatcatctgc atgttcattt ttgcttgctg ctatagaagg    2640
ctttaccgac aaaaatcaga cccactctg aacctctatg tttaattttt tccagagtca    2700
tgaaggcagt tagcgctcta gttttttgtt ctttgattgg cattgttttt tgcaatccta    2760
ttcctaaagt tagctttatt aaagatgtga atgttactga ggggggcaat gtgacactgg    2820
taggtgtaga gggtgctgaa aacaccacct ggacaaaata ccacctcaat gggtggaaag    2880
atatttgcaa ttggagtgta ttagtttata catgtgaggg agttaatctt accattgtca    2940
atgccacctc agctcaaaat ggtagaattc aaggacaaag tgtcagtgta tctaatgggt    3000
attttaccca acatacttt atctatgacg ttaaagtcat accactgcct acgcctagcc    3060
cacctagcac taccacacag acaacccaca ctacacagac aaccacatac agtacattaa    3120
atcagcctac caccactaca gcagcagagg ttgccagctc gtctgggtc cgagtggcat    3180
ttttgatgtg ggccccatct agcagtccca ctgctagtac caatgagcag actactgaat    3240
ttttgtccac tgtcgagagc cacaccacag ctacctccag tgccttctct agcaccgcca    3300
atctctcctc gctttcctct acaccaatca gtcccgctac tactcctagc ccgctcctc    3360
ttcccactcc cctgaagcaa acagacggcg catgcaatgg cagatcacc ctgctcattg    3420
tgatcgggtt ggtcatcctg gccgtgttgc tctactacat cttctgccgc cgcattccca    3480
acgcgcaccg caagccggtc tacaagccca tcattgtcgg gcagcggag ccgcttcagg    3540
tggaaggggg tctaaggaat cttctcttct cttttacagt atggtgattg aactatgatt    3600
cctagacaat tcttgatcac tattcttatc tgcctcctcc aagtctgtgc caccctcgct    3660
ctggtggcca acgccagtcc agactgtatt gggcccttcg cctcctacgt gctctttgcc    3720
ttcaccacct gcatctgctg ctgtagcata gtctgcctgc ttatcacctt cttccagttc    3780
attgactgga tctttgtgcg catcgcctac ctgcgccacc accccagta ccgcgaccag    3840
cgagtggcgc ggctgctcag gctcctctga taagcatgcg ggctctgcta cttctcgcgc    3900
ttctgctgtt agtgctcccc cgtcccgcg accccggtc cccacccag tccccgagg    3960
aggtccgcaa atgcaaattc caagaaccct ggaaattcct caaatgctac cgccaaaaat    4020
cagacatgca tcccagctgg atcatgatca ttgggatcgt gaacattctg gcctgcacc    4080
tcatctcctt tgtgatttac ccctgctttg acttttggttg gaactcgcca gaggcgctct    4140
atctcccgcc tgaacctgac acaccaccac agcaacctca ggcacacgca ctaccaccac    4200
tacagcctag gccacaatac atgcccatat tagactatga ggccgagcca cagcgaccca    4260
tgctcccgc tattagttac ttcaatctaa ccggcggaga tgactgaccc actggccaac    4320
aacaagtca acgaccttct cctggacatg gacggccgc cctcggagca gcgactcgcc    4380
caacttcgca ttcgccagca gcaggagaga gccgtcaagg agctgcagga tgcggtggcc    4440
atccaccagt gcaagagagg catcttctgc ctggtgaaac aggccaagat ctcctacgag    4500
gtcactccaa acgaccatcg cctctcctac gagctcctgc agcagcgcca gaagttcacc    4560
tgcctggtcg gagtcaaccc catcgtcatc acccagcagt ctggcgatac caaggggtgc    4620
atccactgct cctgcgactc ccccgactgc gtccacactc tgatcaagac cctctgcggc    4680
ctccgcgacc tcctcccat gaactaa                                         4707
```

```
SEQ ID NO: 18          moltype = AA  length = 933
FEATURE                Location/Qualifiers
source                 1..933
                       mol_type = protein
                       organism = synthetic construct
REGION                 1..933
                       note = Chimpanzee adenovirus C68
SEQUENCE: 18
MATPSMLPQW AYMHIAGQDA SEYLSPGLVQ FARATDTYFS LGNKFRNPTV APTHDVTTDR   60
SQRLTLRFVP VDREDNTYSY KVRYTLAVGD NRVLDMASTY FDIRGVLDRG PSFKPYSGTA  120
YNSLAPKGAP NTCQWTYKAD GETATEKTYT YGNAPVQGIN ITKDGIQLGT DTDDQPIYAD  180
KTYQPEPQVG DAEWHDITGT DEKYGGRALK PDTKMKPCYG SFAKPTNKEG GQANVKTGTG  240
TTKEYDIDMA FFDNRSAAAA GLAPEIVLYT ENVDLETPDT HIVYKAGTDD SSSSINLGQQ  300
AMPNRPNYIG FRDNFIGLMY YNSTGNMGVL AGQASQLNAV VDLQDRNTEL SYQLLLDSLG  360
DRTRYFSMWN QAVDSYDPDV RIIENHGVED ELPNYCFPLD AVGRTDTYQG IKANGTDQTT  420
WTKDDSVNDA NEIGKGNPFA MEINIQANLW RNFLYANVAL YLPDSYKYTP ANVTLPTNTN  480
TYDYMNGRVV APSLVDSYIN IGARWSLDPM DNVPFNHHR NAGLRYRSML LGNGRYVPFH  540
IQVPQKFFAI KSLLLLPGSY TYEWNFRKDV NMILQSSLGN DLRTDGASIS FTSINLYATF  600
FPMAHNTAST LEAMLRNDTN DQSFNDYLSA ANMLYPIPAN ATNVPISIPS RNWAAFRGWS  660
FTRLKTKETP SLGSGFDPYF VYSGSIPYLD GTFYLNHTFK KVSITFDSSV SWPGNDRLLT  720
PNEFEIKRTV DGEGYNVAQC NMTKDWFLVQ MLAHYNIGYQ GFYVPEGYKD RMYSFFRNFQ  780
PMSRQVVDEV NYKDYQAVTL AYQHNNSGFV GYLAPTMRQG QPYPANYPYP LIGKSAVTSV  840
TQKKFLCDRV MWRIPFSSNF MSMGALTDLG QNMLYANSAH ALDMNFEVDP MDESTLLYVV  900
FEVFDVVRVH QPHRGVIEAV YLRTPFSAGN ATT                               933

SEQ ID NO: 19          moltype = AA  length = 425
FEATURE                Location/Qualifiers
source                 1..425
                       mol_type = protein
                       organism = synthetic construct
REGION                 1..425
                       note = Chimpanzee adenovirus C68
SEQUENCE: 19
```

```
MSKKRVRVDD DFDPVYPYDA DNAPTVPFIN PPFVSSDGFQ EKPLGVLSLR LADPVTTKNG      60
EITLKLGEGV DLDSSGKLIS NTATKAAAPL SFSNNTISLN MDHPFYTKDG KLSLQVSPPL     120
NILRTSILNT LALGFGSGLG LRGSALAVQL VSPLTFDTDG NIKLTLDRGL HVTTGDAIES     180
NISWAKGLKF EDGAIATNIG NGLEFGSSST ETGVDDAYPI QVKLGSGLSF DSTGAIMAGN     240
KEDDKLTLWT TPDPSPNCQI LAENDAKLTL CLTKCGSQIL ATVSVLVVGS GNLNPITGTV     300
SSAQVFLRFD ANGVLLTEHS TLKKYWGYRQ GDSIDGTPYT NAVGFMPNLK AYPKSQSSTT     360
KNNIVGQVYM NGDVSKPMLL TITLNGTDDS NSTYSMSFSY TWTNGSYVGA TFGANSYTFS     420
YIAQE                                                                 425

SEQ ID NO: 20           moltype = AA  length = 534
FEATURE                 Location/Qualifiers
source                  1..534
                        mol_type = protein
                        organism = synthetic construct
REGION                  1..534
                        note = Chimpanzee adenovirus C68
SEQUENCE: 20
MMRRAYPEGP PPSYESVMQQ AMAAAAMQPP LEAPYVPPRY LAPTEGRNSI RYSELAPLYD      60
TTRLYLVDNK SADIASLNYQ NDHSNFLTTV VQNNDFTPTE ASTQTINFDE RSRWGGQLKT     120
IMHTNMPNVN EFMYSNKFKA RVMVSRKTPN GVTVTEDYDG SQDELKYEWV EFELPEGNFS     180
VTMTIDLMNN AIIDNYLAVG RQNGVLESDI GVKFDTRNFR LGWDPVTELV MPGVYTNEAF     240
HPDIVLLPGC GVDFTESRLS NLLGIRKRQP FQEGFQIMYE DLEGGNIPAL LDVDAYEKSK     300
EDAAAEATAA VATASTEVRG DNFASAAAVA AAEAAETESK IVIQPVEKDS KNRSYNVLPD     360
KINTAYRSWY LAYNYGDPEK GVRSWTLLTT SDVTCGVEQV YWSLPDMMQD PVTFRSTRQV     420
SNYPVVGAEL LPVYSKSFFN EQAVYSQQLR AFTSLTHVFN RFPENQILVR PPAPTITTVS     480
ENVPALTDHG TLPLRSSIRG VQRVTVTDAR RRTCPYVYKA LGIVAPRVLS SRTF           534

SEQ ID NO: 21           moltype = AA  length = 524
FEATURE                 Location/Qualifiers
source                  1..524
                        mol_type = protein
                        organism = synthetic construct
REGION                  1..524
                        note = Rabies virus
SEQUENCE: 21
MVPQALLFVP LLVFPLCFGK FPIYTIPDKL GPWSPIDIHH LSCPNNLVVE DEGCTNLSGF      60
SYMELKVGYI LAIKMNGFTC TGVVTEAETY TNFVGYVTTT FKRKHFRPTP DACRAAYNWK     120
MAGDPRYEES LHNPYPDYRW LRTVKTTKES LVIISPSVAD LDPYDRSLHS RVFPSGKCSG     180
VAVSSTYCST NHDYTIWMPE NPRLGMSCDI FTNSRGKRAS KGSETCGFVD ERGLYKSLKG     240
ACKLKLCGVL GLRLMDGTWV AMQTSNETKW CPPDQLVNLH DFRSDEIEHL VVEELVRKRE     300
ECLDALESIM TTKSVSFRRL SHLRKLVPGF GKAYTIFNKT LMEADAHYKS VRTWNEILPS     360
KGCLRVGGRC HPHVNGVFFN GIILGPDGNV LIPEMQSSLL QQHMELLESS VIPLVHPLAD     420
PSTVFKDGDE AEDFVEVHLP DVHNQVSGVD LGLPNWGKYV LLSAGALTAL MLIIFLMTCC     480
RRVNRSEPTQ HNLRGTGREV SVTPQSGKII SSWESHKSGG ETRL                     524
```

ADENOVIRAL VECTOR

This application is a continuation of U.S. patent application Ser. No. 17/587,376 filed Jan. 28, 2022, which is a continuation of U.S. patent application Ser. No. 16/310,281 filed Dec. 14, 2018, which is a U.S. National Stage of International Patent Application No. PCT/GB2017/051851, filed Jun. 23, 2017, which claims the benefit of Great Britain Patent Application No. 1610967.0 filed Jun. 23, 2016 entitled "Adenoviral Vector", each of which is incorporated by reference herein in its entirety.

This application contains a Sequence Listing which has been submitted electronically in XML file format and is hereby incorporated by reference in its entirety. Said XML file, created on Mar. 20, 2024, is named 119987-5002-US02_Sequence Listing_20240320 and is 149,837 bytes in size.

The present invention relates to novel adenoviral vectors, immunogenic compositions thereof and their use in medicine.

All publications, patents and patent applications cited herein are incorporated in full by reference.

BACKGROUND

Traditionally, vaccines have been based on whole inactivated or attenuated pathogens. However, for many infectious diseases such as malaria, this approach is impractical and the focus of research has changed to the development of 'subunit vaccines' expressing only those pathogen-derived antigens that induce immune correlates of protection.

Subunit vaccines present an antigen to the immune system without introducing a whole infectious organism. One such method involves the administration of a specific, isolated protein from an infectious organism. However, this technique often induces only a weak immune response and the isolated proteins may have a different three-dimensional structure than the protein in its normal context, resulting in the production of antibodies that may not recognize the infectious organism.

An alternative method has therefore been developed which utilizes viral vectors for the delivery of antigens. Viruses are obligate intracellular parasites which replicate by transfecting their DNA into a host cell, and inducing the host cell to express the viral genome. This reproductive strategy has been harnessed to create vectored vaccines by creating recombinant, non-replicating viral vectors which carry one or more heterologous transgenes. Transfection or transduction of the recombinant viral genome into the host cell results in the expression of the heterologous transgene in the host cell. When the heterologous transgene encodes an antigen, for example, expression of the antigen within the host cell can elicit a protective or therapeutic immune response by the host immune system. As such, the viral vectors may function as effective vaccines. Alternatively, the heterologous transgene may encode a functional allele of a gene, expression of which can be used to counteract the effects of a deleterious mutant allele of the gene, in a process known as gene therapy.

Particularly suitable for use as viral vectors are adenoviruses. Adenoviruses are non-enveloped viruses, approximately 90-100 nm in diameter, comprising a nucleocapsid and a linear double stranded DNA genome. The viral nucleocapsid comprises penton and hexon capsomers. A unique fibre is associated with each penton base and aids in the attachment of the virus to the host cell via the Coxsackie-adenovirus receptor on the surface of the host cell. Over 50 serotype strains of adenoviruses have been identified, most of which cause respiratory tract infections, conjunctivitis and gastroentiritus in humans. Rather than integrating into the host genome, adenoviruses normally replicate as episomal elements in the nucleus of the host cell. The genome of adenoviruses comprises 4 early transcriptional units (E1, E2, E3 and E4), which have mainly regulatory functions and prepare the host cell for viral replication. The genome also comprises 5 late transcriptional units (L1, L2, L3, L4 and L5), which encode structural proteins including the penton (L2), the hexon (L3), the scaffolding protein (L4) and the fiber protein (L5), which are under the control of a single promoter. Each extremity of the genome comprises an Inverted Terminal Repeat (ITR) which is necessary for viral replication.

Recombinant adenoviruses were originally developed for gene therapy, but the strong and sustained transgene-specific immune responses elicited by these gene delivery agents prompted their use as vaccine carriers. In addition to being highly immunogenic, adenoviruses offer many other advantages for clinical vaccine development. The adenoviral genome is relatively small (between 26 and 45 kbp), well characterised and easy to manipulate. The deletion of a single transcriptional unit, E1, renders the virus replication-incompetent which increases its predictability and reduces side effects in clinical applications. Recombinant adenoviruses can accommodate relatively large transgenes, in some cases up to 8 kb, allowing flexibility in subunit design, and have a relatively broad tropism facilitating transgene delivery to a wide variety of cells and tissues. Importantly for clinical applications, methods for scaled-up production and purification of recombinant adenoviruses to high titre are well established. Thus far, subgroup C serotypes AdHu2 or AdHu5 have predominantly been used as vectors.

However, the first generation of vaccine vectors based on the archetypal human adenovirus AdHu5 showed poor efficacy in clinical trials, despite encouraging pre-clinical data[1]. It was subsequently discovered that a large proportion of human adults harbour significant titres of neutralising antibodies to common human serotypes such as AdHu2 and AdHu5, as a result of natural infection. Neutralising antibodies could reduce the potency of viral vector vaccines by blocking viral entry into host cells and hence delivery of the target transgene.

The occurrence of pre-existing anti-vector immunity is being addressed through the development of new adenoviral vectors based on serotypes to which the human population is less likely to have been exposed, including those of chimpanzee origin[2,3]. However, some such chimpanzee adenoviral vectors have limited efficacy on the grounds of unexplained immunity in human populations, varying levels of cross-reactivity with human adenoviruses, and sub-optimal growth in transformed cell lines. In addition, it is advantageous to have a range of different adenoviral vectors available for use in immunising against different diseases, on the grounds that induction of neutralising antibodies against a vector may prevent its re-administration for another indication.

WO2012/172277 describes an adenovirus vector derived from chimpanzee adenovirus AdY25, which addresses some of the above-described problems in the art. This vector is termed ChAdOx1.

However, there continues to be a need in the art for highly immunogenic, non-human adenoviral vectors which effectively deliver the target transgene, minimize the effect of pre-existing immunity to adenovirus serotypes and replicate efficiently in transformed cell lines.

SUMMARY OF INVENTION

In a first aspect, the present invention provides an adenoviral vector comprising the genome of an adenovirus other than AdHu5 and AdY25, wherein the genome of the adenovirus has been modified such that the vector lacks the native E4 locus of the adenovirus and comprises heterologous E4Orf1, E4Orf2 and E4Orf3 coding regions from AdY25.

In a preferred embodiment, the adenoviral vector further comprises heterologous E4Orf4, E4Orf6 and E4Orf6/7 coding regions from AdHu5 in the E4 locus of the adenovirus.

In a preferred embodiment, said adenovirus is C68.

In a preferred embodiment, said adenoviral vector lacks a functional E1 locus and/or lacks an E3 locus.

In a second aspect, the present invention provides an immunogenic composition comprising the adenovirus vector according to the first aspect of the invention and, optionally, one or more additional active ingredients, a pharmaceutically acceptable carrier, diluent, excipient or adjuvant.

Preferably the adjuvant is an oil-in-water adjuvant. For example the adjuvant may comprise squalene. Preferably the adjuvant is selected from MF59®, ASO3, AF03 or Addavax.

A third aspect provides the use of the adenoviral vector according to the first aspect or the immunogenic composition according to the second aspect in medicine. In particular, the adenoviral vector and immunogenic compositions are provided for delivery of a transgene into a host cell, elicitation of an immune response in an animal, boosting an immune response in an animal, treating or preventing at least one disease, inducing an immune response in an animal that will break tolerance to a self-antigen and gene therapy.

A fourth aspect provides a polynucleotide sequence encoding the adenoviral vector according to the first aspect of the present invention.

A fifth aspect of the present invention provides a host cell transduced with the viral vector according to the first aspect of the present invention.

A sixth aspect of the present invention provides a method of producing the viral vector according to the first aspect of the present invention by incorporating the polynucleotide sequence according to the fourth aspect into a Bacterial Artificial Chromosome (BAC).

A seventh aspect of the present invention provides a Bacterial Artificial Chromosome (BAC) clone comprising the polynucleotide sequence according to the fourth aspect of the present invention.

An eighth aspect of the present invention provides a packaging cell line producing the viral vector according to the first aspect of the present invention.

FIGURES

The present invention is described with reference to the following figures:

FIG. 1a-c. Generation of a molecular clone of chimpanzee adenovirus 68 (ChAd68). FIG. 1a) Insertion of ChAd68 genomic DNA into the pBAC 'rescue vector' by gap repair. The E1 left flanking regions 1 (LF1) and 2 (LF2) and terminal right hand side region (RF) are amplified from Chad68 genomic DNA and cloned into pBACe3.6 to produce a BAC adenovirus rescue clone. Recombination occurs between LF1 and LF2 of the isolated ChAd68 genome and the BAC rescue clone and the RF of ChAd68 genome and the BAC rescue clone. The resulting product is a BAC containing an E1 deleted ChAd68 genome. FIG. 1b) Excision of the E3 region of ChAd68 by recombineering. Firstly, the galactokinase gene (GalK) is amplified from pGalK using primers containing sequences homologous to the flanking region of E3 (E3LF and E3RF). The E3 region is replaced by the GalK gene using λ red recombination. The GalK gene is subsequently replaced by a PCR product consisting of E3LF and E3RF, again using λ red recombination. The resulting product is a BAC containing an E1E3 deleted ChAd68 genome. FIG. 1c) Insertion of an antigen cassette at the E1 locus. Firstly, the galactokinase gene (GalK) is amplified from pGalK using primers containing sequences homologous to the flanking region of E1 (LF1 and LF2). The E1 region is replaced by the GalK gene using λ red recombination. The GalK gene is subsequently replaced by a PCR product consisting of LF1-antigen expression cassette-LF2 using λ red recombination. The resulting product is a BAC containing an E1E3 deleted ChAd68 genome with an antigen expression cassette at the E1 locus.

FIG. 2. Insertion of an antigen expression cassette into adenovirus vector using aft recombination sites. A universal cassette expressing a bacteria antibiotic resistance gene and ccdB suicide gene flanked by the specific recombination sequences, attR1 and attR2 is located at the E1 locus and/or the E3 locus of the BAC-adenovirus genome clone. Shuttle plasmids containing an antigen expression cassette flanked by specific recombination sites paired with those present in the genome (attL1/L2) allow site specific recombination in the presence of an enzyme mixture containing bacteriophage A integrase, integration host factor and excisionase.

FIG. 3. Growth of ChAdOx2 compared to ChAd68. E1 complementing Human embryonic kidney 293 cells were infected with a multiplicity of infection (MOI) of 1 virus vector per cell. Samples were taken at 48 and 96 hours post infection. Virus yield was determined by titration in triplicate on HEK293 cells and GFP positive cells counted 48 hours post infection. Results are expressed as the mean $Log_{10}$ fluorescent units (FU) per ml from two separate experiments with standard deviation depicted.

FIG. 4. Immunogenicity of ChAdOx1-eGFP compared to ChAdOx2-eGFP. Female BALB/c mice (4 per group) were injected intramuscularly with $10^8$ infectious units of vector and spleens harvested 2 weeks later to measure the response to GFP by interferon-gamma enyzyme-linked immunosorbent spot (IFN-γ ELISPOT). Results are expressed as spot-forming units (SFUs) per million splenocytes. Mann-Whitney test was used to statistically analyse the results and the Mean with SEM is depicted.

FIG. 5. The study groups (table 1) and current progress of enrollment (table 2) of a phase I clinical trial to determine the safety and immunogenicity of the candidate *Mycobacterium avium* subspecies paratuberculosis (MAP) vaccine ChAdOx2 HAV in healthy adult volunteers.

FIGS. 6 to 11. The proportions of volunteers presenting adverse events (AEs) at different dose groups in the phase I clinical trial investigating the candidate *Mycobacterium avium* subspecies paratuberculosis (MAP) vaccine ChAdOx2 HAV in healthy adult volunteers. Dose of $5\times10^9$ vp for FIGS. 6 and 7 and a dose of $2.5\times10^{10}$ vp for FIGS. 8, 9, 10 and 11.

FIG. 12. Median summed response to all pools of antigens in the HAV vaccine stratified by dose. *p=0.01 Kruskall-Wallis test, with Dunn's multiple comparison test for the $2.5\times10^{10}$ dose group. Lines represent medians.

FIG. 13 shows the tabulated responses for each individual at day 0, day 28 and day 56 in participants immunised with different dosages of the HAV vaccine.

Figure 16:
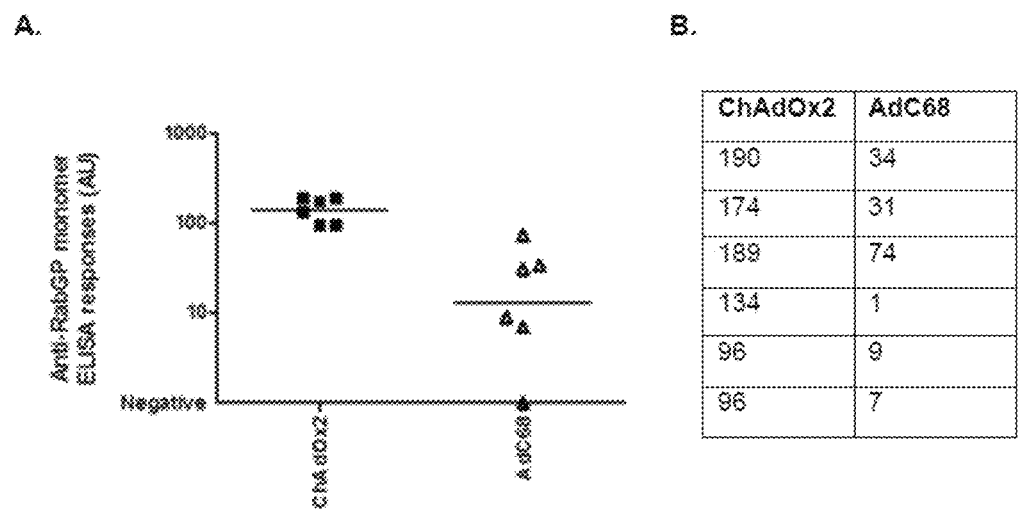

FIG. 16 shows the high immunogenicity of the ChAdOx2 RabGP vaccine construct. p=0.005 comparing ELISA responses (measured in arbitrary antibody units [AU]) by Mann-Whitney test. Immunogenicity of ChAdOx2-RabGP compares favourably to that of AdC68. CD-1 outbred mice were vaccinated intramuscularly with 107 infectious units of either ChAdOx2 or AdC68 expressing rabies glycoprotein. Serum was collected 4 weeks after vaccination. Antibody responses were assessed by ELISA against recombinant rabies glycoprotein, and the result shown in graph A and table B.

DETAILED DESCRIPTION

The present invention relates to novel adenoviral vectors derived from an adenovirus other than AdHu5 and AdY25, immunogenic compositions thereof and their use in medicine.

The invention provides an adenoviral vector comprising the genome of an adenovirus other than AdHu5 and AdY25, wherein the genome of the adenovirus has been modified such that the vector lacks the native E4 locus of the adenovirus and comprises heterologous E4Orf1, E4Orf2, and E4Orf3 coding regions from AdY25.

The adenovirus E4 region comprises at least six Open Reading Frames (ORFs or Orfs). Preferably, the native E4 locus of the adenovirus is deleted.

In a preferred embodiment, the adenovirus is a chimpanzee adenovirus, C68 (also known as C9, Pan6 and sAd25). The nucleotide sequence of C68 is provided as SEQ ID NO. 1. The complete genome of simian adenovirus 25 (i.e. C68) has been deposited and assigned GenBank accession number AC_000011.

According to the invention, the genome of the adenovirus has been modified such that the vector lacks the native E4 locus of the adenovirus. The E4 region of C68 is provided herein as SEQ ID NO. 2.

Furthermore, according to the invention, the genome of the adenovirus is modified such that the vector and comprises heterologous E4Orf1, E4Orf2, and E4Orf3 coding regions from AdY25. AdY25 is a chimpanzee adenovirus described in detail in WO2012/172277.

The complete nucleotide sequence of AdY25 is provided in SEQ ID NO. 6.

The amino acid sequence of E4Orf1 from AdY25 is provided herein as SEQ ID NO. 3. The corresponding nucleotide sequence is nucleotides 35930 to 36304 of SEQ ID NO. 6.

The amino acid sequence of E4Orf2 from AdY25 is provided herein as SEQ ID NO. 4. The corresponding nucleotide sequence is nucleotides 35491 to 35880 of SEQ ID NO. 6.

The amino acid sequence of E4Orf3 from AdY25 is provided herein as SEQ ID NO. 5. The corresponding nucleotide sequence is nucleotides 35141 to 35494 of SEQ ID NO. 6.

In a preferred embodiment, the adenoviral vector further comprises heterologous E4Orf4, E4Orf6, and E4Orf6/7 coding regions from AdHu5.

AdHu5 is human serotype 5 adenovirus. The amino acid sequence of E4Orf4 from AdHu5 is provided herein as SEQ ID NO. 7. The amino acid sequence of E4Orf6 from AdHu5 is provided herein as SEQ ID NO. 8. The amino acid sequence of E4Orf6/7 from AdHu5 is provided herein as SEQ ID NO. 9.

As the skilled person will be aware, adenoviral vectors based on the adenovirus C68 are referred to in the art by various names, including AdCh68, AdC68, ChAd68 and sAdV25 (see, for example, Abbink et al., J Virol. 2015 February; 89(3):1512-22 (PubMed ID: 25410856) and Jeyanathan et al., Mucosal Immunol. 2015 November; 8(6): 1373-87 (PubMed ID: 25872483). These names are also used interchangeably herein.

The vector of the present invention preferably comprises a capsid derived from chimpanzee adenovirus C68. Preferably, the capsid comprises the native or wild-type C68 capsid proteins, including penton proteins, hexon proteins, fibre proteins and/or scaffolding proteins. However, one of skill in the art will readily appreciate that small modifications can be made to the capsid proteins without adversely altering vector tropism.

In a particularly preferred embodiment, the vector capsid comprises one or more capsid proteins selected from the group consisting of:
  (a) a hexon protein encoded by the coding sequence corresponding to nucleotides 18315 to 21116 of SEQ ID NO. 1 or a sequence substantially identical thereto;
  (b) a penton protein encoded by the coding sequence corresponding to nucleotides 13884 to 15488 of SEQ ID NO. 1, or a sequence substantially identical thereto; and
  (c) a fibre protein encoded by the coding sequence corresponding to nucleotides 32134 to 33411 of SEQ ID NO. 1, or a sequence substantially identical thereto.

Preferably, the hexon protein comprises the amino acid sequence of SEQ ID NO. 18, or an amino acid sequence substantially identical to SEQ ID NO. 18.

Preferably, the penton protein comprises the amino acid sequence of SEQ ID NO. 19, or an amino acid sequence substantially identical to SEQ ID NO. 19.

Preferably, the fiber protein comprises the amino acid sequence of SEQ ID NO. 20, or an amino acid sequence substantially identical to SEQ ID NO. 20.

The adenoviral vector of the present invention may comprise one of the hexon, penton and fibre proteins as described above, any combination of two of said proteins, or all three of said proteins.

The adenoviral vector of the invention is referred to herein as ChAdOx2. The nucleotide sequence of the ChAdOx2 vector (with a Gateway™ cassette in the E1 locus) is shown in SEQ ID NO. 10.

The person skilled in the art will appreciate that there are homologues, equivalents and derivatives of all of the nucleic acid sequences described herein. Thus, the invention also encompasses nucleic acid molecules having a sequence substantially identical to the nucleic acid sequences described herein over their entire length.

One of skill in the art will appreciate that the present invention can also include variants of those particular nucleic acid molecules which are exemplified herein. These may occur in nature, for example because of strain variation. For example, additions, substitutions and/or deletions are included. One of skill in the art will also appreciate that variation from the particular nucleic acid molecules exemplified herein will be possible in view of the degeneracy of the genetic code. Preferably, the variants have substantial identity to the nucleic acid sequences described herein over their entire length.

As used herein, nucleic acid sequences which have "substantial identity" preferably have at least 80%, 90%, 91%, 92%, 93%, 94%, 95% 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4% 99.5%, 99.6%, 99.7%, 99.8% or 99.9% identity with said sequences. Desirably, the term "substantial identity" indicates that said sequence has a greater degree of identity with any of the sequences described herein than with prior art nucleic acid sequences.

When comparing nucleic acid sequences for the purposes of determining the degree of homology or identity one can use programs such as BESTFIT and GAP (both from the Wisconsin Genetics Computer Group (GCG) software package). BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention, when discussing identity of nucleic acid sequences, the comparison is made by alignment of the sequences along their whole length. The above applied mutatis mutandis to all nucleic acid sequences disclosed in the present application.

References herein to "nucleic acid" can be DNA, including cDNA, RNA including mRNA or PNA (peptide nucleic acid) or a mixture thereof.

Merely for the convenience of those of skill in the art, a sample of *E. coli* strain Stellar containing bacterial artificial chromosomes (BACs) containing the ChAdOx2-GFP was deposited by Isis Innovation Limited on 13 Jun. 2016 with the European Collection of Cell Cultures (ECACC) at the Health Protection Agency Culture Collections, Health Protection Agency, Porton Down, Salisbury SP4 OJG, United Kingdom under the Budapest Treaty and designated by provisional accession no. 16061301.

The *E. coli* containing the BAC is a class I genetically modified organism. The genotype of *E. coli* strain Stellar is:

F-, endA1, supE44, thi-1, recA1, relA1, gyrA96, phoA, φ80d lacZΔ M15, Δ (lacZYA-argF) U169, Δ (mrr-hsdRMS-mcrBC), ΔmcrA, λ-. Chimpanzee adenovirus ChAd68 is provisionally classified within the species Human adenovirus E based on the nucleotide sequence of the viral DNA polymerase.

The BAC propagates within the bacteria during replication and can be maintained by selection with chloramphenicol. The *E. coli* strain Stellar containing the BAC into which the genome is cloned can be propagated in Luria-Bertani broth or agar containing 12.5 µg/mL chloramphenicol at 37° C.

Converting the BAC clones of the viral genomes into viruses ("rescue") can be carried out by the following steps. The *E. coli* host is propagated and the BAC DNA is purified from the bacteria according to standard methods. The DNA is linearised with the restriction endonuclease PacI and transfected into HEK293 cells (or a similar E1 complementing cell line). The resulting adenovirus can then be propagated and purified for use as a vaccine for example. All of these reagents and cells are publicly available. If the deposition were rescued, the resulting virus would be a class I genetically modified organism.

As used herein, the phrase "viral vector" refers to a recombinant virus or a derivative thereof which is capable of introducing genetic material, including recombinant DNA, into a host cell or host organism by means of transduction or non-productive infection.

For example, the vector of the present invention may be a gene delivery vector, a vaccine vector, an antisense delivery vector or a gene therapy vector.

As used herein, "C68" refers to the chimpanzee adenovirus 68 or subunits derived therefrom, and the term "ChAd68" refers to vectors derived therefrom or based thereon.

Shorthand terms are used to indicate modifications made to the wildtype virus. For example, "ΔE1" or "delE1" indicates deletion or functional deletion of the E1 locus. The phrase "Ad5E4Orf6" indicates that the viral vector comprises heterologous E4 open reading frame 6 from the Ad5 virus.

One of skill in the art will appreciate that the present invention can include variants of those particular amino acid sequences which are exemplified herein. Particularly preferred are variants having an amino acid sequence similar to that of the parent protein, in which one or more amino acid residues are substituted, deleted or added in any combination. Especially preferred are silent substitutions, additions and deletions, which do not alter the properties and activities of the protein of the present invention. Various amino acids have similar properties, and one or more such amino acids of a substance can often be substituted by one or more other such amino acids without eliminating a desired activity of that substance. Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Variants include naturally occurring and artificial variants. Artificial variants may be generated using mutagenesis techniques, including those applied to nucleic acid molecules, cells or organisms. Preferably, the variants have substantial identity to the amino acid sequences exemplified herein.

As used herein, amino acid sequences which have "substantial identity" preferably have at least 80%, 90%, 91%, 92%, 93%, 94%, 95% 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8% or 99.9% identity with said sequences. Desirably, the term "substantial identity" indicates that said sequence has a greater degree of identity with any of the sequences described herein than with prior art amino acid sequences.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. The above applied mutatis mutandis to all amino acid sequences disclosed in the present application.

The vector of the present invention also preferably comprises an exogenous nucleotide sequence. Preferably, the exogeneous nucleotide sequence is operably linked to expression control sequences which direct the translation, transcription and/or expression thereof in an animal cell and an adenoviral packaging signal sequence.

Preferably, the exogeneous nucleotide sequence encodes a molecule of interest. The molecule of interest may be a protein, polypeptide or nucleic acid molecule of interest. The exogeneous nucleotide sequence may encode one or more, two or more or three or more molecules of interest.

Proteins and polypeptides of interest include antigens, molecular adjuvants, immunostimulatory proteins and recombinases.

Preferably the antigen is a pathogen-derived antigen. Preferably the pathogen is selected from the group consisting of *M. tuberculosis, Plasmodium* sp, influenza virus, HIV, Hepatitis C virus, Cytomegalovirus, Human papilloma virus, rabies virus, measles virus, mumps, rubella, zika virus, *leishmania* parasites or any mycobacterial species. Preferably the antigen is selected from TRAP, MSP-1, AMA-1 and CSP from *Plasmodium*, influenza virus antigens, or ESAT6, TB10.4 85A and 85B antigens from *Mycobacterium tuberculosis*. More preferably, the antigen may be Ag85A from *Mycobacterium tuberculosis*. The antigen may be nucleoprotein (NP) and/or matrix protein 1 (M1) from influenza A virus.

More preferably the antigen is from *Mycobacterium avium* subspecies paratuberculosis (MAP) or the antigen is rabies virus glycoprotein.

Preferably, the protein or polypeptide of interest is an antigen. In one embodiment, the antigen is a pathogen-derived antigen. Preferably, the pathogen is selected from the group consisting of bacteria, viruses, prions, fungi, protists and helminths. Preferably, the antigen is derived from the group consisting of *M. tuberculosis, Plasmodium* sp, influenza virus, HIV, Hepatitis C virus, Cytomegalovirus, Human papilloma virus, rabies virus, measles virus, mumps, rubella, zika virus, malaria parasites, *leishmania* parasites or any mycobacterial species. Preferred antigens include TRAP, MSP-1, AMA-1 and CSP from *Plasmodium*, influenza virus antigens and ESAT6, TB10.4 85A and 85B antigens from *Mycobacterium tuberculosis*. Particularly preferred antigens include Ag85A from *Mycobacterium tuberculosis* and nucleoprotein (NP) and matrix protein 1 (M1) from influenza A virus, preferably Influenza A virus.

The nucleic acid sequence of *Mycobacterium tuberculosis* protein Ag85A is shown in SEQ ID NO. 11 and the amino acid sequence is shown in SEQ ID NO. 12. The nucleic acid sequence of nucleoprotein (NP) and matrix protein 1 (Ml) from influenza A virus is shown in SEQ ID NO. 13 and the amino acid sequence is shown in SEQ ID NO. 14.

In a preferred embodiment, the vaccine contains antigens from *Mycobacterium avium* subspecies paratuberculosis (MAP) which is the causative agent for Johne's disease in cattle and has been linked to Crohn's disease in humans.

In another preferred embodiment, the exogeneous nucleotide sequence encodes the rabies virus glycoprotein, preferably the ERA strain.

In an alternative embodiment, the antigen is a self-antigen. Suitable self-antigens include antigens expressed by tumour cells which allow the immune system to differentiate between tumour cells and other cell types. Suitable self-antigens include antigens that are either inappropriate for the cell type and/or its environment, or are only normally present during the organisms' development (e.g. foetal antigens). For example, GD2 is normally only expressed at a significant level on the outer surface membranes of neuronal cells, where its exposure to the immune system is limited by the blood-brain barrier. However, GD2 is expressed on the surfaces of a wide range of tumour cells including small-cell lung cancer, neuroblastoma, melanomas and osteosarcomas. Other suitable self-antigens include cell-surface receptors that are found on tumour cells but are rare or absent on the surface of healthy cells. Such receptors may be responsible for activating cellular signalling pathways that result in the unregulated growth and division of the tumour cell. For example, ErbB2 is produced at abnormally high levels on the surface of breast cancer tumour cells. Preferably, the self antigen comprises a tumour-associated antigen (TAA).

As used herein, the term 'antigen' encompasses one or more epitopes from an antigen and includes the parent antigen, and fragments and variants thereof. These fragments and variants retain essentially the same biological activity or function as the parent antigen. Preferably, they retain or improve upon the antigenicity and/or immunogenicity of the parent antigen. Generally, "antigenic" is taken to mean that the protein or polypeptide is capable of being used to raise antibodies or T cells or indeed is capable of inducing an antibody or T cell response in a subject. "Immunogenic" is taken to mean that the protein or polypeptide is capable of eliciting a potent and preferably a protective immune response in a subject. Thus, in the latter case, the protein or polypeptide may be capable of generating an antibody response and a non-antibody based immune response.

Preferably, fragments of the antigens comprise at least n consecutive amino acids from the sequence of the parent antigen, wherein n is preferably at least, or more than, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 57, 58, 59, 60, 70, 80, 90 or 100. The fragments preferably include one or more epitopic regions from the parent antigen. Indeed, the fragment may comprise or consist of an epitope from the parent antigen. Alternatively, the fragment may be sufficiently similar to such regions to retain their antigenic/immunogenic properties.

The antigens of the present invention include variants such as derivatives, analogues, homologues or functional equivalents of the parent antigen. Particularly preferred are derivatives, analogues, homologues or functional equivalents having an amino acid sequence similar to that of the parent antigen, in which one or more amino acid residues are substituted, deleted or added in any combination. Preferably, these variants retain an antigenic determinant or epitope in common with the parent antigen.

Preferably, the derivatives, analogues, homologues, and functional equivalents have an amino acid sequence substantially identical to amino acid sequence of the parent antigen.

The exogeneous nucleotide sequence may encode more than one antigen. The viral vector may be designed to express the one or more antigen genes as an epitope string. Preferably, the epitopes in a string of multiple epitopes are linked together without intervening sequences such that unnecessary nucleic acid and/or amino acid material is avoided. The creation of the epitope string is preferably achieved using a recombinant DNA construct that encodes the amino acid sequence of the epitope string, with the DNA encoding the one or more epitopes in the same reading frame. An exemplary antigen, TIPeGFP, comprises an epitope string which includes the following epitopes: E6FP, SIV-gag, PyCD4 and Py3. Alternatively, the antigens may be expressed as separate polypeptides.

One or more of the antigens or antigen genes may be truncated at the C-terminus and/or the N-terminus. This may facilitate cloning and construction of the vectored vaccine and/or enhance the immunogenicity or antigenicity of the antigen. Methods for truncation will be known to those of skill in the art. For example, various well-known techniques of genetic engineering can be used to selectively delete the encoding nucleic acid sequence at either end of the antigen gene, and then insert the desired coding sequence into the viral vector. For example, truncations of the candidate protein are created using 3' and/or 5' exonuclease strategies selectively to erode the 3' and/or 5' ends of the encoding nucleic acid, respectively. Preferably, the wild type gene sequence is truncated such that the expressed antigen is truncated by 1, 2, 3, 4, 5, 6, 7, 8, 9, 10, 11, 12, 13, 14, 15, 16, 17, 18, 19, 20 or more amino acids relative to the parent antigen. Preferably, the antigen gene is truncated by 10-20 amino acids at the C-terminus relative to the wild type antigen. More preferably, the antigen gene is truncated by 13-18 amino acids, most preferably by 15 amino acids at the C-terminus relative to the wild type antigen. Preferably, the Ag85A antigen is C-terminally truncated in this manner.

One or more of the antigen genes may also comprise a leader sequence. The leader sequence may affect processing of the primary transcript to mRNA, translation efficiency, mRNA stability, and may enhance expression and/or immunogenicity of the antigen. Preferably, the leader sequence is tissue plasminogen activator (tPA). Preferably, the tPA leader sequence is positioned N-terminal to the one or more antigens.

The leader sequence such as the tPA leaders sequence may be linked to the sequence of the antigen via a peptide linker. Peptide linkers are generally from 2 to about 50 amino acids in length, and can have any sequence, provided that it does not form a secondary structure that would interfere with domain folding of the fusion protein.

One or more of the antigen genes may comprise a marker such as the Green Fluorescent Protein (GFP) marker to facilitate detection of the expressed product of the inserted gene sequence.

One or more of the antigen genes may comprise a nucleic acid sequence encoding a tag polypeptide that is covalently linked to the antigen upon translation. Preferably the tag polypeptide is selected from the group consisting of a PK tag, a FLAG tag, a MYC tag, a polyhistidine tag or any tag that can be detected by a monoclonal antibody. The nucleic acid sequence encoding the tag polypeptide may be positioned such that, following translation, the tag is located at the C-terminus or the N-terminus of the expressed antigen or may be internal to the expressed antigen. Preferably, the tag is located at the C-terminus of the expressed antigen. In a preferred embodiment, one or more of the antigen genes encode a PK tag. A tag of this type may facilitate detection of antigen expression and clones expressing the antigen, and/or enhance the immunogenicity or antigenicity of the antigen.

If a tag polypeptide is used, nucleotides encoding a linker sequence are preferably inserted between the nucleic acid encoding the tag polypeptide and the nucleic acid encoding the expressed antigen. An exemplary linker is IPNPLLGLD (SEQ ID NO.15).

In an alternative embodiment, the exogenous sequence of interest may be non-protein encoding. For example, the exogeneous nucleotide sequence may be an miRNA or immunostimulatory RNA sequence.

The adenoviral vector may comprise one or more exogeneous nucleotide sequences, for example 1, 2 or 3 or more exogenous nucleotide sequences. Preferably, each exogeneous nucleotide sequence embodies a transgene. The exogeneous nucleotide sequence embodying the transgene can be a gene or a functional part of the gene.

The adenoviral vector may comprise one nucleotide sequence encoding a single molecule of interest. Alternatively, the adenoviral vector may comprise one nucleotide sequence or more than one nucleotide sequence encoding more than one molecule of interest.

Preferably, the exogeneous nucleotide sequence is located within the genome of the adenovirus, i.e. in a nucleic acid molecule that contains other adenoviral sequences.

The exogeneous nucleotide sequence may be inserted into the site of a partially or fully deleted gene, for example into the site of an E1 deletion or an E3 deletion within the adenovirus genome.

The exogeneous nucleotide sequence may be inserted into an existing C68 gene region to disrupt the function of that region. Alternatively, the exogeneous nucleotide sequence may be inserted into a region of the genome with no alteration to the function or sequence of the surrounding genes.

The exogeneous nucleotide sequence or transgene is preferably operably linked to regulatory sequences necessary to drive translation, transcription and/or expression of the exogeneous nucleotide sequence/transgene in a host cell, for example a mammalian cell. As used herein, the phrase "operably linked" means that the regulatory sequences are contiguous with the nucleic acid sequences they regulate or that said regulatory sequences act in trans, or at a distance, to control the regulated nucleic acid sequence. Such regulatory sequences include appropriate expression control sequences such as transcription initiation, termination, enhancer and promoter sequences, efficient RNA processing signals, such as splicing and polyadenylation signals, sequences that enhance translation efficiency and protein stability and sequences promote protein secretion. Additionally they may contain sequences for repression of transgene expression, for example during production in cell lines expression a trans-activating receptor. Promoters and other regulatory sequences which control expression of a nucleic acid have been identified and are known in the art. Preferably, the promoter is selected from the group consisting of human CMV promoters, simian CMV promoters, murine CMV promoters, ubiquitin, the EF1 promoter, frog EF1 promoter, actin and other mammalian promoters. Most preferred are human CMV promoters and in particular the human CMV major immediate early promoter.

The exogeneous nucleotide sequence(s) of interest may be introduced into the viral vector as part of a cassette. As used herein, the term "cassette" refers to a nucleic acid molecule comprising at least one nucleotide sequence to be expressed, along with its transcriptional and translational control sequences to allow the expression of the nucleotide sequence(s) in a host cell, and optionally restriction sites at the 5' and 3' ends of the cassette. Because of the restriction endonuclease sites, the cassettes can easily be inserted, removed or replaced with another cassette. Changing the cassette will result in the expression of different sequence(s) by the vector into which the cassette is incorporated. Alternatively, any method known to one of skill in the art could be used to construct, modify or derive said cassette, for example PCR mutagenesis, In-Fusion®, recombineering, Gateway® cloning, site-specific recombination or topoisomerase cloning.

The expression control sequences preferably include the adenovirus elements necessary for replication and virion encapsidation. Preferably, the elements flank the exogeneous nucleotide sequence. Preferably, the ChAd68 vector comprises the 5' inverted terminal repeat (ITR) sequences of C68, which function as origins of replication, and 3' ITR sequences.

The packaging signal sequence functions to direct the assembly of the viral vector, and are well characterised and understood in the art.

As one of skill in the art will appreciate, there are minimum and maximum constraints upon the length of the nucleic acid molecule that can be encapsidated in the viral vector. Therefore, if required, the nucleic acid molecule may also comprise "stuffing", i.e. extra nucleotide sequence to bring the final vector genome up to the required size.

Preferably, the nucleic acid molecule comprises sufficient "stuffing" to ensure that the nucleic acid molecule is about 80% to about 108% of the length of the wild-type nucleic acid molecule.

The nucleic acid molecule may also comprise one or more genes or loci from the C68 genome. The wild-type C68 genome comprises 4 early transcriptional units (E1, E2, E3 and E4), which have mainly regulatory functions and prepare the host cell for viral replication. The genome also comprises 5 late transcriptional units (L1, L2, L3, L4 and L5), which encode structural proteins including the penton (L2), the hexon (L3), the scaffolding protein (L4) and the fiber protein (L5), which are under the control of a single promoter. Each extremity of the genome comprises an Inverted Terminal Repeat (ITR) which is necessary for viral replication.

The viral vector of the present invention may be based on the complete native C68 genome, from which the native E4 region has been deleted and into which the heterologous E4Orf1, E4Orf2 and E4Orf3 coding regions from AdY25 have been inserted.

The native E4 region of C68 is provided herein as SEQ ID NO. 2.

An exogeneous nucleotide sequence of interest may also be inserted into the C68 genome. One of skill in the art will appreciate that various additional modifications to the native C68 genome are possible, and indeed desirable, when creating a viral vector.

One or more native C68 genes may be deleted, functionally deleted or modified to optimise the viral vector.

As used herein, the phrase "deleted" refers to total deletion of a gene, whilst "functional deletion" refers to a partial deletion of a gene/locus, or some other modification such as a frame shift mutation, which destroys the ability of the adenovirus to express the gene/locus or renders the gene product non-functional.

The C68 genome may be modified to increase the insert capacity or hinder replication in host cells and/or increase growth and yield of the viral vector in transformed packaging cell lines. One of skill in the art will appreciate that any number of early or late genes can be functionally deleted. Replication of such modified viral vectors will still be possible in transformed cell lines which comprise a complement of the deleted genes. For example, the viral proteins necessary for replication and assembly can be provided in trans by engineered packaging cell lines or by a helper virus.

Therefore, in addition to the exogeneous nucleotide sequence, the vector of the present invention may comprise the minimal adenoviral sequences, the adenoviral genome with one or more deletions or functional deletions of particular genes, or the complete native adenoviral genome, into which has been inserted the exogeneous nucleotide sequence.

Preferably, one or more of the early transcriptional units are modified, deleted or functionally deleted.

In one embodiment, the viral vector is non-replicating or replication-impaired. As used herein, the term "non-replicating" or "replication-impaired" means not capable of replicating to any significant extent in the majority of normal mammalian cells, preferably normal human cells. It is preferred that the viral vector is incapable of causing a productive infection or disease in the human patient. However, the viral vector is preferably capable of stimulating an immune response. Viruses which are non-replicating or replication-impaired may have become so naturally, i.e. they may be isolated as such from nature. Alternatively, the viruses may be rendered non-replicating or replication-impaired artificially, e.g. by breeding in vitro or by genetic manipulation. For example, a gene which is critical for replication may be functionally deleted.

Preferably, the adenoviral vector replication is rendered incompetent by functional deletion of a single transcriptional unit which is essential for viral replication. Preferably, the E1 gene/locus is deleted or functionally deleted. The E1 gene/locus may be replaced with a heterologous transgene, for example a nucleotide sequence or expression cassette encoding a protein or polypeptide of interest.

The native E1 region of C68 is provided herein as SEQ ID NO. 16.

As discussed herein, the recombinant adenovirus may be created by generating a molecular clone of C68 in a Bacterial Artificial Chromosome (BAC), and the E1 locus is preferably deleted by including an extra homology flank downstream of the adenovirus E1 region to enable simultaneous deletion of E1 during homologous recombination between the C68 viral DNA and a linearised BAC "rescue vector".

Preferably, the viral vector according to the present invention comprises one or more recombination sites to enable the insertion of one or more transgenes or cassettes comprising the exogeneous nucleotide sequence. Preferably, the recombination sites comprise phage lambda site specific recombination sites. These recombination sites may be introduced at any suitable locus, but are preferably introduced at the adenovirusE1 locus. Thus, the non-replicating or replication-impaired vector may be prepared by replacing the E1 gene with a nucleotide sequence encoding the protein or polypeptide of interest. Preferably, the recombination sites attR1 and attR2 are introduced at the adenovirusE1 locus as part of an Invitrogen Gateway® destination cassette.

Preferably, the vector lacks an adenovirus E3 gene/locus. Deletion of the adenovirus E3 region increases the insert capacity of the new vector by approximately 5 kb. Deletion of E3 has little consequence to viral vector yield since this region is not required for virus replication and therefore does not need to be provided in trans in the packaging cell line. The E3 locus may be deleted using GalK recombineering.

The native E3 region of C68 is provided herein as SEQ ID NO. 17.

In a particularly preferred embodiment of the present invention, both the E1 and E3 loci are deleted from the C68 genome.

The viral vectors of the present invention may be produced in engineered cell lines containing a complement of any deleted genes required for viral replication. However, replication of viral vectors according to the present invention may be sub-optimal in cells designed to facilitate replication of other serotypes. Therefore, the adenoviral vectors according to the present invention preferably further comprise one or more modifications designed to optimise vector growth and yield in transformed cell lines, such as HEK293, expressing the genes functionally deleted in the adenoviral vector according to the present invention.

Of particular importance for viral replication in HEK293 cells is the gene product of E4Orf6, a multifunctional protein implicated in late viral mRNA splicing and selective export of viral mRNA, viral DNA synthesis and inhibition of apoptosis. Suboptimal interaction between E4Orf6 and the cell-expressed E1B-55K is believed to reduce the yield of ChAdOx2 vectors in HEK293 cells. Therefore, the native E4Orf6 region may be replaced with a heterologous E4Orf6 region.

In a preferred embodiment, the native E4Orf4, E4Orf6 and E4Orf6/7 coding regions are replaced with the E4Orf4, E4Orf6 and E4Orf6/7 coding regions from AdHu5. In a particularly preferred embodiment, the recombinant E4 region comprises the E4Orf1, E4Orf2 and E4Orf3 coding regions from AdY25 and the E4Orf4, E4Orf6 and E4Orf6/7 coding regions from AdHu5.

The amino acid sequence of E4Orf4 from AdHu5 is found in SEQ ID NO. 7. A corresponding nucleotide sequence is found at nucleotides 29262 to 28918 of the ChAdOx2 vector sequence (SEQ ID NO. 10). The amino acid sequence of the E4Orf6 from AdHu5 is found in SEQ ID NO. 8. A corresponding nucleotide sequence is found at nucleotides 28997 to 28113 of SEQ ID NO. 10. The amino acid sequence of the E4Orf6/7 from AdHu5 is found in SEQ ID NO. 9. A corresponding nucleotide sequence is found at nucleotides 28997 to 27834 of SEQ ID NO. 10.

In one preferred embodiment, the vector of the present invention comprises the nucleotide sequences of AdHu5 E4Orf4, E4Orf6 and E4Orf6/7 or sequences substantially identical thereto.

The amino acid sequence of E4Orf1 from AdY25 is provided herein as SEQ ID NO. 3. A corresponding nucleotide sequence is found at nucleotides 30434 to 30060 of the ChAdOx2 vector sequence (SEQ ID NO. 10).

The amino acid sequence of E4Orf2 from AdY25 is provided herein as SEQ ID NO. 4. A corresponding nucleotide sequence is found at nucleotides 30010 to 29621 of SEQ ID NO. 10.

The amino acid sequence of E4Orf3 from AdY25 is provided herein as SEQ ID NO. 5. A corresponding nucleotide sequence is found at nucleotides 29624 to 29271 of SEQ ID NO. 10.

In a particularly preferred embodiment of the present invention, the viral vector comprises a modified form of the native C68 genome, wherein the native C68 nucleotide sequence lacks the nucleotide sequences which encode the adenovirus E1 and E3 regions, and has the native E4 locus replaced with E4Orf4, E4Orf6 and E4Orf6/7 coding regions from AdHu5, and the E4Orf1, E4Orf2 and E4Orf3 coding regions from AdY25. This particularly preferred viral vector according to the invention is referred to herein as "ChAdOx2".

An exemplary nucleotide sequence encoding ChAdOx2, with a Gateway® Destination Cassette in the E1 locus) is set out in SEQ ID NO. 10.

Preferably, the genome of the viral vector according to the present invention comprises the nucleotide sequence of SEQ ID NO.10 or a sequence substantially identical thereto, into which is inserted the exogeneous nucleotide sequence encoding the protein of interest.

A second aspect of the present invention provides a pharmaceutical or immunogenic composition comprising the viral vector according to the second aspect of the present invention optionally in combination with one or more additional active ingredients, a pharmaceutically acceptable carrier, diluent, excipient or adjuvant.

Preferably, the composition is an immunogenic and/or antigenic composition. The immunogenic and/or antigenic compositions according to the present invention may be prophylactic (to prevent infection), post-exposure (to treat after infection but before disease) or therapeutic (to treat disease). Preferably, the composition is prophylactic or post-exposure. Preferably, the composition is a vaccine.

Where the immunogenic composition is for prophylactic use, the subject is preferably an infant, young child, older child or teenager. Where the immunogenic composition is for therapeutic use, the subject is preferably an adult.

The composition may comprise one or more additional active agents, such as an anti-inflammatory agent (for example a p38 inhibitor, glutamate receptor antagonist, or a calcium channel antagonist), AMPA receptor antagonist, a chemotherapeutic agent and/or an antiproliferative agent. The composition may also comprise one or more antimicrobial compounds. Examples of suitable antimicrobial compounds include antituberculous chemotherapeutics such as rifampicin, isoniazid, ethambutol and pyrizinamide.

Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

Suitable adjuvants are well known in the art and include incomplete Freund's adjuvant, complete Freund's adjuvant, Freund's adjuvant with MDP (muramyldipeptide), alum (aluminium hydroxide), alum plus Bordatella pertussis and immune stimulatory complexes (ISCOMs, typically a matrix of Quil A containing viral proteins).

The composition according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatine capsule; alternatively, a dispersion or suspension can be prepared using any suitable pharmaceutical carrier(s), for example aqueous gums, celluloses, silicates or oils and the dispersion or suspension then filled into a soft gelatine capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, *arachis* oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve, which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

The pharmaceutical composition is preferably sterile. It is preferably pyrogen-free. It is preferably buffered e.g. at between pH 6 and pH 8, generally around pH 7. Preferably, the composition is substantially isotonic with humans.

Preferably, the pharmaceutical compositions of the present invention deliver an immunogenically or pharmaceutically effective amount of the viral vector to a patient. As used herein 'immunogenically or pharmaceutically effective amount' means that the administration of that amount to an individual, either as a single dose or as a series of doses, is effective for prevention or treatment of a disease or condition. In particular, this phrase means that a sufficient amount of the viral vector is delivered to the patient over a suitable timeframe such that a sufficient amount of the antigen is produced by the patient's cells to stimulate an immune response which is effective for prevention or treatment of a disease or condition. This amount varies depending on the health and physical condition of the individual to be treated, age, the capacity of the individual's immune system, the degree of protection desired, the formulation of the vaccine, the doctor's assessment of the medical situation and other relevant factors.

In general, a pharmaceutically effective dose comprises $1\times10^7$ to $1\times10^{12}$ viral particles (vp), preferably $1\times10^{10}$ to $1\times10^{11}$ particles. More preferably, a pharmaceutically effective dose comprises $2.5\times10^{10}$ v.p. to $5\times10^{10}$ vp. Most preferably, a pharmaceutically effective dose comprises $2.5\times10^{10}$ v.p.

In a preferred embodiment, there is provided a vaccine based on ChAdOx2, wherein the vaccine contains antigens from *Mycobacterium avium* subspecies paratuberculosis (MAP). Preferably, this vaccine is administered at a dose of between $5\times10^9$ and $5\times10^{10}$ vp. More preferably, this vaccine is administered at a dose of between $2.5\times10^{10}$ v.p. and $5\times10^{10}$ vp. Most preferably, the vaccine is administered at a dose of $2.5\times10^{10}$ v.p.

In a preferred embodiment, there is provided a vaccine based on ChAdOx2, wherein the ChAdOx2 vector encodes the rabies virus glycoprotein. In a preferred embodiment, this vaccine is administered to animals at a dose of between $1\times10^6$ and $1\times10^8$ infectivity units. In another preferred embodiment, this vaccine is administered to humans at a dose of between $5\times10^9$ and $5\times10^{10}$ vp. More preferably, this vaccine is administered in humans at a dose of between $2.5\times10^{10}$ v.p. and $5\times10^{10}$ vp. Most preferably, the vaccine is administered in humans at a dose of $2.5\times10^{10}$ v.p.

The immunogenic composition of the present invention may also comprise one or more other viral vectors, preferably other adenoviral vectors.

A third aspect of the present invention provides the use of the viral vector according to the first aspect of the present invention or the immunogenic composition according to the second aspect of the present invention. In particular, the third aspect provides the use of the viral vector or the immunogenic composition of the present invention in medicine.

This aspect also provides: i) the viral vector or the immunogenic composition according to the present invention for use in medicine and ii) the use of the viral vector or the immunogenic composition according to the present invention in the manufacture of a medicament for use in medicine. Some exemplary medical uses are described in further detail below.

In one embodiment, the viral vector according to the first aspect of the present invention or the immunogenic composition according to the second aspect of the present invention may be used to deliver a transgene into a host cell.

This method preferably comprises the step of administering to said host cell a viral vector according to the second aspect of the present invention or the immunogenic composition according to the third aspect of the present invention.

Preferably, the host cell is an animal cell, more preferably a mammalian cell. Preferred mammals include chickens, other poultry, cows, sheep, goats, pigs, wild boar, buffalo, bison, horses, camelids, deer, elephants, badgers, possums, cats, lions, monkeys and humans. Preferably, the host cell is a somatic cell. The host cell may be selected from the group consisting of an antigen-presenting dendritic cell, langerhans cell, macrophage, B cell, lymphocyte, leukocyte, myocyte and fibroblast.

This method may be carried out in vitro or in vivo. Where the method is carried out in vitro, the viral vector or immunogenic composition is brought into contact with the host cell under suitable conditions such that transduction or non-productive infection of the host cell with the viral vector is facilitated. In this embodiment, the host cell may comprise an isolated host cell or a sample from an animal subject. Where the method is carried out in vivo, the viral vector or immunogenic composition is preferably administered to the animal subject such that transduction of one or more cells of the subject with the viral vector is facilitated. Preferably, the viral vector or immunogenic composition is administered to the subject by oral (including by inhalation), parenteral (e.g. intramuscular, subcutaneous, intravenous or intraperitoneal), mucosal (e.g. buccal, sublingual, nasal), rectal or transdermal administration.

Preferably, the transduction of the host cell with the viral vector of the present invention results in the stable delivery of the exogeneous nucleotide sequence of interest into the host cell.

Therefore, in another embodiment, the viral vector according to the first aspect of the present invention or the immunogenic composition according to the second aspect of the present invention may be used to elicit an immune response in an animal. This method preferably comprises the step of administering to said animal a viral vector according to the first aspect of the present invention or the immunogenic composition according to the second aspect of the present invention.

Where the protein or polypeptide of interest is an antigen, expression of the protein or polypeptide in an animal will result in the elicitation of a primary immune response to that antigen, leading to the development of an immunological memory which will provide an enhanced response in the event of a secondary encounter, for example upon infection by the pathogen from which the antigen was derived.

Preferably, the animal is a naïve animal, i.e. an animal that has not previously been exposed to the pathogen or antigens in question.

As well as eliciting an immune response in an animal, the viral vector of the present invention or the immunogenic composition thereof can be used to boost the immune response of an animal previously exposed to the antigen.

Therefore, in a further embodiment, the viral vector according to the first aspect of the present invention or the immunogenic composition according to the second aspect of the present invention may be used to boost an immune response in an animal. This method preferably comprises the step of administering to said animal a viral vector according to the second aspect of the present invention or the immunogenic composition according to the third aspect of the present invention.

Preferably, the animal subject has been previously exposed to the antigen in question, or "primed". For example, the subject may have previously been inoculated or vaccinated with a composition comprising the antigen, or may have previously been infected with the pathogen from which the antigen was derived. The subject may be latently infected with the pathogen from which the antigen was derived.

In another embodiment, the vector according to the first aspect of the present invention or the immunogenic composition according to the second aspect of the present invention may be used to treat or prevent at least one disease in a patient. A method of treating or preventing a disease in a patient according to the invention preferably comprises the step of administering to said patient a viral vector according to the first aspect of the present invention or the immunogenic composition according to the second aspect of the present invention.

Preferably, the disease is selected from the group consisting of Tuberculosis and other mycobacterial infections including Johne's disease, Crohn's disease, malaria, influenza, HIV/AIDS, Hepatitis C, Cytomegalovirus infection, Human papilloma virus infection, adenoviral infection, Ieishmaniasis, *streptococcus* spp., *staphylococcus* spp., *meningococcus* spp., infection, foot and mouth disease, chikungunya virus infection, Zika virus, rabies, Crimean Congo haemorrhagic fever, Ebola virus disease, Marburg, Lassa fever, MERS and SARS coronavirus diseases, Nipah and Rift Valley fever, Zika, Chikungunya.

Most preferably, the disease is selected from the group consisting of Tuberculosis and other mycobacterial infections, and rabies. As well as inducing an immune response against the pathogenic organism from which the heterologous antigen is derived, the adenoviral vector of the present invention may also induce an immune response against the adenovirus from which the viral vector is derived. As such, an immune response against C68 may be elicited. The immune response induced against C68 may also be cross-reactive with other adenoviral serotypes, and as such an immune response against more than one adenovirus may be elicited. The viral vector according to the second aspect of the present invention or the immunogenic composition according to the third aspect of the present invention can therefore also be used for treating or preventing an adenoviral disease.

This embodiment of the present invention therefore also provides the treatment or prevention of at least one adenoviral disease and at least one non-adenoviral disease in a patient.

In a further embodiment, the viral vector according to the first aspect of the present invention or the immunogenic composition according to the second aspect of the present invention may be used to induce an immune response in an animal that will break tolerance to a self antigen. This method preferably comprises the step of administering to said animal a viral vector according to the first aspect of the present invention or the immunogenic composition according to the second aspect of the present invention.

Many tumour cells are tolerated by the patient's immune system, on the grounds that tumour cells are essentially the patient's own cells that are growing, dividing and spreading without proper regulatory control. Thus, cancerous tumours are able to grow unchecked within the patient's body. However, the viral vector of the present invention can be used to stimulate a patient's immune system to attack the tumour cells in a process known as "cancer immunotherapy". Specifically, the vector of the present invention can be used to 'train' the patient's immune system to recognise tumour cells as targets to be destroyed. This can be achieved by including within the viral vector an exogeneous nucleotide sequence encoding a suitable self-antigen. As described previously, suitable self-antigens include antigens expressed by tumour cells which allow the immune system to differentiate between tumour cells and other cell types. Suitable self-antigens include antigens that are either inappropriate for the cell type and/or its environment, or are only normally present during the organisms' development (e.g. foetal antigens). For example, GD2 is normally only expressed at a significant level on the outer surface membranes of neuronal cells, where its exposure to the immune system is limited by the blood-brain barrier. However, GD2 is expressed on the surfaces of a wide range of tumour cells including small-cell lung cancer, neuroblastoma, melanomas and osteosarcomas. Other suitable self-antigens include cell-surface receptors that are found on tumour cells but are rare or absent on the surface of healthy cells. Such receptors may be responsible for activating cellular signalling pathways that result in the unregulated growth and division of the tumour cell. For example, ErbB2 is produced at abnormally high levels on the surface of breast cancer tumour cells. Thus, the adenoviral vector of the present invention may be used to induce an immune response against a tumour cell, and can therefore be used in the treatment of cancer.

The adenoviral vector of the invention can be used to treat, prevent or limit development of a tumour or cancer, including, but not limited to, cancer of the spleen, pancreas, prostate, liver, lung, breast, bowel, brain and colon.

A method of treating or preventing cancer in a patient comprises administering a therapeutically-effective dose of the adenoviral vector of the invention to a patient.

The adenoviral vector of the invention can also be used to treat autoimmune conditions, or conditions caused by hypersensitivity to own antigens.

A method of treating an autoimmune condition in a patient comprises administering a therapeutically-effective dose of the adenoviral vector of the invention to a patient.

The following details apply mutatis mutandis to all of the above uses of the vector and immunogenic composition of the present invention.

The treatment and prevention of many diseases, including liver stage malaria, tuberculosis and influenza, are associated with the maintenance of a strong cell-mediated response to infection involving both CD4+ and CD8+ T cells and the ability to respond with Th1-type cytokines, particularly IFN-γ, TNF-α, IL-2 and IL-17. Although many subunit vaccine platforms effectively generate human immunity, the generation of robust cell-mediated immune responses, particularly CD4+ and CD8+ T cell immune responses, has been much more challenging. The viral vector of the present invention preferably stimulates both cellular and humoral immune responses against the encoded antigen.

It is also desirable to induce a memory immune response. Memory immune responses are classically attributed to the reactivation of long-lived, antigen-specific T lymphocytes that arise directly from differentiated effector T cells and persist in a uniformly quiescent state. Memory T cells have been shown to be heterogeneous and to comprise at least two subsets, endowed with different migratory capacity and effector function; effector memory T cells (TEM) and central memory T cells (CTM). TEM resemble the effector cells generated in the primary response in that they lack the lymph node-homing receptors L-selectin and CCR7 and express receptors for migration into inflamed tissues. Upon re-encounter with antigen, these TEM can rapidly produce IFN-γ or IL-4 or release pre-stored perform. TCM express L-selectin and CCR7 and lack immediate effector function. These cells have a low activation threshold and, upon re-stimulation in secondary lymphoid organs, proliferate and differentiate to effectors.

Preferably, the viral vector according to the first aspect of the present invention or the immunogenic composition according to the second aspect of the present invention is capable of eliciting, inducing or boosting an antigen-specific immune response. Preferably, the immune response is a strong T cell immune response, for example a strong CD8+ and CD4+ T cell response. Preferably, the T cell immune response is a protective T cell immune response. Preferably, the T cell immune response is long lasting and persists for at least 1, 2, 5, 10, 15, 20, 25 or more years. Preferably, the immune response induced is a memory T cell immune response.

The viral vector of the first aspect of the present invention or immunogenic composition according to the second aspect of the present invention may be administered to the host cell or subject either as a single immunisation or multiple immunisations. Preferably, the viral vector or immunogenic composition thereof are administered as part of a single, double or triple vaccination strategy. They may also be administered as part of a homologous or heterologous prime-boost immunisation regime.

The vaccination strategy or immunisation regime may include second or subsequent administrations of the viral vector or immunogenic composition of the present invention. The second administration can be administered over a short time period or over a long time period. The doses may be administered over a period of hours, days, weeks, months or years, for example up to or at least 1, 2, 3, 4, 5, 6, 7, 8, 9, or 10 or more weeks or 0.25, 0.5, 0.75, 1, 5, 10, 15, 20, 25, 30, 35 or 40 or more years after the first administration. Preferably, the second administration occurs at least 2 months after the first administration. Preferably, the second administration occurs up to 10 years after the first administration. These time intervals preferably apply mutatis mutandis to the period between any subsequent doses.

The viral vector and/or immunogenic composition may be administered alone or in combination with other viral or non-viral DNA/protein vaccines. Preferred examples include modified vaccinia Ankara (MVA), Fowlpox 9 (FP9) and other adenoviral vector vaccines.

The viral vector and/or immunogenic composition may be administered to the subject by oral (including by inhalation), parenteral, mucosal (e.g. buccal, sublingual, nasal), rectal or transdermal administration. Alternatively, the viral vector and/or immunogenic composition may be administered to an isolated host cell or sample from a subject by contacting the cell(s) with the viral vector or immunogenic composition in vitro under conditions that facilitate the transduction of the host cell with the viral vector.

The viral vector and immunogenic composition of the present invention are not limited to the delivery of nucleic acid sequences encoding antigens. Many diseases, including cancer, are associated with one or more deleterious mutant alleles in a patient's genome. Gene therapy is a process involving the insertion of genes into the patient's cells or tissues to replace the deleterious mutant or non-functional allele(s) with 'normal' or functional allele(s). Commonly, a functional allele is inserted into a non-specific location within the genome to replace the non-functional allele. Alternatively, the non-functional allele may be swapped for the functional allele through homologous recombination. Subsequent expression of the functional allele within the target cell restores the target cell to a normal state and thus provides a treatment for the disease. The 'normal' or functional allele(s) may be inserted into a patient's genome using a viral vector. The present invention therefore also provides the use of the viral vector according to the first aspect of the present invention or the immunogenic composition according to the second aspect of the present invention in gene therapy.

This method preferably comprises the step of administering to said animal a viral vector according to the second aspect of the present invention or the immunogenic composition according to the third aspect of the present invention.

The vector of the present invention may comprise an exogeneous nucleotide sequence encoding the functional or 'normal' protein, the non-functional or 'mutant' version of which is associated with a disease or condition.

Preferably, the target cell is a somatic cell. The subject to be treated is preferably mammalian. Preferred mammals include chickens, other poultry, cows, sheep, goats, pigs, wild boar, buffalo, bison, horses, camelids, deer, elephants, badgers, possums, cats, lions, monkeys and humans.

A fourth aspect of the present invention provides a polynucleotide sequence encoding the viral vector according to the first aspect of the present invention.

Preferably, the polynucleotide sequence comprises the sequence of SEQ ID NO. 10, or a sequence substantially identical thereto. The polynucleotide may additionally comprise the exogeneous nucleotide sequence of interest.

A fifth aspect of the present invention provides a host cell transduced or infected with the viral vector according to the first aspect of the present invention. Following transduction or infection, the host cell will express the exogeneous nucleotide sequence in the nucleic acid molecule to produce the molecule of interest, in addition to any other adenoviral proteins encoded by the nucleic acid molecule. Preferably, the host cell is stably transduced and suitable for viral propagation.

The host cell may be an isolated host cell, part of a tissue sample from an organism, or part of a multicellular organism or organ or tissue thereof.

Preferably, the host cell is a somatic cell. Preferably, the host cell is not a stem cell, more particularly an embryonic stem cell, more particularly a human embryonic stem cell.

The host cell may be selected from the group consisting of an antigen-presenting dendritic cell, langerhans cell, macrophage, B cell, lymphocyte, leukocyte, myocyte and fibroblast.

Preferably, the host cell is an animal cell, more preferably a mammalian cell. Preferred mammals include chickens, other poultry, cows, sheep, goats, pigs, wild boar, buffalo, bison, horses, camelids, deer, elephants, badgers, possums, cats, lions, monkeys and humans.

The fifth aspect of the present invention also encompasses an animal transduced or infected with the viral vector according to the first aspect of the present invention. Preferably, the animal comprises one or more cells transformed or transfected with the viral vector according to the first aspect of the present invention. Preferably, the animal is a mammal. Preferred mammals include chickens, other poultry, cows, sheep, goats, pigs, wild boar, buffalo, bison, horses, camelids, deer, elephants, badgers, possums, cats, lions, monkeys and humans.

In a sixth aspect, the present invention provides a method of producing the viral vector according to the first aspect of the present invention. Preferably, the method comprises the step of incorporating the polynucleotide sequence according to the fourth aspect of the invention into a Bacterial Artificial Chromosome (BAC) to produce an Ad-BAC vector.

Unlike plasmid vectors, BACs are present within *E. coli* in single copy conferring increased genetic stability. In addition, the single copy BAC vectors permit very precise modifications to be made to the viral genome by recombineering (recombination mediated genetic engineering).

Preferably, incorporation of the polynucleotide sequence of the invention (preferably derived from C68) into a Bacterial Artificial Chromosome (BAC) comprises the steps of:
i) constructing a BAC rescue vector comprising regions of homology to the left and right flanks of the viral nucleotide sequence;
ii) linearising the BAC rescue vector; and
iii) performing homologous recombination in a host cell between the viral nucleotide sequence and the linearised BAC rescue vector to incorporate the viral nucleotide sequence into the BAC rescue vector.

Preferably, the polynucleotide sequence incorporated into the BAC rescue vector comprises the sequence of SEQ ID NO. 10 or a sequence substantially identical thereto.

Preferably, the method additionally comprises the step of further modifying the Ad-BAC vector genome. These further modifications may be carried out by GalK recombineering. This technique, pioneered by Søren Warming and colleagues, utilises the GalK gene for both positive and negative selection of recombinant clones[6]. SW102 *E. coli* cells, in which recombination may be performed, have been specifically engineered to lack the GalK gene which is required for the utilisation of galactose as the sole carbon source. Gene deletion is performed by recombination between the vector genome and a PCR amplified GalK cassette, flanked by 50 bp regions of homology either side of the gene targeted for deletion. Selection on minimal media containing only galactose should ensure that only recombinants containing the GalK gene (in place of the target gene) should grow. Replacement of GalK with a different gene sequence can be performed in a similar fashion, this time using GalK for negative selection. The addition of 2-deoxygalactose (DOG) to selection media will select clones in which GalK has been replaced since the product of GalK, galactokinase, metabolises DOG into a product that is highly toxic to *E. coli*. Preferably, the host cell is BJ5183 *E. coli* for steps i) to iii) above and SW102 for further modifications.

Preferably, an extra homology flank is included downstream of the adenovirus E1 region to enable simultaneous deletion of E1.

Preferably, the method further includes deletion of the E3 region of the Ad-BAC vector genome. Deletion of the E3 region may be carried out by GalK recombineering.

Preferably, the method further includes introducing phage lambda site specific recombination sites attR1 and attR2 at the Ad E1 locus as part of an Invitrogen Gateway® destination cassette. Such a modification enables the efficient directional insertion of vaccine transgenes. Transgenes could also be inserted by recombineering, In-Fusion®, conventional ligation or gap repair.

A seventh aspect of the present invention provides a Bacterial Artificial Chromosome (BAC) clone comprising a polynucleotide sequence encoding the viral vector according to the first aspect of the present invention.

Preferably, the BAC clone comprises:
(a) a BAC backbone,
(b) the polynucleotide sequence according to the fourth aspect of the present invention.

As described above, the viral vector according to the first aspect of the present invention may be replicated in a transformed cell line or helper virus (gutless vector system) which, if necessary, comprises the complement of any genes deleted from the virus. Such genes may be deleted from the virus in order to hinder replication in host cells, but are of course required in order to replicate the viral vector to produce immunogenic compositions according to the second aspect of the present invention. One can make use of any cell line permissive of wild type adenovirus replication that has been modified to express the functionally deleted genes, or a cell line which is not permissive of wild-type virus replication which has additionally or alternatively been modified to express CAR or integrins in addition to the functionally deleted genes.

The present invention provides host cells comprising a Bacterial Artificial Chromosome (BAC) in accordance with the seventh aspect of the present invention, and suitable for propagation thereof. Preferably such host cells are bacteria, most preferably *E. coli*. Suitable examples include *E. coli* strains DH10B and SW1029.

An eighth aspect of the present invention therefore provides a packaging cell or cell line producing or capable of producing the viral vector according to the first aspect of the present invention.

The packaging cell or cell line comprises one or more nucleotide sequences which encode the viral vector of the first aspect of the present invention. Expression of these sequences results in the production of the viral vector. Some of the required genes may be provided by infection of the cell or cell line with a viral vector according to the first aspect. Preferably, the cell comprises the complement of any genes deleted or functionally deleted from the viral vector. Preferably, the cell is an HEK293 cell or a PER.C6® cell.

Merely for the convenience of those of skill in the art, a sample of *E. coli* strain Stellar containing bacterial artificial chromosomes (BACs) containing the ChAdOx2-GFP was deposited by Isis Innovation Limited on 13 Jun. 2016 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 16061301.

In respect of all designated states to which such action is possible and to the extent that it is legally permissible under the law of the designated state, it is requested that a sample of the deposited material be made available only by the issue thereof to an independent expert, in accordance with the relevant patent legislation, e.g. Rule 32(1) EPC, Rule 13(1) and Schedule 1 of the UK Patent Rules 2007, Regulation 3.25(3) of the Australian Patent Regulations and generally similar provisions mutatis mutandis for any other designated state.

As described herein, the vector ChAdOx2 is derived from chimpanzee adenovirus C68, with deletion of E1 region, E3 region, modification of E4 region and insertion of eGFP model antigen into E1 locus. The *E. coli* containing the BAC is a class I genetically modified organism.

The BAC propagates within the bacteria during replication and can be maintained by selection with chloramphenicol. The *E. coli* strain SW102 containing the bacterial artificial chromosomes into which the genomes are cloned can be propagated in Luria-Bertani broth or agar containing 12.5 μg/mL chloramphenicol at 32° C. The genome may be modified by genetic engineering in *E. coli* according to standard methods, as described in the specification, e.g. to insert an alternative recombinant antigen in place of eGFP.

Converting the BAC clones of the viral genomes into viruses ("rescue") can be carried out by the following steps. The *E. coli* host is propagated and the BAC DNA is purified from the bacteria according to standard methods. The DNA is linearised with the restriction endonuclease PacI and transfected into HEK293 cells (or a similar E1 complementing cell line). The resulting adenovirus can then be propagated and purified for use as a vaccine, for example. All of these reagents and cells are publicly available. If the deposition were rescued, the resulting virus would be a class I genetically modified organism.

In respect of all designated states to which such action is possible and to the extent that it is legally permissible under the law of the designated state, it is requested that a sample of the deposited material be made available only by the issue thereof to an independent expert, in accordance with the relevant patent legislation, e.g. Rule 32(1) EPC, Rule 13(1) and Schedule 1 of the UK Patent Rules 2007, Regulation 3.25(3) of the Australian Patent Regulations and generally similar provisions mutatis mutandis for any other designated state.

A specific embodiment of the fourth aspect of the present invention provides a polynucleotide sequence encoding an adenoviral vector according to the first aspect of the present invention, wherein said polynucleotide sequence comprises or consists of the polynucleotide sequence of the viral vector ChAdOx2 (SEQ ID NO. 10).

ChAdOx2 was deposited in a BAC contained in *E. coli* strain Stellar by Isis Innovation Limited on 13 Jun. 2016 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 16061301. The deposited BAC additionally comprises a transgene encoding the antigen eGFP. In this aspect of the present invention, the polynucleotide sequence for ChAdOx2 preferably does not include the sequence encoding the eGFP antigen.

A further embodiment of the present invention provides a host cell transduced with the viral vector according to the first aspect of the present invention, wherein said host cell is preferably a bacterium, more preferably *E. coli* strain Stellar containing a bacterial artificial chromosome (BAC) containing the cloned genome of ChAdOx2 deposited by Isis Innovation Limited on 13 Jun. 2016 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 16061301. The deposited BAC additionally comprises a transgene encoding the antigen eGFP. In this aspect of the present invention, the polynucleotide sequence for ChAdOx2 preferably does not include the sequence encoding the eGFP antigen. Such a host cell may be used for BAC propagation.

A specific embodiment of the seventh aspect of the present invention provides a Bacterial Artificial Chromosome (BAC) clone comprising the polynucleotide sequence according to the fourth aspect of the present invention, wherein said BAC is the BAC containing the cloned genome of ChAdOx2, deposited in *E. coli* strain Stellar by Isis Innovation Limited on 13 Jun. 2016 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 16061301. The deposited BAC additionally comprises a transgene encoding the antigen eGFP. In this aspect of the present invention, the polynucleotide sequence for ChAdOx2 preferably does not include the sequence encoding the eGFP antigen.

A further aspect of the invention provides a kit, comprising an adenoviral vector according to the first aspect of the invention, or an immunogenic composition according to the second aspect of the invention, together with instructions for use.

The kit may include medical equipment for administering the adenoviral vector or immunogenic composition to a subject, such as a syringe. The kit may comprise instructions for administering the adenoviral vector or immunogenic composition to a subject, and may include specific dosage instructions. The kit may be useful for vaccinating a subject against a disease by inducing or enhancing an immune response, or for otherwise treating or preventing disease in a subject.

For the avoidance of doubt, it is hereby expressly stated that features described herein as 'preferred', 'preferable', "alternative" or the like may be present in the invention in isolation or in any combination with any one or more other features so described (unless the context dictates otherwise) and this constitutes and explicit disclosure of such combinations of features.

All the features of each embodiment described above apply mutatis mutandis to all other embodiments of the present invention.

The invention will now be further described with reference to the following non-limiting examples.

Example 1

Simian Adenvorius (sAd) Vaccine Vector Design and Development

Key considerations in the design of sAd vectors for use as vaccines are similar to those for AdHu5. The vaccine vector must be non-replicating and unlike adenovirus gene therapy vectors have negligible immune modulatory activity. Hence, SAd vectors lack the E1 region encoding viral transactivator proteins which are essential for virus growth and the E3 region encoding immunomodulatory proteins.

The advent of bacterial artificial chromosomes (BACs) coupled to bacteriophage λ Red recombination (recombineering) technology has facilitated the manipulation of large virus genome. Using this approach linear DNA adenovirus genomes isolated from non-human primates have been cloned for use as viral vectors.

Figure 1A:
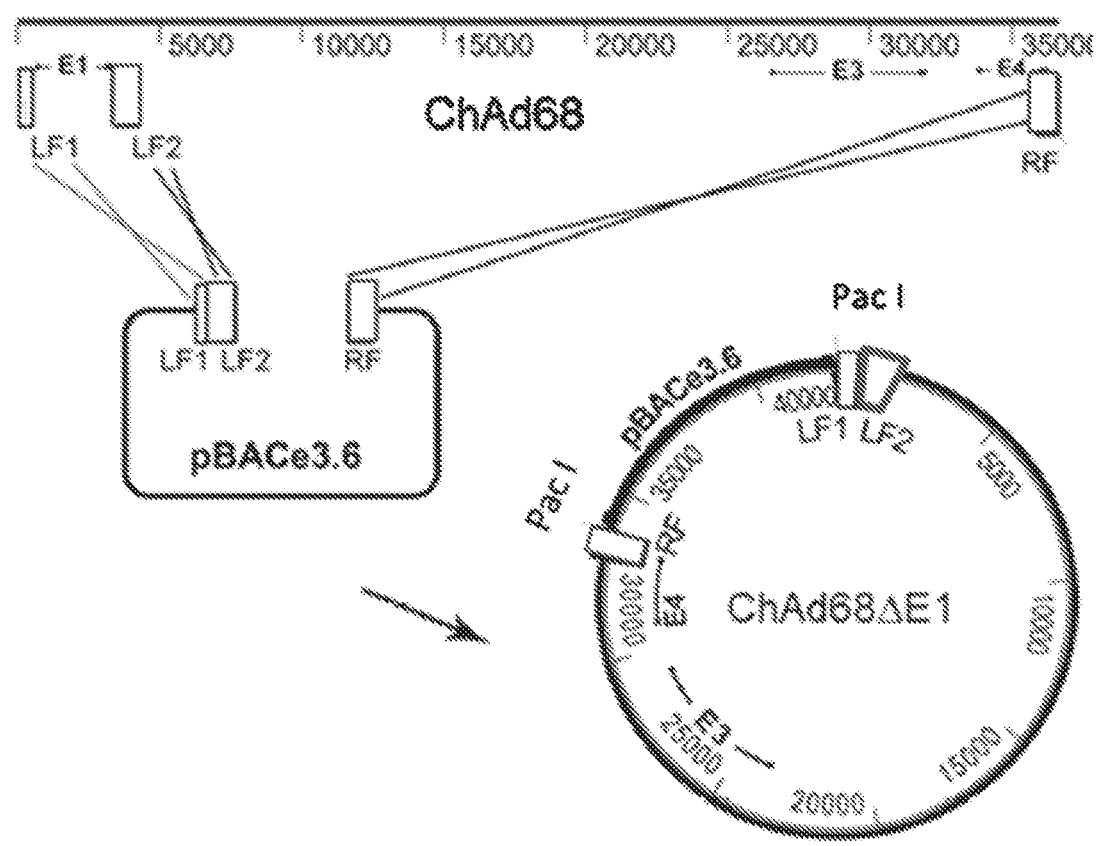

The first stage, following virus isolation and genome sequencing, is either the amplification or artificial synthesis of two products homologous to the left arm of the genome, flanking the E1 region and one, approximately 1000 bp, product homologous to the right arm of the genome each incorporating a unique restriction enzyme site for cloning and genome excision for vector production. These fragments are assembled and inserted into a BAC by conventional restriction enzyme cloning. The virus genome is then inserted into the BAC clone by single step gap repair homologous recombination to generate an E1 deleted viral vector molecular clone (FIG. 1a).

Figure 1C:
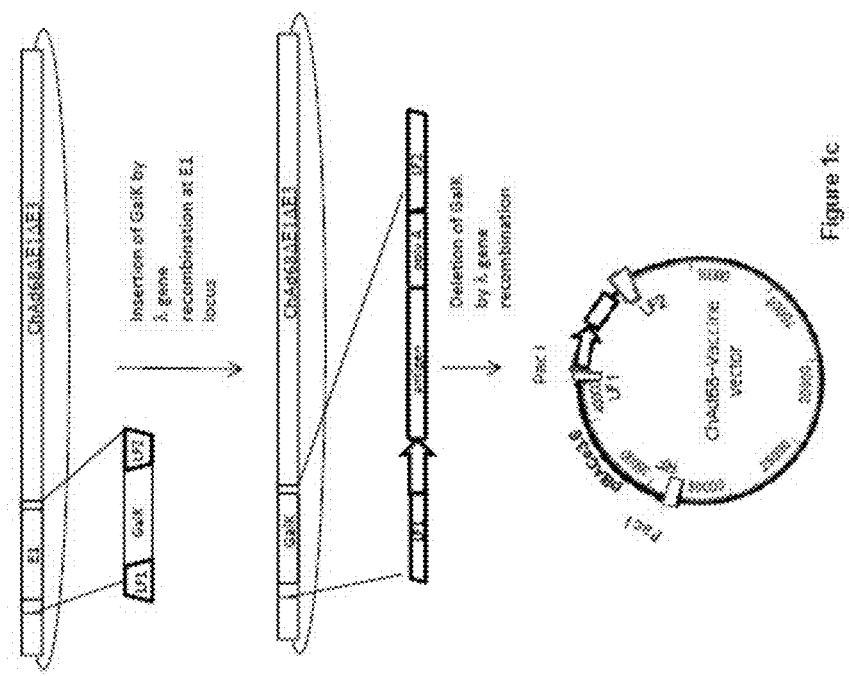
Figure 1B:
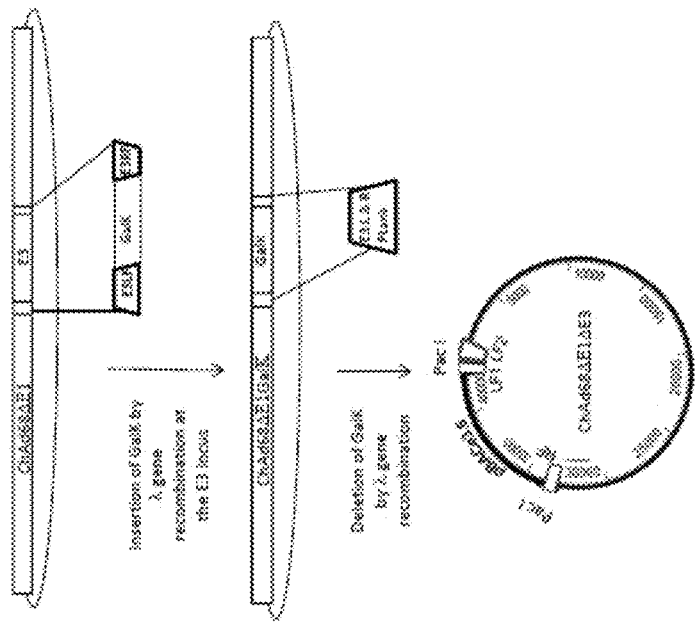

The bacteriophage λ Red recombination (recombineering) system is then used to allow seamless deletion of the adenovirus E3 immunomodulatory genes. Firstly, the bacterial galactokinase gene (GalK) is amplified from the plasmid, pGalK, such that it contains ~50 bp homology arms flanking the E3 region, this gene is inserted at the E3 locus of the BAC rescued adenovirus genome by λ Red recombination. Clones are screened for growth on galactose as this phenotype is attributed to the GalK gene product. The GalK gene is then removed by λ Red recombination with a PCR product comprised of the E3 left and right flanking region only (FIG. 1b).

Positive clones are selected on 2-deoxygalactose media which prevents growth of bacteria expressing the GalK gene. Further manipulation using λ Red recombination firstly to insert the GalK gene and then to exchange it for an antigen expression cassette at the E1 locus completes the engineering of the vaccine vector (FIG. 1c).

The linear virus genome is excised from the BAC using unique restriction enzymes, usually Pac or Pmel, and transfected into complementing cells to generate the viral vector. The antigen cassette typically consists of a strong promoter such as the minimal CMV immediate early promoter, to drive antigen expression, the antigen of interest and a polyadenylation signal.

Figure 2:
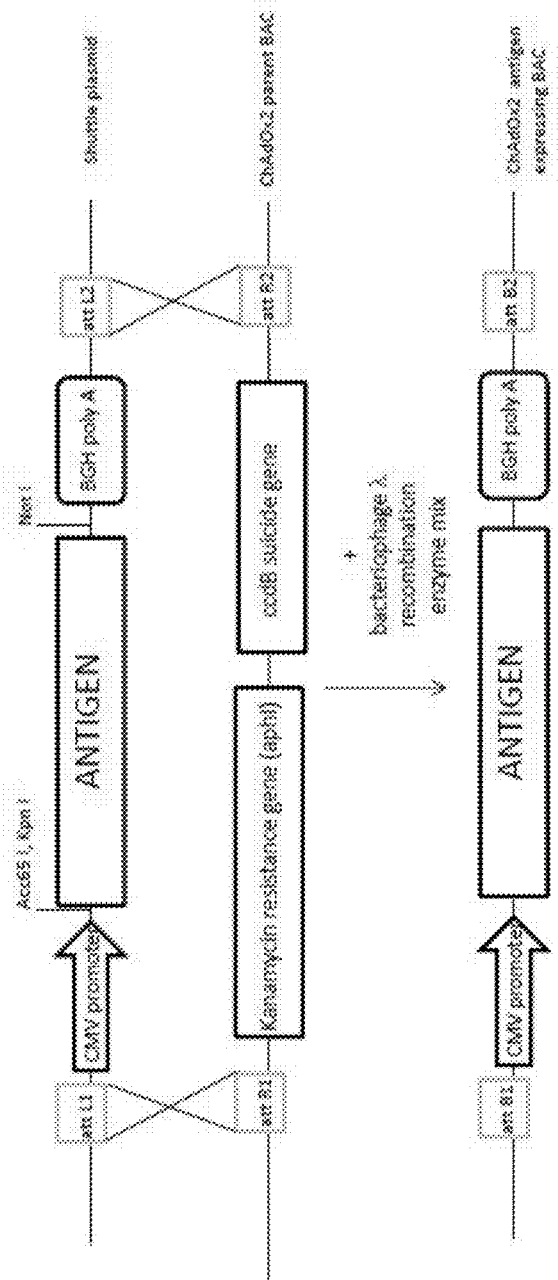

The inventors have generated a molecular toolbox that allows the insertion of any gene easily into a set region within the ChAd genome by inserting universal cassettes expressing a bacteria antibiotic resistance gene flanked by specific recombination sequences, such as attR1 and attR2, derived from bacteriophage A (note this system is based on the Gateway cloning system from Invitrogen), into our ChAd derived vaccine vectors at the E1 locus and/or the E3 locus. Shuttle plasmids containing an antigen expression cassette flanked by specific recombination sites paired with those present in the genome (for example attR1/R2 recombination sequence requires attL1/L2 recombination sequence) allow site specific recombination in the presence of an enzyme mixture containing bacteriophage A integrase, integration host factor and excisionase (FIG. 2).

Although the deleted E1 region from SAds is complemented by AdHu5 E1 proteins constitutively expressed by human embryonic kidney (HEK) 293 cells or PerC.6 cells, viral yields vary depending on SAd serotype. High yields of Pan5, Pan6 and Pan7, all derived from chimpanzees can be obtained from HEK293 cells, whereas ChAd1 yields are poor. For virus vectors with poor replication, further genome manipulation has been shown to increase yields. In the case of AdHu5, the E4 gene products in particular those from orf3, orf4, orf6 and orf6/7 coordinate their function with the E1 proteins (E1A and E1B 55K) and host cell cofactors to bind, regulate and de-repress several cellular functions during viral multiplication. Manipulation of the E4 region can therefore be a promising means of increasing virus yields.

Figure 3:
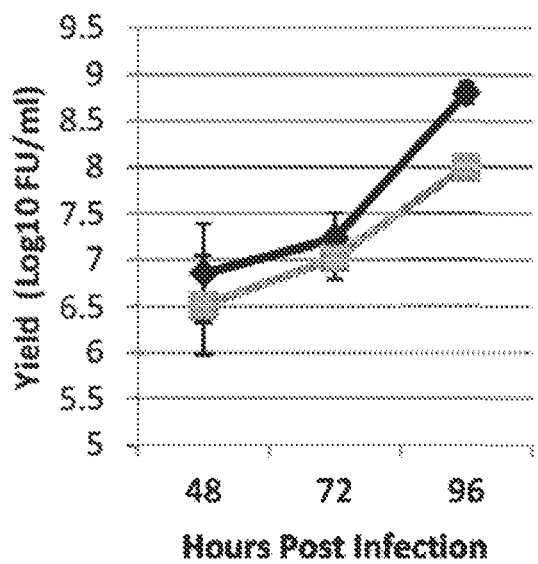

In patent publication WO2012/172277, the present inventors described the generation of a chimeric vaccine vector, ChAdOx1, derived from ChAd serotype Y25 engineered by λ Red recombination to exchange the native E4 orf4 orf6 and orf6/7 genes for those from AdHu5. This vector showed an increase in hexon protein production from HEK 293 cells compared to the ChAd parent virus. Using this approach, the inventors have now generated a novel adenovirus vector according to the present invention, ChAdOx2, an E1/E3 deleted vaccine vector derived from ChAd68 (also referred to as Pan6 and sAd25) containing E4 orf1, orf2 and orf3 from Y25 and E4 orf4, orf6 and orf6/7 from AdHu5 to increase virus yields in HEK 293 cells (FIG. 3).

SAd Vector Engineering to Improve Immunogenicity

Figure 4:
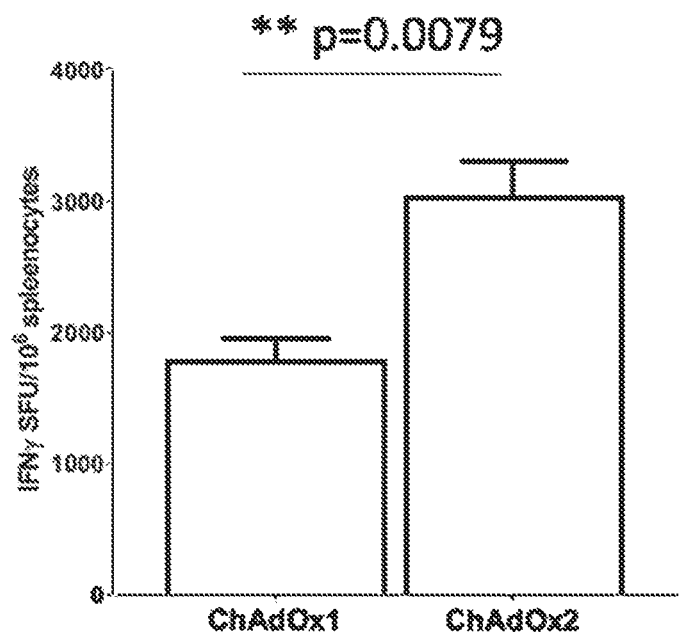

Adenovirus vaccine vectors, regardless of parental origin, can induce humoral, mucosal and cellular immune responses, depending on the route of administration. However, although the T- and B-cell responses elicited are good for most vectors, the level of immunological potency can differ depending on adenovirus vector parental strain/serotype[10] [11]. For example, when the two simian vectors ChAdOx1 (derived from Y25 and disclosed in WN02012/172277) and ChAdOx2 (derived from C68, according to the present invention), which both carried a GFP expression cassette in the E1 locus, were compared, the T-cell response elicited to GFP was significantly higher for ChAdOx2 (FIG. 4).

Example 2: Results from Phase I Clinical Trial of the Candidate *Mycobacterium avium* Subspecies Paratuberculosis (MAP) Vaccine ChAdOx2 HAV A phase I clinical trial was initiated to determine the safety and immunogenicity of the candidate *Mycobacterium avium* subspecies paratuberculosis (MAP) vaccine ChAdOx2 HAV in healthy adult volunteers. The vaccine contains antigens from *Mycobacterium avium* subspecies paratuberculosis (MAP) which is the causative agent for Johne's disease in cattle and has been linked to Crohn's disease in humans.

Figures 5, 6:
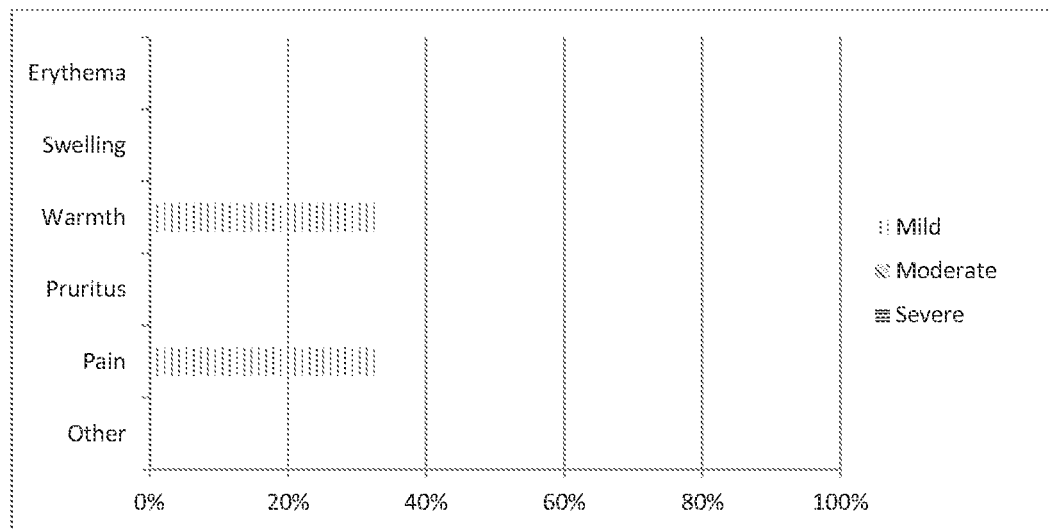
Figure 7:
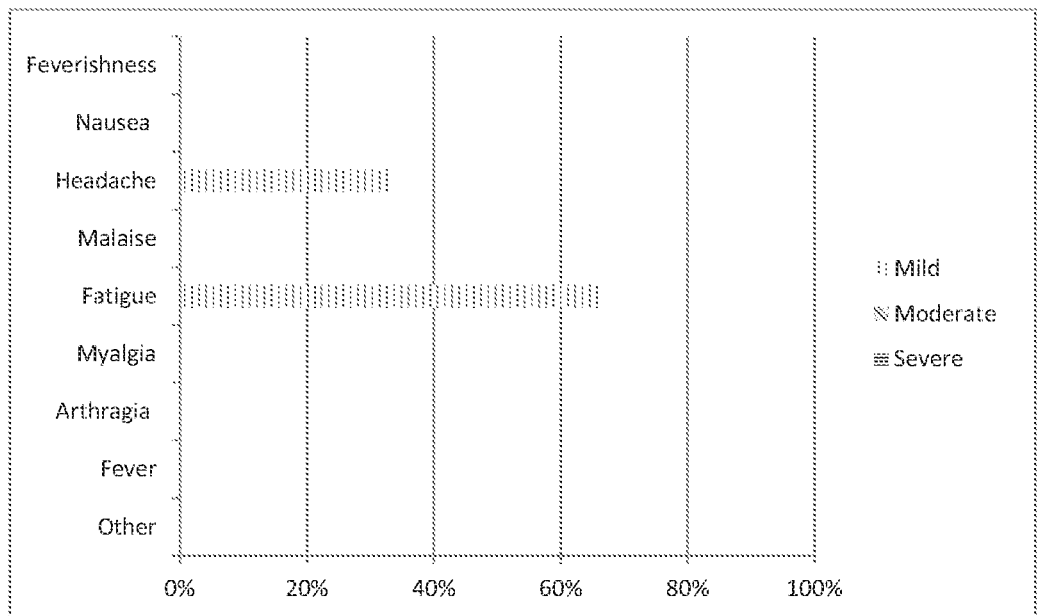
Figure 8:
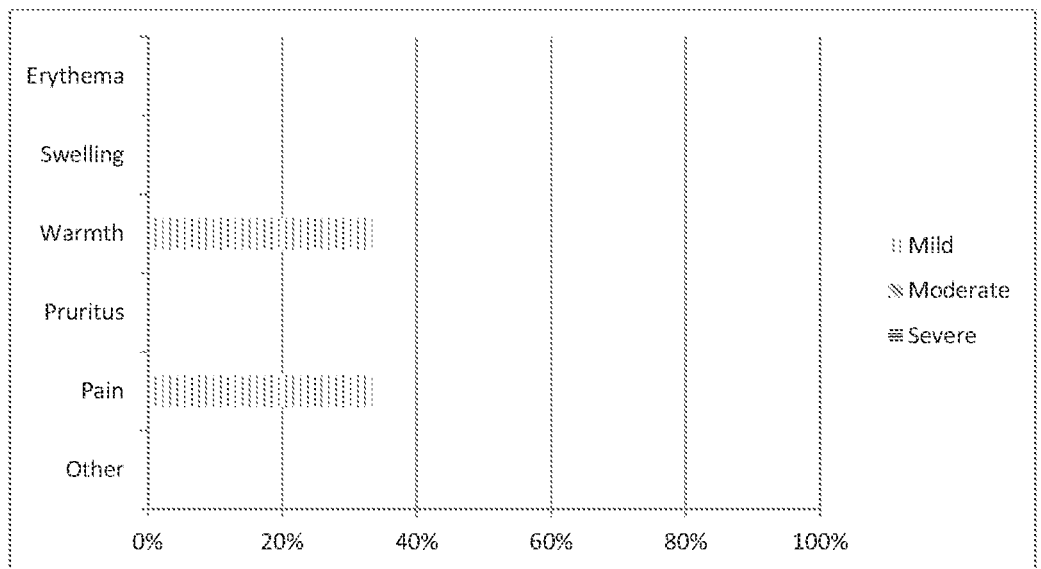
Figure 9:
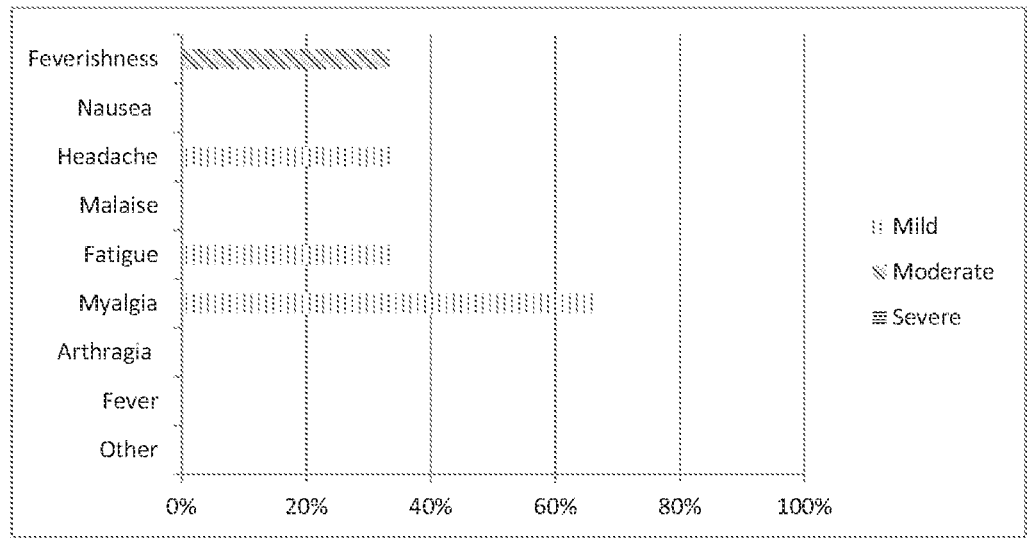
Figure 10:
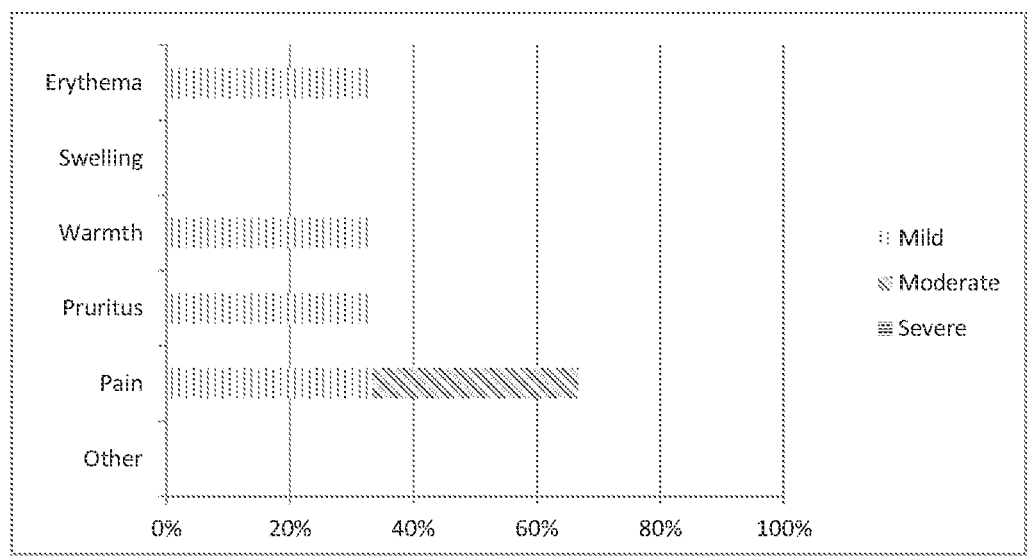
Figure 11:
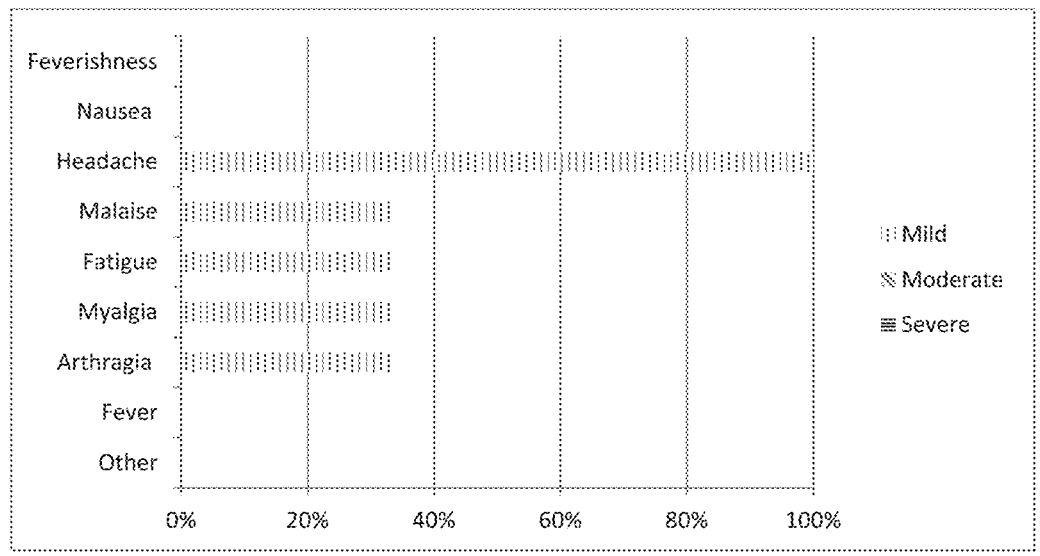

20 volunteers were screened. 13 of these were deemed eligible to take part in the study. 1 volunteer withdrew consent prior to enrolment. 9 participants received their single dose of ChAdOx2 HAV. FIG. 5 shows the study groups (table 1) and the current progress of enrollment (table 2, completed follow-up visits shaded):

FIGS. 6 to 11 show the proportions of volunteers presenting adverse events (AEs) at different dose groups. As can be seen from these figures, the vaccine is safe and well tolerated. There have been no severe or serious AEs related to ChAdOx2 HAV. FIG. 6 shows the proportion of volunteers presenting local AEs after a single dose of ChAdOx2 HAV ($5 \times 10^9$ vp). FIG. 7 shows the proportion of volunteers presenting systemic AEs after a single dose of ChAdOx2 HAV ($5 \times 10^9$ vp). FIG. 8 shows the proportion of volunteers presenting local AEs after a single dose of ChAdOx2 HAV ($2.5 \times 10^{10}$ vp). FIG. 9 shows the proportion of volunteers presenting systemic AEs after a single dose of ChAdOx2 HAV ($2.5 \times 10^{10}$ vp). FIG. 10 shows the proportion of volunteers presenting local AEs after a single dose of ChAdOx2 HAV ($5 \times 10^{10}$ vp). FIG. 11 shows the proportion of volunteers presenting systemic AEs after a single dose of ChAdOx2 HAV ($5 \times 10^{10}$ vp).

Responses to vaccination with ChAdOx2 HAV in humans were assessed using the interferon-gamma ELISPOT assay using freshly-isolated peripheral blood mononuclear cells (PBMC) stimulated with pools of peptides spanning the HAV vaccine construct. Assays were performed prior to vaccination (Day 0) and at one and two months' post vaccination (Day 28 and 56).

Figure 12:
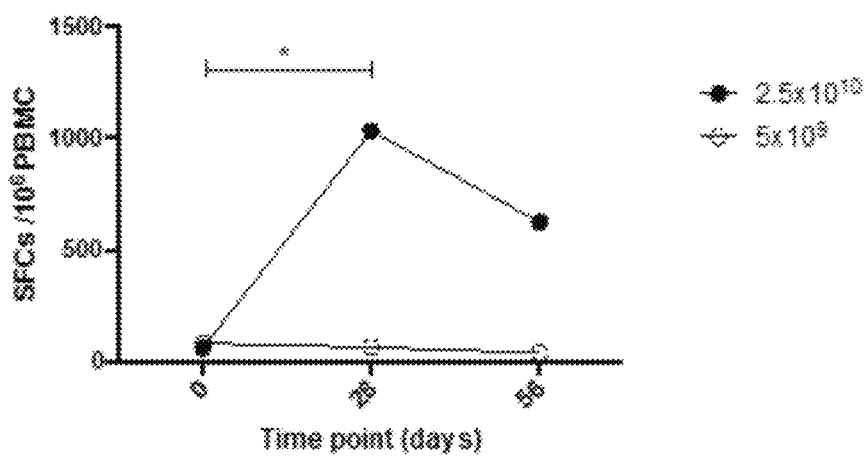

Responses to HAV antigens prior to vaccination were low, with a median response of 104 spot-forming cells per million PBMC (SFC), which increased to a median of 331 SFC at day 28 taking an average across all dose groups (FIG. 12). Responses were higher at day 28 in participants immunised with $2.5 \times 10^{10}$ v.p. than $5 \times 10^9$ v.p. ($p<0.05$, Kruskall-Wallis test with Dunn's multiple comparison test). Individual responses are tabulated, see FIG. 13.

Example 3: Antibody Responses in Mice Vaccinated with ChAdOx2 RabGP

The rabies virus glycoprotein coding sequence (RabGP; ERA strain; Genbank accession number AJ489620.1) was PCR amplified from a plasmid kindly supplied by Hildegund Ertl (Wistar Institute), using primers flanking Acc65I and NotI restriction enzyme sites. After digestion with these enzymes, the fragment was cloned into a similarly digested pENTR4 plasmid providing the human cytomegalovirus major immediate early promoter (IE CMV) that includes intron A and flanked by Gateway® recombination cassettes. Gateway LR recombination cloning (Life Technologies) was used to transfer the transgene cassette into the ChAdOx2 destination vector in the E1-homologous site to produce pBAC ChAdOx2 LPTOS RabGP ERA.

Following enzymatic linearization of the ChAdOx2 RabGP destination plasmid and transfection into HEK293A cells (Invitrogen, Cat. R705-07), the resultant viruses were purified by CsCl gradient ultracentrifugation. The titres were determined on HEK293A cells using anti-hexon immunostaining assay based on the QuickTiter™ Adenovirus Titer Immunoassay kit (Cell Biolabs Inc).

Figures 13, 14:
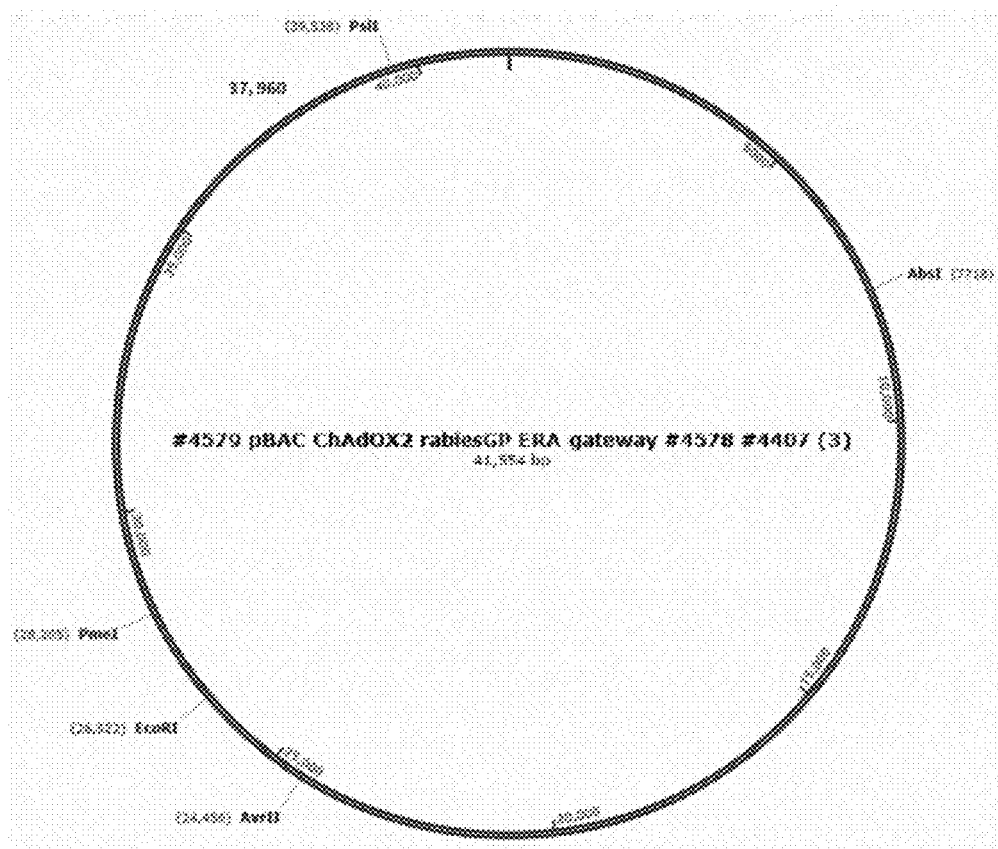
FIG. 14 shows structure of the destination vector for the ChAdOx2 RabGP vaccine.

The destination vector structure is shown in FIG. 14. The amino acid sequence of the rabies glycoprotein is provided in SEQ ID NO. 21.

Vaccine was diluted in PBS prior to administration, and in some cases were mixed with squalene oil-in-water adjuvant (Addavax, Sigma). 6 week old female CD1 outbred mice were immunised with the following formulations (n=6 mice/group), all given intramuscularly into each gastrocnemius.

A: ChAdOx2-RabGP, 1e8 infectivity units (IU)
B: ChAdOx2-RabGP, 1e7 IU
C: ChAdOx2-RabGP, 1e6 IU
D: ChAdOx2-RabGP, with Addavax, 1e8 IU
E: ChAdOx2-RabGP, with Addavax, 1e7 IU
F: ChAdOx2-RabGP, with Addavax, 1e6 IU Serum was collected 28 days after immunisation, and antibody titers were assessed by ELISA against a recombinant rabies glycoprotein (SAD B19 strain, lacking the transmembrane domain, with a C-terminal C-tag and purified using C-tag affinity resin [ThermoFisher]). Results were expressed in arbitrary units, relative to a dilution series/standard curve of a positive control sample, and $\log_{10}$ transformed prior to analysis.

Figure 15:
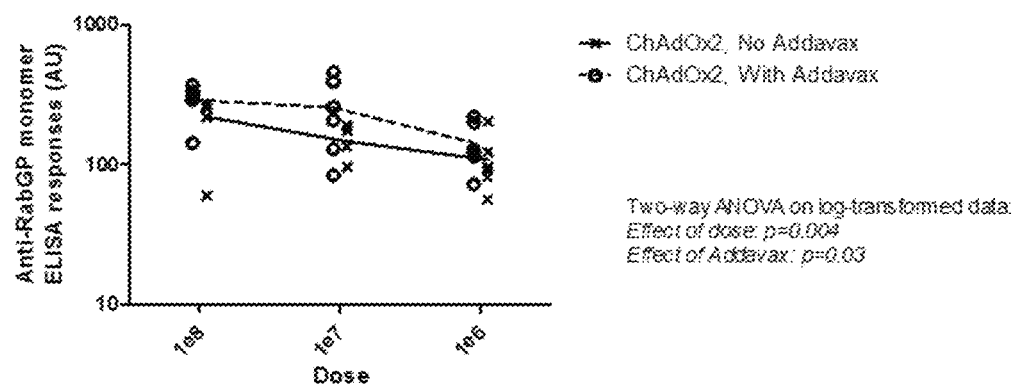
FIG. 15 shows the two-way ANOVA across the ChAdOx2 RabGP vaccine groups immunised with different doses with and without Addavax.

The vaccine induced ELISA-detectable antibody to the rabies glycoprotein, with statistically significant enhancements of antibody titer associated with rising vaccine dose and with co-formulation with Addavax. FIG. 15 shows antibody responses in mice vaccinated with ChAdOx2 RabGP at a range of doses, with and without adjuvant (groups A-F). $p=0.004$ for effect of dose and $p=0.03$ for effect of adjuvant co-formulation the two-way ANOVA across groups A-F.

A comparison of the immunogenicity of the ChAdOx2 vaccine construct with a AdC68 vaccine construct having the same antigen insert was made. The AdC68 was a kind gift of Hildegund Ertl, Wistar Institute, as disclosed in Xiang et al., Novel, Chimpanzee Serotype 68-based Adenoviral Vaccine Carrier for Induction of Antibodies to a Transgene Product, Journal of Virology, 76 (6), pp 2667-2675. The ChAdOx2 vaccine construct was surprisingly found to have higher immunogenicity than the AdC68 vaccine, as shown in FIG. 16.

REFERENCES

1. Buchbinder et al, Lancet, Vol 372, November 2008
2. Farina et al, J. Virol, December 2001, p 11603-11613
3. Dudareva et al, Vaccine 27, 2009, 3501-3504
4. R. Wigand et al, Intervirology, Vol30; 1 1989
5. Roy et al, Hum. Gen. Ther., 2004, 15:519-530
6. Warming et al. Nuc. Acid. Res, 2005, Vol33; 4
7. http://www.invitrogen.com/gateway
8. Havenga et al, J. G. V., 2006, 87, 2135-214
9. Warming, S. et al. Nucleic Acids Res, 2005, Feb. 24; 33(4): e36
10. Colloca, S., et al., Sci Transl Med, 2012. 4(115): p. 115ra2.
11. Quinn, K. M., et al. J Immunol, 2013. 190(6): p. 2720-35.

| List of Sequences | |
| --- | --- |
| SEQ ID NO. | Description of sequence |
| 1 | Complete DNA sequence of C68 |
| 2 | E4 region of C68 |
| 3 | E4Orf1 from AdY25 |
| 4 | E4Orf2 from AdY25 |
| 5 | E4Orf3 from AdY25 |
| 6 | Complete DNA sequence of AdY25 |
| 7 | E4Orf4 from AdHu5 |
| 8 | E4Orf6 from AdHu5 |
| 9 | E4Orf6/7 from AdHu5 |

| List of Sequences | |
|---|---|
| SEQ ID NO. | Description of sequence |
| 10 | ChAdOx2 vector (with Gateway cassette in E1 locus) |
| 11 | Nucleic acid sequence of *M. tuberculosis* protein Ag85A |
| 12 | Amino acid sequence of *M. tuberculosis* protein Ag85A |
| 13 | Nucleic acid sequence of nucleoprotein (NP) and matrix protein 1 (M1) from influenza A virus |
| 14 | Amino acid sequence of nucleoprotein (NP) and matrix protein 1 (M1) from influenza A virus |
| 15 | Linker sequence |
| 16 | E1 region of C68 |
| 17 | E3 region of C68 |
| 18 | Amino acid sequence of C68 hexon protein |
| 19 | Amino acid sequence of C68 penton protein |
| 20 | Amino acid sequence of C68 fibre protein |
| 21 | Amino acid sequence of the rabies glycoprotein |

The invention claimed is:

1. An adenoviral vector comprising the genome of chimpanzee adenovirus C68, wherein the genome of the adenovirus has been modified such that the vector lacks the native E4 locus of the C68 adenovirus and comprises heterologous E4Orf1, E4Orf2 and E4Orf3 coding regions from AdY25, and wherein the adenovirus further comprises heterologous E4Orf4, E4Orf6 and E4Orf6/7 coding regions from AdHu5 in the E4 locus of the adenovirus, and wherein said adenoviral vector lacks a functional E1 locus, and wherein said adenoviral vector lacks an E3 locus, and wherein the adenoviral vector comprises bacteriophage lambda site specific recombination sites at the E1 locus.

2. The adenoviral vector of claim 1, wherein said adenoviral vector comprises one or more capsid proteins selected from the group consisting of:
   (a) a hexon protein encoded by the coding sequence corresponding to nucleotides 18315 to 21116 of SEQ ID NO. 1;
   (b) a penton protein encoded by the coding sequence corresponding to nucleotides 13884 to 15488 of SEQ ID NO. 1; and
   (c) a fibre protein encoded by the coding sequence corresponding to nucleotides 32134 to 33411 of SEQ ID NO. 1.

3. The adenoviral vector of claim 1, further comprising an exogenous nucleotide sequence of interest that encodes a protein or polypeptide.

4. The adenoviral vector of claim 3, wherein said protein or polypeptide is selected from the group comprising an antigen, a molecular adjuvant, an immunostimulatory protein or a recombinase.

5. The adenoviral vector of claim 4, wherein the antigen is a pathogen-derived antigen.

6. The adenoviral vector of claim 5, wherein the pathogen is selected from the group consisting of *M. tuberculosis*, *Plasmodium* spp, influenza virus, HIV, Hepatitis C virus, Cytomegalovirus, Human papilloma virus, rabies virus, measles virus, mumps virus, rubella virus, zika virus, *leishmania* parasites, *Mycobacterium* spp, and *Mycobacterium avium* subspecies paratuberculosis (MAP).

7. The adenoviral vector of claim 6, wherein the antigen is rabies virus glycoprotein.

8. The adenoviral vector of claim 3, wherein said exogenous nucleotide sequence of interest is a miRNA or immunostimulatory RNA sequence.

9. An immunogenic composition comprising the adenoviral vector according to claim 1 and optionally one or more additional active ingredients, a pharmaceutically acceptable carrier, diluent, excipient or adjuvant.

10. A polynucleotide sequence encoding the adenoviral vector of claim 1.

11. A host cell transduced with the adenoviral vector of claim 1.

12. A method of producing the adenoviral vector of claim 1, comprising the step of incorporating a polynucleotide sequence encoding said adenoviral vector into a Bacterial Artificial Chromosome (BAC) to produce an Ad-BAC vector.

13. A Bacterial Artificial Chromosome (BAC) clone comprising the polynucleotide sequence of claim 10.

14. A packaging cell line producing the viral vector of claim 1.

15. The packaging cell line of claim 14, wherein said cell comprises the complement of any genes functionally delete in the viral vector comprising the genome of an adenovirus other than AdHu5 and AdY25, wherein the genome of the adenovirus has been modified such that the vector lacks the native E4 locus of the adenovirus and comprises heterologous E4Orf1, E4Orf2 and E4Orf3 coding regions from AdY25.

16. A kit comprising: (i) one of an adenoviral vector according to claim 1 or an immunogenic composition comprising the adenoviral vector according to claim 1, and (ii) instructions for use.

17. A method of treating or preventing a disease comprising administering the immunogenic composition according to claim 9 to a subject in need thereof.

18. The method of claim 17, wherein the disease is selected from the group comprising tuberculosis, Johne's disease, Crohn's disease, malaria, influenza, HIV/AIDS, Hepatitis C virus infection, Cytomegalovirus infection, Human papilloma virus infection, adenoviral infection, leishmaniasis, *Streptococcus* spp infection, *Staphylococcus* spp infection, *Meningococcus* spp infection, foot and mouth disease, chikungunya virus infection, Zika virus infection, rabies, Crimean Congo haemorrhagic fever, Ebola virus infection, Marburg, Lassa fever, MERS and SARS coronavirus disease, and Nipah and Rift Valley fever.

19. The method of claim 17, wherein the method comprises delivering a transgene into a host cell of the subject.

20. An adenoviral vector comprising the genome of chimpanzee adenovirus C68,
wherein the genome of the adenovirus has been modified such that the vector lacks the native E4 locus of the C68 adenovirus and comprises heterologous E4Orf1, E4Orf2 and E4Orf3 coding regions from AdY25,
wherein the adenovirus further comprises heterologous E4Orf4, E4Orf6 and E4Orf6/7 coding regions from AdHu5 in the E4 locus of the adenovirus,
wherein said adenoviral vector lacks a functional E1 locus,
wherein said adenoviral vector lacks an E3 locus,
wherein the adenoviral vector comprises bacteriophage lambda site specific recombination sites at the E1 locus, and
wherein the bacteriophage lambda site specific recombination sites are attR1 and attR2.

21. An adenoviral vector comprising the genome of chimpanzee adenovirus C68,
wherein the genome of the adenovirus has been modified such that the vector lacks the native E4 locus of the C68 adenovirus and comprises heterologous E4Orf1, E4Orf2 and E4Orf3 coding regions from AdY25,
wherein the adenovirus further comprises heterologous E4Orf4, E4Orf6 and E4Orf6/7 coding regions from AdHu5 in the E4 locus of the adenovirus,
wherein said adenoviral vector lacks a functional E1 locus,
wherein said adenoviral vector lacks an E3 locus,
wherein the adenoviral vector comprises bacteriophage lambda site specific recombination sites at the E1 locus, and
wherein the vector comprises the polynucleotide sequence of SEQ ID NO: 10.

* * * * *